US012605424B2

(12) United States Patent
Matalon et al.

(10) Patent No.: US 12,605,424 B2
(45) Date of Patent: Apr. 21, 2026

(54) TREATMENT AND PREVENTION OF PULMONARY INJURY

(71) Applicant: THE UAB RESEARCH FOUNDATION, Birmingham, AL (US)

(72) Inventors: Sadis Matalon, Birmingham, AL (US); Saurabh Aggarwal, Birmingham, AL (US); Tamas Jilling, Birmingham, AL (US); Rakesh Patel, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 886 days.

(21) Appl. No.: 17/640,534

(22) PCT Filed: Sep. 4, 2020

(86) PCT No.: PCT/US2020/049436
§ 371 (c)(1),
(2) Date: Mar. 4, 2022

(87) PCT Pub. No.: WO2021/046371
PCT Pub. Date: Mar. 11, 2021

(65) Prior Publication Data

US 2022/0362334 A1 Nov. 17, 2022

Related U.S. Application Data

(60) Provisional application No. 62/896,427, filed on Sep. 5, 2019, provisional application No. 62/896,419, filed on Sep. 5, 2019, provisional application No. 63/014,902, filed on Apr. 24, 2020.

(51) Int. Cl.

| | |
|---|---|
| ***A61K 38/17*** | (2006.01) |
| ***A61K 31/7135*** | (2006.01) |
| ***A61K 33/00*** | (2006.01) |
| ***A61P 11/00*** | (2006.01) |

(52) U.S. Cl.
CPC ...... *A61K 38/1709* (2013.01); *A61K 31/7135* (2013.01); *A61K 33/00* (2013.01); *A61P 11/00* (2018.01)

(58) Field of Classification Search
None
See application file for complete search history.

(56) References Cited

U.S. PATENT DOCUMENTS

| | | | |
|---|---|---|---|
| 8,568,793 | B2 | 10/2013 | Sherman et al. |
| 8,920,852 | B2 | 12/2014 | Sherman et al. |
| 9,283,249 | B2 | 3/2016 | Sherman et al. |
| 9,504,709 | B2 | 11/2016 | Sherman et al. |
| 9,597,354 | B2 | 3/2017 | Sherman et al. |
| 9,675,637 | B2 | 6/2017 | Gladwin et al. |
| 9,687,505 | B2 | 6/2017 | Sherman et al. |
| 9,687,506 | B2 | 6/2017 | Sherman et al. |
| 10,251,910 | B2 | 4/2019 | Sherman et al. |
| 10,456,417 | B2 | 10/2019 | Sherman et al. |
| 2007/0154569 | A1 | 7/2007 | Gladwin et al. |
| 2010/0298367 | A1 | 11/2010 | Brown et al. |
| 2015/0353590 | A1 | 12/2015 | Boss et al. |
| 2016/0374950 | A1 | 12/2016 | Yacoub et al. |
| 2017/0296463 | A1 | 10/2017 | Minton et al. |
| 2019/0134080 | A1 | 5/2019 | Miller et al. |

FOREIGN PATENT DOCUMENTS

| | | |
|---|---|---|
| WO | 2012019178 A2 | 2/2012 |
| WO | 2021046456 A2 | 3/2021 |

OTHER PUBLICATIONS

Aggarwal, S., et al., Heme attenuation ameliorates irritant gas inhalation-induced acute lung injury, Antioxidants & Redox Signaling, vol. 24, 99-112 (2016) (Year: 2016).*
Aggarwal, S., Ahmad, I., et al., Mitochondrial DNA Repair Ameliorates Inhalation Lung Injury, A16 Chemical Threats and Injury: Mechanisms and Treatment / Mini Symposium / Sunday, May 19/9:15 AM-11:15 AM / Dallas Ballroom G (Level 3), Omni Dallas Downtown, Am J Respir Crit Care Med 2019; 199:A1020 (Year: 2019).*
Aggarwal, S., et al., Heme Attenuation Ameliorates Irritant Gas Inhalation-Induced Acute Lung Injury, Antioxidants & Redox Signaling, 24, 99-112(2016) (Year: 2016).*
Zhou T. , et al. Halogen Inhalation-Induced Lung Injury and Acute Respiratory Distress Syndrome; Chin Med J (Engl), May 2018, 131(10): 1214-1219.
Lam A., et al., Role of heme in bromine-induced lung injury; Ann N Y Acad Sci., May 2016; 1374(1): 105-110.
Aggarwal S., et al. Heme attenuation ameliorates irritant gas inhalation-induced acute lung injury. Antioxid Redox Signal, 2016;24(2):99-112. PMID 26376667.
Summerhill E.M., et al. An Official American Thoracic Society Workshop Report: Chemical Inhalational Disasters ; Ann Am Thorac Soc, Jun. 2017, vol. 14, No. 6, pp. 1060-1072.
Britt R. D., et al. The Thioredoxin Reductase-1 Inhibitor Aurothioglucose Attenuates Lung Injury and Improves Survival in a Murine Model of Acute Respiratory Distress Syndrome; Antioxid Redox Signal, Jun. 10, 2014; 20(17): 2681-2691.
Honavar J., et al. Nitrite therapy improves survival postexposure to chlorine gas; Am J Physiol Lung Cell Mol Physiol. Dec. 1, 2014;307: L888-94.
Yuan T., et al. Salubrinal Protects Against Cigarette Smoke Extract-induced HBEpC Apoptosis Likely via Regulating the Activity of PERK-elF2? Signaling Pathway; Archives of Medical Research, vol. 43, Issue 7, Oct. 2012, pp. 522-529.

(Continued)

*Primary Examiner* — H. Sarah Park
(74) *Attorney, Agent, or Firm* — Nicholas J. Landau; Maynard Nexsen PC

(57) ABSTRACT

Hemopexin, salubrinal, aurothioglucose, and nitrite find uses in treating pulmonary injury from several causes, alone and in combination. Methods of treatment, methods of prevention, and pharmaceutical compositions are provided with those components.

17 Claims, 49 Drawing Sheets

Specification includes a Sequence Listing.

(56) References Cited

OTHER PUBLICATIONS

He Y. Y., et al. Salubrinal attenuates right ventricular hypertrophy and dysfunction in hypoxic pulmonary hypertension of rats; Vascular Pharmacology, vol. 87, Dec. 2016, pp. 190-198.
Zhou T., et al. Instillation of hyaluronan reverses acid instillation injury to the mammalian blood gas barrier. Am. J. Physiol. Lung Cell Mol. Physiol., 314 (2018). PMID 29368549.
Miller MR, et al. Standardisation of spirometry. Eur Respir J. 2005;26(2):319-338. PMID 16055882.
Vogelmeier CF, et al. Global Strategy for the Diagnosis, Management, and Prevention of Chronic Obstructive Lung Disease 2017 Report. GOLD Executive Summary. Am J Respir Crit Care Med. 2017; 195(5):557-582. PMID 28128970.
Raju SV, et al. A ferret model of COPD-related chronic bronchitis. JCI Insight. 2016; 1(15):e87536. PMID 27699245.
Leustik M, et al. Mitigation of chlorine-induced lung injury by low-molecular-weight antioxidants. Am J Physiol Lung Cell Mol Physiol. 2008;295(5):L733-L743. PMID 18708632.
Song W, et al. Inhibition of lung fluid clearance and epithelial Na+ channels by chlorine, hypochlorous acid, and chloramines. J Biol Chem. 2010;285(13):9716-9728. PMID 20716287.
Vardell E. JoVE: the Journal of Visualized Experiments. Med Ref Serv Q. 2015;34(1):88-97. PMID 25611443.
Li C, et al. Chlorine induces the unfolded protein response in murine lungs and skin. Am J Respir Cell Mol Biol. 2013;49(2):197-203. PMID 23668485.
Sharafkhaneh A, Hanania NA, Kim V. Pathogenesis of emphysema: from the bench to the bedside. Proc Am Thorac Soc. 2008;5(4):475-477. PMID 18453358.
Boyce M, et al. A selective inhibitor of elF2alpha dephosphorylation protects cells from ER stress. Science. 2005;307(5711):935-939. PMID 15705855.
Moreno JA, et al. Sustained translational repression by elF2α-P mediates prion neurodegeneration. Nature. 2012;485(7399):507-511. PMID 22622579.
Liu CL, et al. Salubrinal protects against tunicamycin and hypoxia induced cardiomyocyte apoptosis via the PERK-elF2α signaling pathway. J Geriatr Cardiol. 2012;9(3):258-268. PMID 23097656.
X. Han, et al. Shotgun lipidomics of phosphoethanolamine-containing lipids in biological samples after one-step in situ derivatization. J. Lipid Res., 46 (2005). PMID 15834120.
H.G. Folkesson, et al. Acid aspiration-induced lung injury in rabbits is mediated by interleukin-8-dependent mechanisms. J. Clin. Invest., 96 (1995). PMID 7615779.
S.A. Cucinell. Review of the toxicity of long-term phosgene exposure. Arch. Environ. Health, 28 (1974). PMID 4207008.
V.G. Demarco, et al. Obesity-related alterations in cardiac lipid profile and nondipping blood pressure pattern during transition to diastolic dysfunction in male db/db mice. Endocrinology, 154 (2013). PMID 23142808.
S. Balakrishna, et al. TRPV4 inhibition counteracts edema and inflammation and improves pulmonary function and oxygen saturation in chemically induced acute lung injury. Am. J. Physiol. Lung Cell Mol. Physiol., 307 (2014). PMID 24838754.
P.T. Filipczak, et al. NOS-2 inhibition in phosgene-induced acute lung injury. Toxicol. Sci., 146 (2015). PMID 25870319.
S. Aggarwal, et al. Heme scavenging reduces pulmonary endoplasmic reticulum stress, fibrosis, and emphysema. JCI Insight, 3 (2018). PMID 30385726.
J.A. Lambert, et al. Mechanisms and treatment of halogen inhalation-induced pulmonary and systemic injuries in pregnant mice. Hypertension, 70 (2017). PMID 28607126.
A. Gaggar, et al. There is blood in the water: hemolysis, hemoglobin, and heme in acute lung injury. Am. J. Physiol. Lung Cell Mol. Physiol., 311 (2016). PMID 27542810.
I.Y. Haddad, et al. Mechanisms of peroxynitrite-induced injury to pulmonary surfactants. Am. J. Physiol., 265 (1993). PMID 8279572.
E.J. Lee, et al. Dynamic arterial blood gas analysis in conscious, unrestrained C57BL/6J mice during exposure to intermittent hypoxia. J. Appl. Physiol., 107 (2009). PMID 19056995.
M. Gutch, et al. Acute accidental phosgene poisoning. BMJ Case Rep., 2012 (2012). PMID 22602834.
M.A. Duerr, et al. Bromofatty aldehyde derived from bromine exposure and myeloperoxidase and eosinophil peroxidase modify GSH and protein. J. Lipid Res., 59 (2018). PMID 29444934.
D.A. Ford, et al. Formation of chlorinated lipids post-chlorine gas exposure. J. Lipid Res., 57 (2016). PMID 27324796.
M.W. Oh, et al. Chlorinated fatty acids are biomarkers and potential mediators of chlorine gas toxicity. Free Radic. Biol. Med., 76 (2014).
R.V. Branchflower, et al. Nephrotoxicity of chloroform: metabolism to phosgene by the mouse kidney, Toxicol. Appl. Pharmacol., 72 (1984). PMID 6143425.
N. Hamasaki, et al. Band 3 protein: physiology, function and structure. Cell Mol. Biol., 42 (1996). PMID 8960778.
S.R. Goodman, et al. Erythrocyte membrane skeletal protein bands 4.1 a and b are sequence-related phosphoprotein, J. Biol. Chem., 257 (1982). PMID 7068651.
Albert C.J., et al. Eosinophil peroxidase-derived reactive brominating species target the vinyl ether bond of plasmalogens generating a novel chemoattractant, alpha-bromo fatty aldehyde. J. Biol. Chem. 278:8942-8950 (2003). PMID 12643282.
Wacker B.K., et al. Strategies for the analysis of chlorinated lipids in biological systems. Free Radic. Biol. Med. 59:92-99 (2013). PMID 22713364.
Duerr M.A., et al. Identification of glutathione adducts of alpha-chlorofatty aldehydes produced in activated neutrophils. J. Lipid Res. 56:1014-1024 (2015). PMID 25814023.
Pan D. et al. The effect of polymeric nanoparticles on biocompatibility of carrier red blood cells. PloS One. 11(2016). PMID 27003833.
Lazrak A. et al. Enhancement of alveolar epithelial sodium channel activity with decreased cystic fibrosis transmembrane conductance regulator expression in mouse lung. Am. J. Physiol. Lung Cell Mol. Physiol. 301:L557-L567 (2011). PMID 21743028.
Meyer N.J. et al. Myeloperoxidase-derived 2-chlorofatty acids contribute to human sepsis mortality via acute respiratory distress syndrome. JCI Insight. 2(2017). PMID 29212955.
Hollenhorst M.I. et al. Ion transport by pulmonary epithelia. J. Biomed. Biotechnol. 2011:174306 (2011). PMID 22131798.
Lazrak A. et al. Influenza virus M2 protein inhibits epithelial sodium channels by increasing reactive oxygen species. Faseb. J.: Official Publication of the Federation of American Societies for Experimental Biology. 23:3829-3842 (2009). PMID 19596899.
Rojas D, et al. Osmotic fragility of red blood cells, lipid peroxidation and Ca(2)(+)-ATPase activity of placental homogenates and red blood cell ghosts in salt-loaded pregnant rats. J Matern Fetal Neonatal Med. 29:229-33 (2016). PMID 25682780.
Hod I. Osmotic fragility of rat embryo red blood cells collected during intrauterine growth. Lab Anim 18:81-3 (1984). PMID 10628794.
Zhurova M, et al. Osmotic tolerance limits of red blood cells from umbilical cord blood. Cryobiology 69:48-54 (2014).PMID 24836371.
Matsuoka M, et al. Experimental Evidence Shows Salubrinal, an elR2α Dephosphorylation Inhibitor, Reduces Xentoxicant-Induced Cellular Damage Jul. 17, 2015 (2015); 16, 16275-16287; International Journal of Molecular Sciences.
Aggarwal et al., "Phosgene Inhalation Causes Hemolysis and Acute Lung Injury,", Toxicology Letters, vol. 312, 2019, pp. 204-213.
Honavar et al., "Nitrite Therapy Prevents Chlorine Gas Toxicity in Rabbits," Toxicol Lett, vol. 271, Apr. 5, 2017, pp. 20-25.
Samal et al., "Post Chlorine Gas Exposure Administration of Nitrite Prevents Lung Injury: Effect of Administration Modality," Free Radic. Biol. Med., vol. 53, Issue 7, Oct. 1, 2012, pp. 1431-1439.
International Preliminary Report on Patentability received for International Patent Application No. PCT/US2020/049436, mailed on Mar. 17, 2022, 13 pages.
International Search Report and Written Opinion received for International Patent Application No. PCT/US2020/049436, mailed on Nov. 5, 2020, 16 pages.
International Preliminary Report on Patentability received for International Patent Application No. PCT/US2020/049551, mailed on Mar. 17, 2022, 07 pages.

(56) References Cited

OTHER PUBLICATIONS

International Search Report and Written Opinion received for International Patent Application No. PCT/US2020/049551, mailed on Dec. 17, 2020, 08 pages.

* cited by examiner

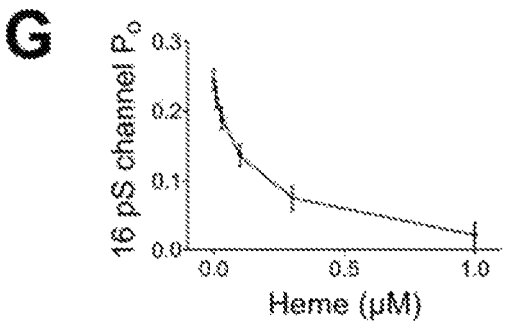
FIG. 28G
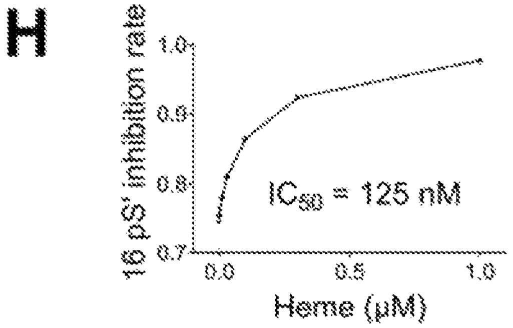
FIG. 28H
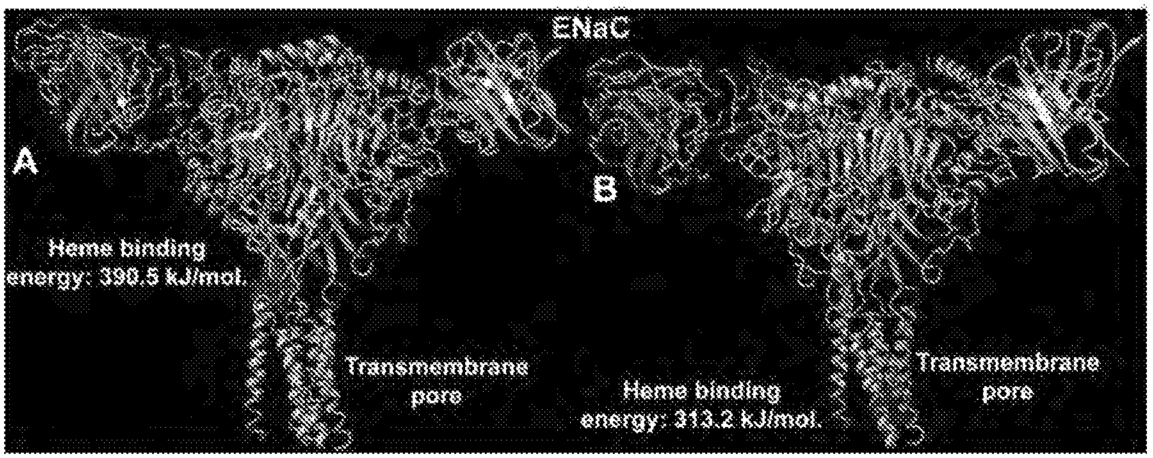
FIG. 29A
FIG. 29B

TREATMENT AND PREVENTION OF PULMONARY INJURY

CROSS-REFERENCE TO RELATED APPLICATIONS

This is a national stage under 35 U.S.C. 371 of International Patent Application PCT/US2020/049436, filed on 4 Sep. 2020 (pending). International Patent Application PCT/US2020/049436 cites the priority of U.S. Provisional Application No. 62/896,427, filed 5 Sep. 2019, which is incorporated herein by reference in its entirety. This application also cites the priority of U.S. Provisional Application No. 62/896,419, filed Sep. 5, 2019, and U.S. Provisional Application No. 63/014,902, filed Apr. 24, 2020.

STATEMENT REGARDING FEDERALLY SPONSORED RESEARCH OR DEVELOPMENT

This invention was made with government support under HL123940, ES027697, ES015676, ES026458, and ES026219 awarded by the National Institutes of Health. The government has certain rights in the invention.

In this context "government" refers to the government of the United States of America.

BACKGROUND

Field of the Disclosure

The present disclosure relates generally to medicinal compositions for the treatment of lung injury. Such compositions as well as methods for use therewith are provided.

Background

The halogens chlorine ($Cl_2$) and bromine ($Br_2$) and the halogenated highly reactive $Cl_2$ containing compound phosgene ($COCl_2$) exhibit a threat to humans, due to the potential of either accidental or malicious release from storage areas or during the course of their transportation. Due to a lack of mechanistic understanding of their pulmonary and systemic toxicities and the consequent absence of specific and effective countermeasures, exposed individuals are treated by supportive, non-specific care by first responders and during hospitalization. Due to the inherent developmental differences, neonates and young children react differently to hyperoxia, hypoxia, airway infections and exposure to toxic gases than adults. Neonates have only ~15% of the number of alveoli of adults. The newborn lung is in a stage of active alveolar development that requires precise coordination of proliferation, migration and differentiation of cells. This developmental process continues until young adulthood (18-20 years of age), but the critical window of vulnerability is in the 0-4 years period when the developmental process is most robust. Injury to developing lungs carries the particular risk of aberrant development, and permanent airway and alveolar remodeling, resulting in death in childhood or lifelong increased risk of morbidity. For instance, the most common cause of death for premature neonates surviving beyond postnatal day 60 is BPD, which is characterized by persistent abnormalities in lung structure and function. Additionally, survivors with BPD have a lifetime increased risk for pulmonary infections, poor baseline pulmonary function and asthma, pulmonary arterial hypertension and poor neurodevelopmental outcome.

Consequently there is a need for effective treatment for pulmonary injury caused by exposure to halogenated gasses, and a general need for effective treatment of pulmonary injury that is safe for children and neonates.

SUMMARY

It has been discovered that Hpx is effective to treat some forms of pulmonary injury that were not previously associated with free heme. It has also been discovered that Hpx is well tolerated by neonates, who generally have a low tolerance for existing therapeutic agents for pulmonary injury.

In a first aspect, a method of treating or preventing toxicity from exposure to a chemical agent in a subject in need thereof is provided, the method comprising: administering an effective amount of a hemopexin (Hpx) compound to the subject; wherein the chemical agent is selected from $Cl_2$, phosgene, and a combination thereof; and wherein the Hpx compound is at least one of: Hpx, a prodrug of Hpx, a pharmaceutically acceptable salt of at least one of the foregoing, and an ester of at least one of the foregoing.

In a second aspect, a method of treating or preventing pulmonary injury in a neonate is provided, the method comprising: administering an effective amount of a hemopexin (Hpx) compound to the neonate, wherein the Hpx compound is at least one of: Hpx, a prodrug of Hpx, a pharmaceutically acceptable salt of at least one of the foregoing, and an ester of at least one of the foregoing.

In a third aspect, a method of treating or preventing chronic pulmonary injury in a subject in need thereof is provided, the method comprising: administering an effective amount of a hemopexin (Hpx) compound to the subject; wherein the Hpx compound is at least one of: Hpx, a prodrug of Hpx, a pharmaceutically acceptable salt of at least one of the foregoing, and an ester of at least one of the foregoing; wherein the chronic pulmonary injury manifests itself as chronic obstructive pulmonary disease (COPD).

In a fourth aspect, a method of treating or preventing pulmonary bacterial infection in a subject who has suffered pulmonary injury associated with exposure to a chemical agent, the method comprising administering an effective amount of a hemopexin (Hpx) compound to the subject; wherein the Hpx compound is at least one of: Hpx, a prodrug of Hpx, a pharmaceutically acceptable salt of at least one of the foregoing, and an ester of at least one of the foregoing.

In a fifth aspect, a method of treating or preventing impaired immune cell function associated with exposure to a chemical agent in a subject in need thereof is provided, the method comprising administering an effective amount of a hemopexin (Hpx) compound to the subject; wherein the Hpx compound is at least one of: Hpx, a prodrug of Hpx, a pharmaceutically acceptable salt of at least one of the foregoing, and an ester of at least one of the foregoing.

In a sixth aspect, a method of treating or preventing pulmonary injury associated with acellular heme in a subject in need thereof is provided, the method comprising: administering an effective amount of a hemopexin (Hpx) compound to the subject; and administering an effective amount of an aurothioglucose (ATG) compound to the subject; wherein the Hpx compound is at least one of: Hpx, a prodrug of Hpx, a pharmaceutically acceptable salt of at least one of the foregoing, and an ester of at least one of the foregoing; and wherein the ATG compound is at least one of: ATG, a prodrug of ATG, a pharmaceutically acceptable salt of at least one of the foregoing, and an ester of at least one of the foregoing.

In a seventh aspect, a method of treating or preventing pulmonary dysfunction in a subject in need thereof is provided, the method comprising administering an effective amount of a salubrinal compound to the subject; wherein the pulmonary dysfunction is associated with one or more of endoplasmic reticulum (ER) stress, airway fibrosis, and emphysema; wherein the salubrinal compound is at least one of: salubrinal, a prodrug of salubrinal, a pharmaceutically acceptable salt of at least one of the foregoing, and an ester of at least one of the foregoing.

In an eighth aspect, a pharmaceutical composition for the treatment of pulmonary injury is provided, comprising: a first effective amount of a hemopexin (Hpx) compound and a second effective amount of an aurothioglucose (ATG) compound; wherein the Hpx compound is at least one of: Hpx, a prodrug of Hpx, a pharmaceutically acceptable salt of at least one of the foregoing, and an ester of at least one of the foregoing; and wherein the ATG compound is at least one of: ATG, a prodrug of ATG, a pharmaceutically acceptable salt of at least one of the foregoing, and an ester of at least one of the foregoing.

In a ninth aspect, a method of treating or preventing pulmonary injury in a subject is provided, the method comprising: administering an effective amount of a hemopexin (Hpx) compound to the subject; and administering an effective amount of a nitrite compound to the subject; wherein the Hpx compound is at least one of: Hpx, a prodrug of Hpx, a pharmaceutically acceptable salt of at least one of the foregoing, and an ester of at least one of the foregoing; and wherein the nitrite compound is at least one of nitrite, nitrous acid, a prodrug of nitrite, a pharmaceutically acceptable salt of at least one of the foregoing, and an ester of at least one of the foregoing.

In a tenth aspect, a pharmaceutical composition for the treatment of pulmonary injury is provided, comprising: a first effective amount of a hemopexin (Hpx) compound and a second effective amount of a nitrite compound; wherein the Hpx compound is at least one of: Hpx, a prodrug of Hpx, a pharmaceutically acceptable salt of at least one of the foregoing, and an ester of at least one of the foregoing; and wherein the nitrite compound is at least one of nitrite, nitrous acid, a prodrug of nitrite, a pharmaceutically acceptable salt of at least one of the foregoing, and an ester of at least one of the foregoing.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 1A is a graph showing the total heme levels in COPD patients compared with healthy individuals (P=0.06) (n=18-22). FIG. 1B is a graph showing significantly elevated plasma heme in COPD patients with GOLD stage 4 disease compared with the healthy individuals or patients with the mild disease (n=6-18). FIG. 1C is a graph showing significantly higher plasma heme levels in ferrets exposed to cigarette smoke for 6 months, which induced emphysema and attenuated lung function (n=6-8). FIG. 1D is a graph showing that GOLD stage 4 COPD patients had significantly higher levels of ER stress marker Grp78/Bip (n=6-14). Values are means±SEM. *P<0.05 versus healthy patients or air-exposed ferrets; †P<0.05 versus COPD GOLD stage 2; ‡P<0.05 versus COPD GOLD stage 3, by unpaired t test for 2 groups or 1-way ANOVA followed by Tukey's post hoc testing for more than 2 groups.

FIG. 2A is a graph showing the plasma levels of total heme in mice after $Br_2$ inhalation (n=6-11). FIG. 2B is a graph showing the protein levels of bronchoalveolar lavage fluid (BALF) over the course of a 21-day period after $Br_2$ inhalation (n=9-14). FIG. 2C is a graph showing the total cell count of BALF over the course of a 21-day period after $Br_2$ inhalation (n=9-17). FIG. 2D shows peripheral lung tissue staining for α-smooth muscle actin (α-SMA) (n=5) after $Br_2$ exposure. FIG. 2E shows peripheral lung tissue staining with Masson's trichrome stain (n=5) after $Br_2$ exposure. FIG. 2F is a graph showing the quantification of collagen by measuring lung hydroxyproline levels at 14 and 21 days after $Br_2$ inhalation. Values are means±SEM. *P<0.05 versus air-exposed C57BL/6 mice by 1-way ANOVA followed by Tukey's post hoc test. Scale bars are 100 μm.

FIG. 3A is a graph-showing $Br_2$ inhalation increased lung volumes as indicated by shifting up and left of PV curves on days 14 and 21 after exposure (n=5-9). FIG. 3B shows the staining of peripheral lung tissue with hematoxylin and eosin (H&E). FIG. 3C is a graph showing the measured alveolar mean linear intercept ($L_m$) (n=5). FIG. 3D is a graph showing plasma elastase levels (n=6-10) in $Br_2$-exposed mice. FIG. 3E is a graph showing BALF elastase activity (n=7-14) in $Br_2$-exposed mice. Values are means±SEM. *P<0.05 versus air-exposed C57BL/6 mice by 1-way ANOVA followed by Tukey's post hoc test. PV curves were analyzed by 2-way ANOVA with Bonferroni's post hoc test.

FIG. 4A illustrates an immunoblot analysis of ER stress marker, Grp78/Bip (n=6-10), on days 7, 14, or 21 after exposure. FIG. 4B illustrates an immunoblot analysis of ER stress marker, phospho-PERK (n=10), on days 7, 14, or 21 after exposure. FIG. 4C illustrates an immunoblot analysis of ER stress marker, phospho-IRE1α (n=8), on days 7, 14, or 21 after exposure. FIG. 4D illustrates an immunoblot analysis of ER stress marker, ATF6 (n=8), on days 7, 14, or 21 after exposure. FIGS. 4E and 4F show that $Br_2$ exposure increased the lung expression of Grp78, phopho-PERK and the downstream transcriptional effectors of the PERK pathway ATF4 (n=7) (FIG. 4E) and CHOP (n=5-8) (FIG. 4F), 14 days after exposure. Values are means±SEM. *P<0.05 versus air-exposed C57BL/6 mice by 1-way ANOVA followed by Tukey's post hoc test.

FIGS. 5A and 5B are immunoblot analyses of lung tissue showing that salubrinal increased phospho-eIF2α levels (n=7-8) (FIG. 5A) but decreased lung CHOP levels (n=12-13) (FIG. 5B) after $Br_2$ exposure. FIGS. 5C and 5D are graphs showing salubrinal attenuated BALF protein (n=5-6) (FIG. 5C) and total cell count (n=5-6) (FIG. 5D) in $Br_2$-exposed mice. FIGS. 5E and 5F illustrate Masson's trichrome staining of lungs (FIG. 5E) and quantification of lung hydroxyproline levels (FIG. 5F) showing decreased collagen levels and lung fibrotic changes in $Br_2$-exposed mice after treatment with salubrinal. Values are means±SEM. *P<0.05 versus air+DMSO-treated mice and †$P<0.05$ versus $Br_2$+DMSO-treated mice by 1-way ANOVA followed by Tukey's post hoc test.

FIG. 6A is a graph of pressure-volume (PV) curves showing the lung volumes were increased in mice fourteen days after $Br_2$ exposure as indicated by the shifting up and left of the pressure-volume (PV) curves (n=5-6). FIG. 6B illustrates staining of peripheral lung tissue with hematoxylin and eosin (H&E) and shows airspace enlargement (n=5). FIG. 6C is a graph showing measurements of alveolar mean linear intercept ($L_m$) (n=5). Scale bars 100 μm. FIGS. 6D and 6E show salubrinal also reduced plasma elastase levels (n=10-16) (FIG. 6D) and BALF elastase activity (n=5-7) (FIG. 6E) in $Br_2$-exposed mice. Values are means±SEM. All animals were males. *$P<0.05$ versus air+DMSO-treated mice and †$P<0.05$ versus $Br_2$+DMSO-treated mice by 1-way ANOVA followed by Tukey's post hoc test. PV curves were analyzed by 2-way ANOVA with Bonferroni's post hoc test.

FIGS. 7A and 7B, are immunoblot analyses showing that $ATF4^{+/-}$ mice had lower lung ATF4 (n=6) (FIG. 7A) and CHOP levels (n=6) (FIG. 7B) compared with WT mice exposed to $Br_2$. FIGS. 7C and 7D illustrate Masson's trichrome staining (n=5) (FIG. 7C) and quantification of lung hydroxyproline levels (n=6-10) (FIG. 7D) (scale bars are 100 μm) showing increased collagen deposition primarily around airways in the WT mice compared with the $ATF4^{+/-}$ mice. FIG. 7E is a graph of lung pressure-volume (PV) curves demonstrating that $Br_2$ exposure increased lung volumes as indicated by shifting up and left of PV curve in the WT but not the $ATF4^{+/-}$ mice (n=4 for WT+air and n=5 for others). FIG. 7F is a graph showing the measurement of alveolar mean linear intercept (Lm) (n=5-6). FIGS. 7G and 7H are graphs showing plasma elastase levels (n=6-13) (FIG. 7G) and BALF elastase activity (n=6-7) (FIG. 7H). Values are means±SEM. *$P<0.05$ versus WT+air, †$P<0.05$ versus $ATF^{+/-}$+air, and ‡$P<0.05$ versus WT+$Br_2$ for FIGS. 7A and 7B; †$P<0.05$ versus WT+$Br_2$ for FIGS. 7D-7H by 1-way ANOVA followed by Tukey's post hoc test. PV curves were analyzed by 2-way ANOVA with Bonferroni's post hoc test.

FIG. 8A is an immunoblot analysis showing that the incubation of the human bronchial epithelial cells with hemin (a form of heme, 25 μM), increased the ER stress markers ATF4 and CHOP (n=3) at 6 and 24 hours after hemin challenge. FIG. 8B is a graph showing that Hpx attenuated plasma total heme levels in $Br_2$-exposed mice (n=9-24). FIGS. 8C and 8D are immunoblot analyses showing that Hpx lowered $Br_2$-induced ER stress markers, ATF4 (n=10) (FIG. 8C) and CHOP (n=11-15) (FIG. 8D), in mouse lungs 14 days after $Br_2$ exposure. FIG. 8E illustrates immunohistochemical staining of lung sections showing an increased accumulation of ATF4 and CHOP (n=4-5) (arrows showing brown stain) lining bronchioles and in the lung parenchyma in $Br_2$-exposed mice 14 days after exposure. Values are mean±SEM. All animals were males. Scale bars are 200 μm. For FIG. 8A, *$P<0.05$ versus air+saline, †$P<0.05$ versus $Br_2$+saline (1 day after), and ‡$P<0.05$ versus Br2+saline (14 days after); for FIGS. 8B and 8C, †$P<0.05$ versus Br2+saline (14 days after) by 1-way ANOVA followed by Tukey's post hoc test.

FIGS. 9A and 9B are graphs showing mouse BALF protein levels (n=5-9) (FIG. 9A) and total cell count (n=5-7) (FIG. 9B) were elevated in saline-treated mice but were significantly lower in Hpx-treated mice fourteen days after $Br_2$ exposure. FIG. 9C illustrates Hpx-treated mice had decreased lung deposition of collagen on Masson's trichrome staining (n=5-8) compared with saline-treated mice, 14 days after $Br_2$ inhalation. FIG. 9D is a graph showing lower lung hydroxyproline levels (n=5-8) in Hpx-treated mice compared with saline-treated mice, 14 days after $Br_2$ inhalation. FIG. 9E is a graph showing that Hpx reduced alveolar $L_m$ (n=5-8) (scale bars 100 μm). FIG. 9F is a graph of mouse lung pressure-volume (P-V) curves demonstrating that $Br_2$ exposure increased lung volumes, as indicated by the shifting up and left of PV curve in the saline-treated mice but not in the Hpx-treated mice (n=5-10). FIGS. 9G and 9H are graphs showing Hpx lowered plasma elastase levels (n=14-16) (FIG. 9G) and BALF elastase activity (n=10-13) (FIG. 9H) in $Br_2$-exposed mice. FIG. 9I is a Kaplan-Meier curve demonstrating that Hpx reduced mortality after $Br_2$ exposure (n=42 for $Br_2$+saline; n=20 for $Br_2$+Hpx [1 hour after]; n=17 for $Br_2$+Hpx [5 days after]). *$P<0.05$ versus air+saline and †$P<0.05$ versus $Br_2$+saline by 1-way. ANOVA followed by Tukey's post hoc test. PV curves were analyzed by 2-way ANOVA with Bonferroni's post hoc test. Overall survival was analyzed by the Kaplan-Meier method. Differences in survival were tested for statistical significance by the log-rank test.

FIG. 11A is a graph showing the measurement of $PaO_2$. FIG. 11B is a graph showing the measurement of $PaCO_2$. FIG. 11C is a graph showing the measurement of pH. FIG. 11D is a graph showing the measurement of $HCO_3^-$. Values are means±1 SEM. Each point represents a different mouse. Statistical analysis was performed by one-way analysis of variance followed by Tukey's post-hoc testing.

FIG. 12A is a graph showing the change in body weight of mice exposed to air. FIG. 12B is a graph showing the change in body weight of mice exposed to 10 ppm $COCl_2$ for 10 minutes. FIG. 12C is a graph showing the change in body weight of mice exposed to 20 ppm $COCl_2$ for 10 minutes. FIG. 12D is a graph showing Kaplan-Meyer survival curves for 10 ppm $COCl_2$ (n=20; dotted line) or 20 ppm $COCl_2$ (n=20; solid line) for 10 min (equal numbers of male and female mice). All air exposed mice were alive at 21 days post exposure. *$p=0.0006$ as compared to air or 10 ppm $COCl_2$ according to the Long-rank (Mantel-Cox) test.

FIG. 13A is a graph showing the wet/dry weight of lungs from mice 3 or 24 h post exposure to either air or 20 ppm $COCl_2$ for 10 min. FIG. 13B is a graph showing the BALF protein levels of mice 3 or 24 h post exposure to either air or 20 ppm $COCl_2$ for 10 min. FIG. 13C illustrates BALF proteins separated by SDS-PAGE (2 μl BAL). Statistical analysis was done by ANOVA with Tukey's post-test.

FIG. 14A is a graph showing the percentage of neutrophils in BALF cells in mice 24 h post exposure to either air or 20 ppm $COCl_2$ for 10 min. FIG. 14B is a graph showing the percentage of neutrophils in BALF cells in mice 24 h post exposure to either air or 20 ppm $COCl_2$ for 10 min. Means±1 SEM; n=14 air; n=13 $COCl_2$; statistical analysis by unpaired t-test. FIG. 14C shows hematoxylin and eosin staining and photos of the lungs of mice 24 h post exposure to either air or 20 ppm $COCl_2$.

FIG. 15A is a graph showing measurements of airway resistance in mice exposed to either air (n=10; black circles) or $COCl_2$ (20 ppm for 10 min; n=5; black diamonds). FIG. 15B is a graph showing measurements of elastance in mice exposed to either air (n=10; black circles) or $COCl_2$ (20 ppm for 10 min; n=5; black diamonds). Numbers are means±1 SEM; *p<0.05 (unpaired t-test). *p<0.05 by Student's t-test for the indicated levels of resistance or elastance.

FIG. 16A shows the measurement of membrane associated carbonyl adducts from RBC collected 24 h post exposure to $COCl_2$ (20 ppm, 10 min). Each lane represents a different mouse. FIG. 16B is a graph showing the quantification of carbonyl adducts. Values are means±1 SEM; Student's t-test.

FIG. 17A is a graph showing the percentage of RBC hemolysis in air and $COCl_2$ exposed mice. FIG. 17B is a graph showing total heme levels measured in the plasma of air and $COCl_2$ exposed mice using a QuantiChrom heme assay kit. FIG. 17C is a graph showing total heme levels measured in the plasma using an absorbance spectrum deconvolution. FIG. 17D is a graph showing free heme levels measured in the plasma using an absorbance spectrum deconvolution. Means±1 SEM; n=33 air and 19 for $COCl_2$. Total heme levels determined by these two methods were very similar.

FIG. 18A is a graph showing plasmenylethanolamine levels in air and $COCl_2$ exposed mice. FIG. 18B is a graph showing polyunsaturated lysophosphatidylethanolamine levels in air and $COCl_2$ exposed mice. Values are means±1 SEM. Statistical Analysis by the Student's t-test.

FIG. 19A is a graph showing plasma CFH levels in persons exposed to $Cl_2$ were higher than the age- and sex-matched human controls (n=5-6). FIGS. 19B and 19C are graphs showing $Cl_2$ exposed individuals had elevated levels of 16ClFA (n=4-5) (FIG. 19B) and 18ClFA (n=4-5) (FIG. 19C). FIG. 19D is a graph showing adult male C57BL/6 mice exposed to $Cl_2$ gas (400 ppm, 30 min) had increased levels of heme in plasma 24 h post exposure (n=9-10). Individual values and means±SEM. *P<0.05 vs. unexposed humans or air exposed mice; by unpaired t-test.

FIG. 20A is a graph showing the levels of total 16BrFA in plasma of $Br_2$ exposed mice. FIG. 20B is a graph showing the levels of free 16BrFA in plasma of $Br_2$ exposed mice. FIG. 20C is a graph showing the levels of esterified 16BrFA in plasma of $Br_2$ exposed mice. FIG. 20D is a graph showing the levels of total 18BrFA in plasma of $Br_2$ exposed mice. FIG. 20E is a graph showing the levels of free 18BrFA in plasma of $Br_2$ exposed mice. FIG. 20F is a graph showing the levels of esterified 18BrFA in plasma of $Br_2$ exposed mice. Individual values and means±SEM. *P<0.05 vs. air exposed mice, by one-way ANOVA followed by Tukey post hoc testing.

FIG. 21A is a graph showing the levels of 16BrFALD in BALF of $Br_2$ exposed mice. FIG. 21B is a graph showing the levels of total 16BrFA in BALF of $Br_2$ exposed mice. FIG. 21C is a graph showing the levels of free 16BrFA in BALF of $Br_2$ exposed mice. FIG. 21D is a graph showing the levels of esterified 16BrFA in BALF of $Br_2$ exposed mice. FIG. 21E is a graph showing the levels of 18BrFALD in BALF of $Br_2$ exposed mice. FIG. 21F is a graph showing the levels of 18BrFA in BALF of $Br_2$ exposed mice. FIG. 21G is a graph showing the levels of free 18BrFA in BALF of $Br_2$ exposed mice. FIG. 21H is a graph showing the levels of esterified 18BrFA in the BALF of $Br_2$ exposed mice. Values and means±SEM. *P<0.05 vs. air exposed mice, by one-way ANOVA followed by Tukey post hoc testing.

FIG. 22A is a graph showing the levels of 16FALD-GSH in BALF of $Br_2$ exposed mice. FIG. 22B is a graph showing the levels of 18FALD-GSH in BALF of $Br_2$ exposed mice. FIG. 22C is a graph showing the levels of 16FALD-GSH in the peripheral lung tissue of $Br_2$ exposed mice. FIG. 22D is a graph showing the levels of 18FALD-GSH in the peripheral lung tissue of $Br_2$ exposed mice. Values are means±SEM. *P<0.05 vs. air exposed mice, by one-way ANOVA followed by Tukey post hoc testing.

FIG. 23A is a graph showing the levels of 16FALD-GSH in plasma of $Br_2$ exposed mice. FIG. 23B is a graph showing the levels of 18FALD-GSH in plasma of $Br_2$ exposed mice. FIG. 23C is a graph showing the levels of 16FALD-GSH in the urine of $Br_2$ exposed mice. FIG. 23D is a graph showing the levels of 18FALD-GSH (n=4-5) (D) in the urine of $Br_2$ exposed mice. FIG. 23E is a graph showing the levels of 16FALD-GSH in the RBCs of $Br_2$ exposed mice. FIG. 23F is a graph showing the levels of 18FALD-GSH in the RBCs of $Br_2$ exposed mice. Values are means±SEM. *P<0.05 vs. air exposed mice, by one-way ANOVA followed by Tukey post hoc testing.

FIG. 24A is a graph showing the effects of brominated and chlorinated lipids on RBC hemolysis. FIGS. 24B and 24C are graphs showing the effects of brominated lipids (FIG. 24B) and chlorinated lipids (FIG. 24C) on RBC carbonylation. Individual values and means±SEM. *P<0.05 vs. untreated RBCs, †P<0.05 versus non-halogenated lipids by one-way ANOVA followed by Tukey post hoc testing.

FIG. 25A is an illustration of the LCMS base-peak chromatogram. FIG. 25B is the parent-ion spectra from the peptide peaks of interest.

FIGS. 26A and 26B illustrate the dose response of heme on short circuit current recorded from human bronchiolar epithelial cells monolayers mounted in Ussing chambers. FIG. 26C is a graph summarizing the dose response of $Na^+$ current to increasing heme concentrations. FIG. 26D is a graph showing the effects of heme on $Na^+/K^+$-ATPase function. The difference in current prior to and following ouabain addition represents the $Na^+/K^+$-ATPase (pump current).

FIG. 27A shows whole cell total current recording using the double voltage clamp technique from an oocyte 24 h post injection of human $-\alpha\beta\gamma$ ENaC. FIG. 27B shows that $Na^+$ current is inhibited by 5 μM heme in the bath. FIG. 27C is a graph showing current-voltage relationships of total currents expressed in ENaC injected oocytes following perfusion with hemin or saline. FIGS. 27D, 27E, and 27F show a comparable inhibition of whole cell total current in oocytes by amiloride (n=11). Values are means±SEM.

FIGS. 28A-28H show heme inhibits ENaC activity in AT2 cells in situ. FIG. 28A shows a typical trace exhibiting mainly the 4 pS amiloride-sensitive current (ENaC). FIG. 28B shows inhibition of ENaC activity as heme diffuses towards the patch under the pipette. FIG. 28C shows the inhibition of open probability ($P_0$) of 4 pS channel at increasing heme concentrations (0.01-1000 nM) in the pipette. FIG. 28D illustrates the rate of ENaC inhibition by increasing heme concentrations: 10 nM, 30 nM, 100 nM, 300 nM and 1 μM. FIG. 28E shows a record of AT2 channel activity in which the cation (16 pS) was very prominent. FIG. 28F shows a slow decrease of the channel's activity with time as heme reaches the membrane patch under the pipette. FIG. 28G shows the open probability of 16 pS channel at increasing heme concentration in the pipette. FIG. 28H illustrates the rate of inhibition with increasing heme concentrations. Values are means±1 SEM.

FIGS. 29A-29B show computer modeling and heme docking on ENaC. FIGS. 29A and 29B illustrate at least two heme-bonding sites located within the ENaC transmembrane pore.

FIG. 30A is a graph showing that Hpx attenuated $Br_2$ induced increase in RBC membrane protein oxidation. FIG. 30B is a graph showing that Hpx attenuated $Cl_2$ induced increase in RBC membrane protein oxidation. FIG. 30C is a graph showing that Hpx treatment prevented an increase in RBC fragility and hemolysis induced by exposure of mice to the halogen gases. Individual values and means±SEM. *$P<0.05$ vs. air exposed mice, †$P<0.05$ vs. mice exposed to $Br_2$ (FIG. 30A), $Cl_2$ (FIG. 30B), and their respective $Br_2$ or $Cl_2$ (FIG. 30C). The results were analyzed by one-way ANOVA followed by Tukey post hoc testing.

FIGS. 31A-31C represent traces exhibiting mainly the 4 pS amiloride-sensitive current (ENaC) in the air, $Br_2$, or $Br_2$+Hpx treated mice, respectively. FIG. 31D shows the quantification of open probability ($P_0$) of 4 pS channels. FIGS. 31E-31G represent traces exhibiting mainly the 16 pS amiloride-sensitive current (ENaC) in the air, $Br_2$, or $Br_2$+Hpx treated mice, respectively. FIG. 31H shows the quantification of open probability ($P_0$) of 16 pS channels. Individual values and means±SEM. (n=11). *$P<0.05$ vs. air exposed mice, †$P<0.05$ vs. mice exposed to $Br_2$ for FIGS. 31D and 31H. The results were analyzed by one-way ANOVA followed by Tukey post hoc testing.

FIG. 32A is an image of lung morphology in a normal developing mouse lung. FIG. 32B is an image of lung morphology of mice exposed to $Cl_2$. FIG. 32C is an image of lung morphology of hemopexin treated $Cl_2$ exposed mice.

FIG. 33A is an image of lung morphology in a normal developing mouse lung at the P14 stage. FIG. 33B is an image of lung morphology of mice exposed to $Cl_2$ at the P14 stage. FIG. 33C is an image of lung morphology of hemopexin treated $Cl_2$ exposed mice at the P14 stage. FIG. 34E is a graph showing mean linear intercept (MLI).

FIGS. 34A-34D show phosgene toxicity in neonatal animals. FIG. 34A is a graph showing the weight of mice exposed to air, 10 ppm of phosgene, and 20 ppm of phosgene over the course of 14 days. FIG. 34B is a graph showing airway resistance assessed by FlexiVent. FIG. 34C shows histology images of lungs of the mice at the P14 stage. FIG. 34D is a graph showing mean liner intercept (MLI).

FIG. 35A shows osmotic lysis curves of adult and neonatal RBCs subjected to gradually decreasing osmotic strength buffer. FIG. 35B is a summary of the data of NaCl concentrations causing 50 percent lysis in adult and neonatal RBCs (determined from curves shown in FIG. 35A). FIG. 35C is a graph showing plasma total heme levels in air and $Br_2$ exposed adult and neonatal mice. FIG. 35D is a graph showing HO-1 gene expression in air and $Br_2$ exposed neonatal mouse livers with or without treatment with ATG.

FIG. 37A is a graph showing that the HPX and ATG combination is more effective than HPX or ATG alone against mortality. FIG. 37B is a graph showing that administration of HPX and ATG improves arterial oxygenation of $Br_2$ exposed mice. $P<0.05$, ANOVA.

FIG. 38A is a graph showing IL-1b mRNA levels after HPX and ATG treatment. FIG. 38B is a graph showing IL-6 mRNA levels after HPX and ATG treatment. FIG. 38C is a graph showing TNFa mRNA levels after HPX and ATG treatment.

FIG. 39A is a graph showing plasma bioavailability of human hemopexin. FIG. 39B is a graph showing plasma IgM levels at different intervals post hemopexin injection.

FIG. 40A is a graph showing BALF heme levels of $Cl_2$ exposed mice and $Cl_2$ exposed mice treated with hemopexin. FIG. 40B is a graph showing BALF protein levels of $Cl_2$ exposed mice and $Cl_2$ exposed mice treated with hemopexin. FIG. 40C is a graph showing the BALF total cell count of $Cl_2$ exposed mice and $Cl_2$ exposed mice treated with hemopexin. FIG. 40D is a graph showing BALF protein levels of $COCl_2$ exposed mice and $COCl_2$ exposed mice treated with hemopexin. FIGS. 40E and 40F are Kaplan-Meier survival curves showing that hemopexin improved survival in mice exposed to $Cl_2$ (FIG. 40E) or $Br_2$ (FIG. 40F). $P<0.05$ vs $Cl_2$+saline or $Br_2$+saline.

FIG. 41A are images of bacterial colonies showing that hemopexin decreased infection in mice after $Cl_2$ or $Br_2$ exposure. FIG. 41B is a graph representing the average lung CFU of the bacteria on agar plates.

DETAILED DESCRIPTION

Definitions

Figure 1A:
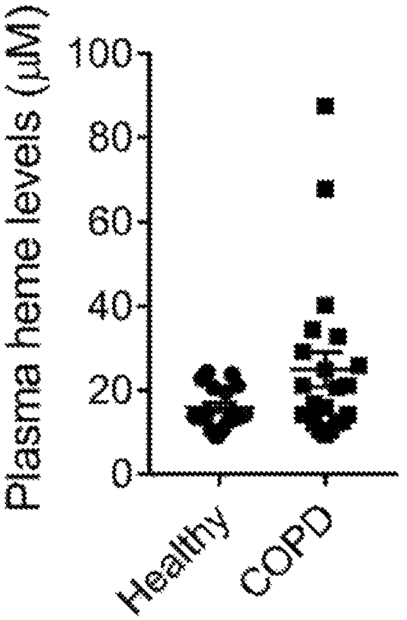
FIGS. 1A-1D show plasma heme and ER stress levels are elevated in patients with very severe COPD and in ferrets exposed to cigarette smoke.

With reference to the use of the word(s) "comprise" or "comprises" or "comprising" in the foregoing description and/or in the following claims, unless the context requires otherwise, those words are used on the basis and clear understanding that they are to be interpreted inclusively, rather than exclusively, and that each of those words is to be so interpreted in construing the foregoing description and/or the following claims.

The term "consisting essentially of" means that, in addition to the recited elements, what is claimed may also contain other elements (steps, structures, ingredients, components, etc.) that do not adversely affect the operability of what is claimed for the intended purpose stated in the claim. Such addition of other elements that do not adversely affect the operability of what is claimed for its intended purpose would not constitute a material change in the basic and novel characteristics of what is claimed.

The terms "prevention", "prevent", "preventing", "suppression", "suppress" and "suppressing" as used herein refer to a course of action (such as implanting a medical device) initiated prior to the onset of a clinical manifestation of a disease state or condition so as to prevent or reduce the severity of such clinical manifestation of the disease state or condition. Such preventing and suppressing need not be absolute to be useful.

The terms "treatment", "treat" and "treating" as used herein refers a course of action (such as implanting a medical device) initiated after the onset of a clinical manifestation of a disease state or condition so as to eliminate or reduce the severity of such clinical manifestation of the disease state or condition. Such treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method or device of the present disclosure.

Terms such as "at least one of A and B" should be understood to mean "only A, only B, or both A and B." The same construction should be applied to longer list (e.g., "at least one of A, B, and C").

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method or device of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

In this disclosure terms such as "administering", or "administration" include acts such as prescribing, dispensing, giving, or taking a substance such that what is prescribed, dispensed, given, or taken is actually contacts the patient's body externally or internally (or both). It is specifically contemplated that instructions or a prescription by a medical professional to a subject or patient to take or otherwise self-administer a substance is an act of administration.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a given value. Numerical quantities given herein are approximate unless stated otherwise, meaning that the term "about" or "approximately" can be inferred when not expressly stated.

The term "therapeutically effective amount" as used herein refers to an amount of a compound, either alone or as a part of a pharmaceutical composition, that is capable of having any detectable, positive effect on any symptom, aspect, or characteristics of a disease state or condition. Such effect need not be absolute to be beneficial.

The term "hemopexin (Hpx) compound" refers to at least one of: Hpx, a prodrug of Hpx, a pharmaceutically acceptable salt of at least one of the foregoing, and an ester of at least one of the foregoing. Where reference is made to the administration of an Hpx compound, it should be understood to include the administration of any compound that is converted to Hpx in the body after administration.

The term "prodrug" as used herein includes functional derivatives of a disclosed compound which are readily convertible in vivo into the required compound. Thus, in the methods of treatment of the present disclosure, the term "administering" shall encompass the treatment of the various disease states/conditions described with the compound specifically disclosed or with a prodrug which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The term "pharmaceutically acceptable salts" as used herein includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent.

Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

Hemopexin

Hemopexin (Hpx) is a plasma glycoprotein that binds heme with high affinity. Hpx is an acute phase protein that transports heme from the plasma to the liver and may be involved in protecting cells from oxidative stress. It is encoded by the HPX gene in humans and other mammals. The HPX gene is conserved in chimpanzee, Rhesus monkey, dog, cow, mouse, rat, chicken, zebrafish, and frog. Hpx consists of a single polypeptide chain of 439 amino acids residues with six intrachain disulfide bridges and has a molecular mass of approximately 63 kD. The amino-terminal threonine residue is blocked by an O-linked galactosamine oligosaccharide, and the protein has five glucosamine oligosaccharides N-linked to the acceptor sequence Asn-X-Ser/Thr. The 18 tryptophan residues are arranged in four clusters, and 12 of the tryptophans are conserved in homologous positions. The complete primary structure of Hpx was elucidate by Takahashi et al., *Proc. Nat'l Acad. Sci. USA,* 82:73-75, January 1985, and the teaching of this structure is incorporated herein by reference as necessary for one of ordinary skill in the art to make and use any inventions in this disclosure. Hemopexin is commercially available from multiple sources, for example from Sigma-Aldrich of St. Louis, Missouri, USA.

In the methods and compositions disclosed herein, Hpx may be administered at an effective dosage, for example 0.4-100 mg/kg. In some embodiments of such methods and compositions, the dosage is 0.8-50 mg/kg, or 2-5 mg/kg. In more specific embodiments of such methods and compositions, the dosage may be 1, 2, 3, 4, 5, 6, 7, 8, 9, or 10 mg/kg. When an Hpx compound other than Hpx is administered, it may be administered at a level equivalent to the Hpx dosages described above. Administration may be by any suitable route, for example by the intramuscular route.

Methods of Treatment and Prevention

Methods are provided using an Hpx compound to treat or prevent several conditions. In a general embodiment, an Hpx compound is used to treat a form of pulmonary injury that is not previously known to be associated with free heme in the patient. In a more specific embodiment, the pulmonary injury is one that is not associated with pulmonary free heme. Specific forms of pulmonary injury contemplated include halogenated gas exposure, chlorine gas ($Cl_2$) exposure, phosgene gas ($COCl_2$) exposure, bromine gas ($Br_2$) exposure, smoke inhalation, tobacco smoke inhalation, chronic obstructive pulmonary disorder, emphysema, bronchitis (including chronic and acute bronchitis), exposure to air pollution, exposure to toxic fumes, bacterial infection, *Pseudomonas aeruginosa* infection, *Streptococcus pneumonia* infection, and any combination of two or more of the foregoing.

Halogenated Gasses

As described in more detail in the examples below, it has been discovered that Hpx is effective to reduce the negative effects of halogenated gasses not previously understood to be associated with free heme in the lungs. It has been specifically observed that $COCl_2$ causes red blood cell damages and the release of hemin in the lungs. I one embodiment of the method an effective amount of An Hpx compound is administered to a subject for the treatment or prevention of $COCl_2$ injury. It has also been observed in the animal studies below that $Cl_2$ exposure results in red blood cell appearing in the alveoli, and that treatment with Hpx improves the conditions of animals exposed to $Cl_2$. In another embodiment of the method an effective amount of An Hpx compound is administered to a subject for the treatment or prevention of $Cl_2$ injury. Further embodiments of the method involve treating or preventing injury caused by either or both of $COCl_2$ and $Cl_2$ injury in conjunction with other causes of pulmonary injury.

Neonatal Pulmonary Injury

The studies in the examples below reveal that neonatal red blood cells are more vulnerable to $Br_2$-induced injury and that neonatal animals suffer high rates of mortality from 012 and $COCl_2$ exposure; without wishing to be bound by any single hypothesis, it is believed neonatal RBCs are damaged by lipid adducts of $Br_2$. A general embodiment of the method involves administering an effective amount of an Hpx compound to a neonate to treat and prevent pulmonary injury. The pulmonary injury may be at least partially the result of exposure to a chemical agent, such as a halogenated gas. Such halogenated gasses may include $Cl_2$, $Br_2$, and phosgene. In alternative embodiments of the method, the pulmonary injury is at least partially the result of at least one of: tobacco smoke exposure, chronic obstructive pulmonary disorder, emphysema, and chronic bronchitis.

Chronic Obstructive Pulmonary Disease

It has also been discovered that Hpx reduces the severity of chronic obstructive pulmonary disease (COPD). A general embodiment of the method involves administering an effective amount of An Hpx compound to a subject to treat and prevent COPD. The COPD may manifest in various forms, such as emphysema or chronic bronchitis (or both). COPD can have numerous causes, including tobacco smoking, polluted air, and toxic fumes (e.g., as in the workplace). Some embodiments of the method comprising administering An Hpx compound to the subject after the subject has been exposed to such causes of COPD, or prior to an expected exposure. In a specific embodiment An Hpx compound is administered to a subject who has been exposed to tobacco smoke, or who is expected to be exposed to tobacco smoke.

Lung Infections

It has been discovered that the severity of bacterial infections incident to pulmonary injury can be reduced with Hpx. A general embodiment of the method comprises administering an effective amount of an Hpx compound to a subject who has suffered pulmonary injury associated with exposure to a chemical agent. Administration may occur prior to, during, or subsequent to the onset of infection. The chemical agent may be a halogenated gas, such as $Br_2$, $Cl_2$, or phosgene. The method may be used to treat bacteria infections generally. In specific embodiments, the causative agent of the bacterial infection is *Pseudomonas aeruginosa, Streptococcus pneumonia*, or a co-infection of the foregoing.

Immune Cell Impairment

It has been discovered that that the severity of immune cell impairment by chemical agents can be reduced by the administration of an Hpx compound. A general embodiment of the method comprises administering an effective amount of an Hpx compound to a subject who has been exposed to a chemical agent or is expected to so be so exposed, the effective amount being effective to treat or prevent the resulting impairment of immune function in the subject. The immune cell in question lymphocytes may include a T-cell, B-cell, NK cell, neutrophil, a monocytes, or a macrophages. In specific embodiments of the method the immune cell is a macrophage or a neutrophil. The method may operate on multiple cell types simultaneously. The immune cell may have been exposed to or at risk of exposure to acellular heme, such as acellular heme resulting from exposure to a halogenated gas. Common examples of such halogenated gasses include $Cl_2$, $Br_2$, phosgene, or a combination of any of the foregoing.

Combined with Aurothioglucose

It has been unexpectedly discovered that Hpx acts synergistically with aurothioglucose (ATG) in reducing the severity of pulmonary injury. Aurothiogldcose is synonym for gold(1+);(3R,4S,5S,6R)-3,4,5-trihydroxy-6-(hydroxymethyl) oxane-2-thiolate ($C_6H_{11}AuO_5S$), once sold under the trade name Solganal. It was used historically to treat rheumatoid arthritis. It has the structure shown below:

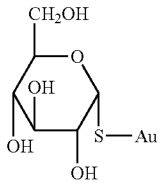

In the context of this disclosure an "ATG compound" refers to at least one of: ATG, a prodrug of ATG, a pharmaceutically acceptable salt of at least one of the foregoing, and an ester of at least one of the foregoing. Where reference is made to the administration of an ATG compound, it should be understood to include the administration of any compound that is converted to ATG in the body after administration.

A method is provided for treating or preventing pulmonary injury associated with acellular heme in a subject in need thereof, the method comprising: administering an effective amount of an Hpx compound to the subject; and administering an effective amount of an ATG compound to the subject. The dosage of Hpx may be any disclosed above as suitable for treating or preventing pulmonary injury. The dosage of ATG may follow earlier recommendations for treating arthritis, which involved adult dosages of 10 mg, 25 mg, and 50 mg progressively. Recommended pediatric dosages included 0.25 mg/kg as an initial dose, and later dosages of 0.50, 0.75, and 1 mg/kg on a weekly basis. Based on animal studies described below, ATG may be administered to 2.5-250 mg/kg for pulmonary injury. In more specific embodiments of the method, ATG is administered at 5-125 mg/kg, 12.5-50 mg/kg, and 25 mg/kg. Administration may be by various routes, including the intramuscular route. When an ATG compound other than ATG is administered, it may be administered at a level equivalent to the ATG dosages described above.

Acellular-Heme Injury

The pulmonary injury may of a type that is associated with acellular heme. In some embodiments of the method the pulmonary injury results from exposure to a chemical agent, such as a halogenated gas. Examples of such halogenated gasses include $Br_2$, $Cl_2$, and phosgene. In further embodiments the pulmonary injury results from exposure to tobacco smoke, air pollution, or toxic fumes.

Salubrinal Administration

Salubrinal (9 (2E)-3-Phenyl-N-[2,2,2-trichloro-1-[[(8-quinolinylamino) thioxomethyl]amino]ethyl]2-propenamide) is a selective Inhibitor of eIF2α (eukaryotic translation initiation factor 2 α-subunit) dephosphorylation, inhibiting global protein translation. It has the following structure:

11

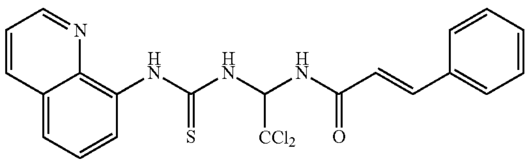

Salubrinal is a specific inhibitor of ER Stress induced apoptosis. Salubrinal maintains protein phosphorylation in order to offer protection against from the adverse effects of endoplasmic reticulum stress. Salubrinal prevents collagenase-mediated articular cartilage damage promoting down-regulation of matrix metalloproteinase 13.

It has been found that salubrinal is effective against pulmonary injury. A method of treating or preventing pulmonary dysfunction in a subject in need thereof is provided, the method comprising administering an effective amount of a salubrinal compound to the subject. In the context of this disclosure a "salubrinal compound" refers to at least one of: salubrinal, a prodrug of salubrinal, a pharmaceutically acceptable salt of at least one of the foregoing, and an ester of at least one of the foregoing. Where reference is made to the administration of a salubrinal compound, it should be understood to include the administration of any compound that is converted to salubrinal in the body after administration.

The pulmonary dysfunction may be associated with one or more of endoplasmic reticulum (ER) stress, airway fibrosis, and emphysema. In some embodiments of the method the pulmonary dysfunction is associated with exposure to a chemical agent. In more specific embodiments of the method the chemical agent is a halogenated gas, such as $Cl_2$, $Br_2$, and COCl. In a specific embodiment of the method the halogenated gas is $Br_2$.

Salubrinal may be administered in a therapeutically effective amount, effective to reduce the effects of the pulmonary injury. In some embodiments of the method the improved effects are one or more of: increased lung phosphorylation of elf2α, decreased C/EBP homologous protein (CHOP) lower bronchoalveolar lavage fluid (BALF) protein, lower BALF cell count, decreased lung collagen, decreased lung fibrotic levels, decreased growth injury-induced (e.g., $Br_2$ induced) lung volume, and attenuation of alveolar $L_m$.

The therapeutically effective amount of salubrinal may be expressed as a function of body weight. Some embodiments of the method employ 0.1-10 mg/kg salubrinal. Further embodiments employ at least 0.1, 0.2, 0.3, 0.4, 0.5, 0.6, 0.7, 0.8, 0.9, 1, 2, 3, 4, 5, 6, 7, 9, or 10 mg/kg salubrinal. Further embodiments employ at most 0.1, 0.2, 0.3, 0.4, 0.5, 0.6, 0.7, 0.8, 0.9, 1, 2, 3, 4, 5, 6, 7; 9, or 10 mg/kg salubrinal. Still further embodiments employ ranges from 0.1-9, 0.2-8, 0.3-7, 0.4-6, 0.5-5, 0.6-4, 0.7-3, 0.8-2, and 0.9-1.1 mg/kg salubrinal. In a specific embodiment salubrinal is administered at about 1 mg/kg. Administration may be by any suitable route, including intraperitoneal. The course of treatment may involve periodic dosages. Such dosages may be administered once per week, once every other day, once per day, twice per day, three times per day, four times per day, five times per day, six times per day, etc. In a specific embodiment the dosage is given once per day. When a salubrinal compound other than salubrinal is administered, it may be administered at a level equivalent to the salubrinal dosages described above.

Figure 46:
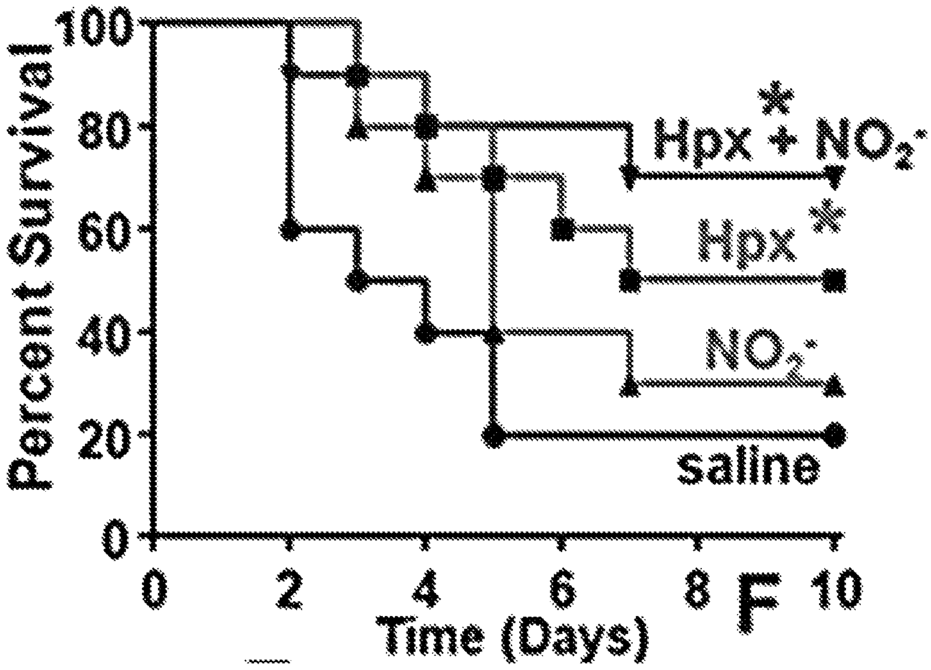
FIG. 46 is a graph showing survivorship of male C57bl/6 mice exposed to $Br_2$ (600 ppm, 45 min) and then 60 min after administered IM nitrite (10 mg/kg) or hemopexin (4 μg/g BW), or both, and survival was assessed over 10 days. Shown are Kaplan Meier curves. *$p<0.05$ relative to saline, n=10.

A shown in FIG. 46, and as further explained in the examples below, it has been discovered that the co-administration of Hpx with nitrite produces superior results to the administration of either agent along. A method of treating or preventing pulmonary injury in a subject is provided by co-administering an Hpx compound and a nitrite compound in effective amounts. The Hpx compound can be any that are disclosed as suitable in the methods above. The nitrite compound may be any suitable form, including at least one of nitrite, nitrous acid, a prodrug of nitrite, a pharmaceutically acceptable salt of at least one of the foregoing, and an ester of at least one of the foregoing. The pulmonary injury to be treated by the coadministration of Hpx and nitrite may be, for example, injury resulting from or associated with $Br_2$ gas exposure (as demonstrated in the example below). In further embodiments of the method the pulmonary injury may be one or a combination of exposure to a halogenated gas, exposure to $Cl_2$, exposure to phosgene exposure to smoking, exposure to air pollution, and exposure to toxic fumes.

The effective amount of nitrite may be 10 mg/kg body weight of the intended subject (μg/g), as demonstrated in the example below. In further embodiments of the method the effective amount of nitrite is about 1-100 mg/kg. In still further embodiments of the method the effective amount of nitrite is about 5-50 mg/kg. In still further embodiments of the method the effective amount of nitrite is about 7.5-25 mg/kg. In still further embodiments of the method the effective amount of nitrite is 9-11 mg/kg.

Pharmaceutical Compositions

Pharmaceutical compositions of Hpx compounds, ATG compounds, and salubrinal compounds are provided for the various uses described above. In one embodiment, such compounds are in the form of compositions, such as but not limited to, pharmaceutical compositions. A general embodiment of the pharmaceutical composition comprises two or more of an Hpx compound, an ATG compound, a salubrinal compound, and a nitrite compound. More specific embodiments may contain: an Hpx compound and an ATG compound; an Hpx compound and a salubrinal compound; an ATG compound and a salubrinal compound; an Hpx compound, an ATG compound, and a salubrinal compound; an Hpx compound and a nitrite compound; an ATG compound and a nitrite compound; an Hpx compound, a salubrinal compound, and a nitrite compound; an ATG compound, a salubrinal compound, and a nitrite compound; or an Hpx compound, an ATG compound, a salubrinal compound and a nitrite compound. The compositions disclosed may also include a pharmaceutically acceptable carrier. Any of the foregoing compounds may be present in a pharmaceutically effective amount, such as any suitable amount disclosed above. Examples of such carriers and methods of formulation may be found in Remington: The Science and Practice of Pharmacy (20th Ed., Lippincott, Williams & Wilkins, Daniel Limmer, editor). To form a pharmaceutically acceptable composition suitable for administration, such compositions will contain a therapeutically effective amount of a compound(s).

The pharmaceutical compositions of the disclosure may be used in the treatment and prevention methods of the present disclosure. Such compositions are administered to a subject in amounts sufficient to deliver a therapeutically effective amount of the compound(s) so as to be effective in the treatment and prevention methods disclosed herein. The therapeutically effective amount may vary according to a variety of factors such as, but not limited to, the subject's condition, weight, sex and age. Other factors include the mode and site of administration. The pharmaceutical compositions may be provided to the subject in any method known in the art. Exemplary routes of administration include, but are not limited to, subcutaneous, intravenous, topical, epicutaneous, oral, intraosseous, intramuscular, intranasal and pulmonary. The compositions of the present disclosure may be administered only one time to the subject or more than one time to the subject. Furthermore, when the compositions are administered to the subject more than once, a variety of regimens may be used, such as, but not limited to, one per day, once per week, once per month or once per year. The compositions may also be administered to the subject more than one time per day. The therapeutically effective amount of the nucleic acid molecules and appropriate dosing regimens may be identified by routine testing in order to obtain optimal activity, while minimizing any potential side effects. In addition, co-administration or sequential administration of other agents may be desirable.

The compositions of the present disclosure may be administered systemically, such as by intravenous administration, or locally such as by subcutaneous injection or by application of a paste or cream.

The compositions of the present disclosure may further comprise agents which improve the solubility, half-life, absorption, etc. of the compound(s). Furthermore, the compositions of the present disclosure may further comprise agents that attenuate undesirable side effects and/or or decrease the toxicity of the compounds(s). Examples of such agents are described in a variety of texts, such a, but not limited to, Remington: The Science and Practice of Pharmacy (20th Ed., Lippincott, Williams & Wilkins, Daniel Limmer, editor).

The compositions of the present disclosure can be administered in a wide variety of dosage forms for administration. For example, the compositions can be administered in forms, such as, but not limited to, tablets, capsules, sachets, lozenges, troches, pills, powders, granules, elixirs, tinctures, solutions, suspensions, elixirs, syrups, ointments, creams, pastes, emulsions, or solutions for intravenous administration or injection. Other dosage forms include administration transdermally, via patch mechanism or ointment. Further dosage forms include formulations suitable for delivery by nebulizers or metered dose inhalers. Any of the foregoing may be modified to provide for timed release and/or sustained release formulations.

In the present disclosure, the pharmaceutical compositions may further comprise a pharmaceutically acceptable carrier. Such carriers include, but are not limited to, vehicles, adjuvants, surfactants, suspending agents, emulsifying agents, inert fillers, diluents, excipients, wetting, agents, binders, lubricants, buffering agents, disintegrating agents and carriers, as well as accessory agents, such as, but not limited to, coloring agents and flavoring agents (collectively referred to herein as a carrier). Typically, the pharmaceutically acceptable carrier is chemically inert to the active compounds and has no detrimental side effects or toxicity under the conditions of use. The pharmaceutically, acceptable carriers can include polymers and polymer matrices. The nature of the pharmaceutically acceptable carrier may differ depending on the particular dosage form employed and other characteristics of the composition.

For instance, for oral administration in solid form, such as but not limited to, tablets, capsules, sachets, lozenges, troches, pills, powders, or granules, the compound(s) may be combined with an oral, non-toxic pharmaceutically acceptable inert carrier, such as, but not limited to, inert fillers, suitable binders, lubricants, disintegrating agents and accessory agents. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, and the like. Disintegrators include, without limitation, starch, methyl cellulose, agar, bentonite, xanthum gum and the like. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid as well as the other carriers described herein. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

For oral liquid forms, such as but not limited to, tinctures, solutions, suspensions, elixirs, syrups, the nucleic acid molecules of the present disclosure can be dissolved in diluents, such as water, saline, or alcohols. Furthermore, the oral liquid forms may comprise suitably flavored suspending or dispersing agents such as the synthetic and natural gums, for example, tragacanth, acacia, methylcellulose and the like. Moreover, when desired or necessary, suitable and coloring agents or other accessory agents can also be incorporated into the mixture. Other dispersing agents that may be employed include glycerin and the like.

Formulations suitable for parenteral administration include aqueous and non-aqueous, isotonic sterile injection solutions, which can contain anti-oxidants, buffers, bacteriostats, and solutes that render the formulation isotonic with the blood of the patient, and aqueous and non-aqueous sterile suspensions that can include suspending agents, solubilizers, thickening agents, stabilizers, and preservatives. The compound(s) may be administered in a physiologically acceptable diluent, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as, but not limited to, a soap, an oil or a detergent, suspending agent, such as, but not limited to, pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include polyethylene sorbitan fatty acid esters, such as sorbitan monooleate and the high molecular weight adducts of ethylene oxide with a hydrophobic base, formed by the condensation of propylene oxide with propylene glycol, oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkylbeta-aminopropionates, and 2-alkylimidazoline quaternary ammonium salts, and (e) mixtures thereof.

Suitable preservatives and buffers can be used in such formulations. In order to minimize or eliminate irritation at the site of injection, such compositions may contain one or more nonionic surfactants having a hydrophile-lipophile balance (HLB) of from about 12 to about 17.

Topical dosage forms, such as, but not limited to, ointments, creams, pastes, emulsions, containing the nucleic acid molecule of the present disclosure, can be admixed with a variety of carrier materials well known in the art, such as, e.g., alcohols, aloe vera gel, allantoin, glycerine, vitamin A and E oils, mineral oil, PPG2 myristyl propionate, and the like, to form alcoholic solutions, topical cleansers, cleansing creams, skin gels, skin lotions, and shampoos in cream or gel formulations. Inclusion of a skin exfoliant or dermal abrasive preparation may also be used. Such topical preparations may be applied to a patch, bandage or dressing for transdermal delivery or may be applied to a bandage or dressing for delivery directly to the site of a wound or cutaneous injury.

The compound(s) of the present disclosure can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Such liposomes may also contain monoclonal antibodies to direct delivery of the liposome to a particular cell type or group of cell types.

The compound(s) of the present disclosure may also be coupled with soluble polymers as targetable drug carriers. Such polymers can include, but are not limited to, polyvinylpyrrolidone, pyran copolymer, polyhydroxypropylmethacryl-amidephenol, polyhydroxyethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

EXAMPLES

Example 1: Heme Scavenging Reduces Pulmonary Endoplasmic Reticulum Stress, Fibrosis, and Emphysema In this working example, the molecular basis for heme-induced chronic lung injury is provided. Elevated plasma heme was found in chronic obstructive pulmonary disease (COPD) (GOLD stage 4) patients and also in a ferret model of COPD secondary to chronic cigarette smoke inhalation. A rodent model of chronic lung injury was developed, where C57BL/6 mice were exposed to the halogen gas, bromine ($Br_2$) (400 ppm, 30 minutes), and returned to room air resulting in combined airway fibrosis and emphysematous phenotype, as indicated by high collagen deposition in the peribronchial spaces, increased lung hydroxyproline concentrations, and alveolar septal damage. These mice also had elevated pulmonary endoplasmic reticulum (ER) stress as seen in COPD patients; the pharmacological or genetic diminution of ER stress in mice attenuated $Br_2$-induced lung changes. Moreover, treating mice with the heme-scavenging protein, hemopexin, reduced plasma heme, ER stress, airway fibrosis, and emphysema.

Materials and Methods

Human subjects. Adult participants were recruited to this observational cohort through the UAB Lung Health Center. Demographic information and smoking history were recorded, pre- and post-bronchodilator spirometry was conducted on all participants according to the American Thoracic Society/European Respiratory Society (ATS/ERS) guidelines [1], and phlebotomy was performed. Participants were categorized as COPD based on the ratio of postbronchodilator forced expiratory volume in 1 second to forced vital capacity (FEV1/FVC) less than 0.70 and the severity of airflow limitation (i.e., GOLD 1-4, with GOLD 4 indicating very severe airflow obstruction) [2]. Samples were processed, aliquoted, and stored at −80° C. using Freezerworks Sample Inventory Management software (Dataworks Development, Inc.). No samples had undergone freeze-thaw cycles prior to use in the study.

Animals. Adult male C57BL/6 mice (20-25 g) were purchased from Charles River, non-Frederick/NCI. C57BL/6 genetic background-based ATF4+/− knockout mice were a gift from Marina Gorbatyuk, University of Alabama at Birmingham (UAB), and have a normal appearance and organ morphology. The genotyping of ATF4+/− mice was performed using forward primers: ATATTGCTGAAGAGCTTGGCGGC (SEQ ID NO: 1) for the Neo allele and AGCAAAACAAGACAGCAGCCACTA (SEQ ID NO: 2) for the WT allele and a common reverse primer GTTTCTACAGCTTCCTCCACTCTT (SEQ ID NO: 3) for both alleles. All mice were raised under a 12-hour dim light/12-hour dark cycle with access to a standard diet and tap water ad libitum. A euthanasia protocol based on i.p. injections of ketamine and xylazine was used in the study for mice to minimize pain and distress.

Cigarette smoke exposure in ferrets. Outbred WT ferrets (*Mustela* putorius furo, females [0.6-0.8 kg BW], males [1.2-2.0 kg BW]) were procured from Marshall BioResources. After matching for age and sex, ferrets were randomizedto receive whole cigarette smoke exposure or air control groups for, 6 months. Following a brief training period, ferrets were acclimatized to customize-designed male and female nose-only exposure tubes and a 36-port plenum connected to smoke output. Ferrets were exposed to two 60-minute sessions of smoke from 3R4F research cigarettes (University of Kentucky) for 5 days/week for 6 months as described previously [3].

Exposure to $Br_2$. Mice were exposed to $Br_2$ gas (400 ppm) in a cylindrical glass chamber for 30 minutes, as previously described for chlorine gas [4-5]. Control mice were exposed to room air in the same experimental conditions as $Br_2$-exposed mice. Exposures were performed with 2 mice in the same chamber at any one time, and all exposures were performed between 6:00 am and 12:00 μm. Tanks were replaced when the pressure in the tanks reached 500 psi. In each case, immediately following exposure, mice were returned to room air.

Hpx and salubrinal administration. In some experiments starting at 1 hour after $Br_2$ exposure, mice were treated daily with either salubrinal (SML0951; Sigma-Aldrich), an ER stress inhibitor, dissolved in DMSO or control vehicle (DMSO) for 13 consecutive days at the dose of 1 mg/kg BW by i.p. injection. In other experiments, mice were treated with a single i.p. injection of Hpx (product no. 16-16-080513-LEL; Athens Research and Technology) dissolved in normal saline at the dose of 4 μg/g BW, either 1 hour or 5 days after $Br_2$ exposure and mice were sacrificed and used for experiments on the 14th day after exposure.

Assessment of respiratory mechanics. PV curves with constant increasing pressure (PVr-P) were assessed in mice anesthetized with pentobarbital (50 mg/kg i.p.; Vortech Pharmaceuticals), paralyzed with pancuronium (4 mg/kg i.p.; Gensia Sicor Pharmaceuticals), intubated, connected to an FX-1 module of the FlexiVent (SCIREQ), and ventilated at a rate of 160 breaths per minute at a tidal volume of 0.2 ml with a positive end-expiratory pressure of 3 $cmH_2O$. Each time before performing PV-loop perturbations, a total lung capacity perturbation (TLC) was carried out to normalize the lungs. PVr-P perturbations were performed until 3 acceptable measurements (coefficient of determination [COD]>0.95) were recorded in each subject, of which an average was calculated. Raw data from the PVr-P perturbation were used to reconstruct PV curves. Lung compliance (C, $\Delta V/\Delta P$) was derived from the PV curves on the deflation (upper) limb between lung pressures of 7 and 11.4 $cmH_2O$ as described previously [6]. When measured under closed-chest conditions, this variable reflects the intrinsic elastic properties of the respiratory system (i.e., lung+chest wall) at rest. Estimate of inspiratory capacity is the upper bounds estimate of the difference between total lung capacity and zero volume.

Histological analysis and Masson's trichrome staining of mouse lung. Lung tissues were removed and fixed in 70% alcoholic formalin for 24 hours and dehydrated in 70% ethanol before embedding in paraffin. Paraffin-embedded tissues were cut into 4-μm sections, deparaffinized, and rehydrated using CitriSolv (d-limonene-based solvent) and isopropanol, respectively. The sections were stained for ATF4 (11815S, Cell Signaling Technology), CHOP (2895, Cell Signaling Technology), with H&E, or with Masson's trichrome [7]. H&E-stained sections were used to assess $L_m$, which is widely accepted as an indicator of the presence of emphysema. $L_m$ was measured by dividing the total length of lines drawn across the 20 randomly selected lung fields by number of intercepts with alveolar septum at ×200 magnification. Alveoli number was determined by the number of measurements made for the $L_m$. Trichrome-stained lung section images were captured using a Leica DMI 6000 B microscope.

BALF analysis. Mice were euthanized with an i.p. injection of ketamine and xylazine (100 and 10 mg/kg body weight, respectively). The lungs were lavaged, and the recovered lavage fluid was centrifuged immediately at 3,000 g for 10 minutes to pellet the cells. Supernatants were used for protein analysis using the Pierce BCA Protein Assay (product no. 23225; Thermo Scientific, Rockford, IL). Pelleted cells were counted using a Neubauer hemocytometer and then stained using a 2-stain set consisting of eosin Y and a solution of thiazine dyes for differential counts [8].

Plasma heme assay. Heme levels were measured in plasma samples using the QuantiChrom heme assay kit (product no. DIHM-250; BioAssay Systems), according to the manufacturer's instructions.

Plasma Hpx measurement. Plasma levels of endogenous mouse Hpx levels were measured in mice using an ELISA kit (product no. GWB-D5D320; GenWay Biotech, Inc.) according to the manufacturer's instructions. Similarly, plasma levels of human Hpx were measured in mice after injection of purified human Hpx using an ELISA kit (product no. GWB-4B6D1A [40-374-130039]; GenWay Biotech, Inc.) according to the manufacturer's instructions.

Hydroxyproline quantification. Hydroxyproline level was measured by using a hydroxyproline assay kit (MAK008, Sigma-Aldrich). Briefly, 20 mg of whole lung tissue disrupted in liquid nitrogen was hydrolyzed for 3 hours in 12N HCl at 120° C. After cooling down for 20 minutes, 30 μl from each sample was transferred to a 96-well plate and evaporated at 60° C. overnight. Hydroxyproline level was measured in these samples according to the manufacturer's instructions.

Measurement of elastase levels and activity. Neutrophil elastase levels in plasma samples were measured by using a standard kit (DY4517-05, Mouse Neutrophil Elastase DuoSet ELISA, R&D Systems). Elastase activity was measured in the BALF samples by using an EnzChek Elastase Assay kit (E12056, Molecular Probes). One unit of elastase activity is defined as the amount of enzyme required to solubilize 1 mg of elastin in 20 minutes at pH 8.8 and 37° C. BALF total elastase levels could not be detected due to low sensitivity of the assay.

Assessment of ER stress. ER stress was analyzed by measuring Grp78 using a Grp78/Bip ELISA kit (ADI-900-214, Enzo Life Sciences) according to the manufacturer's instructions. Immunoblot was performed using primary antibodies at 1:1,000 dilution against CHOP (2895S), ATF4 (11815S), total IRE1α (3294S), p-PERK (3179S), p-eIF2α (9721S), total eIF2α (9722S) (all Cell Signalling Technology); ATF6 (sc22799), total PERK (sc13073), Grp78 (sc13968) (all Santa Cruz Biotechnology); and p-IRE1α (NB100-2323, Novus Biologicals) as described previously [8]. Bands were detected by a chemiluminescent HRP substrate (Millipore). Protein loading was normalized by reprobing the membranes with an antibody specific for β-actin (Sigma-Aldrich).

Cell culture. HBECs were a gift from Kevin Harrod at UAB and were maintained in Bronchial Epithelial Cell Basal Medium (Lonza). Immediately before exposure to hemin or $Br_2$, culture media were replaced with phenol red-free culture media. For $Br_2$ exposure, cells were placed in a glass chamber inside a water-jacketed incubator maintained at 37° C. and exposed to 100 ppm $Br_2$ for 10 minutes. The concentration of $Br_2$ in the chamber was measured continuously with an Interscan Corp. (model RM70-20.0 m) $Br_2$ detector. After exposure, cells were placed in a humidified incubator with air and 5% $CO_2$ at 37° C. for 6 or 24 hours.

Statistics. Statistical analysis was performed using GraphPad Prism version 7 for Windows. The mean±SEM was calculated in all experiments, and statistical significance was determined by unpaired t test for 2 groups or 1-way ANOVA followed by Tukey's post hoc testing for more than 2 groups. PV curves were analyzed by 2-way ANOVA and Bonferroni's post hoc test. Overall survival was analyzed by the Kaplan-Meier method. Differences in survival were tested for statistical significance by the log-rank test. P less than 0.05 was considered significant.

Study approval. Adult participants were recruited to this observational cohort through the UAB Lung Health Center. The study was approved by the UAB Institutional Review Board (Birmingham, AL; IRB Protocol X170301002). All animal care and experimental procedures were approved by the Institutional Animal Care and Use Committee at the UAB (Animal Protocol number: 20761).

Results

Figure 1B:
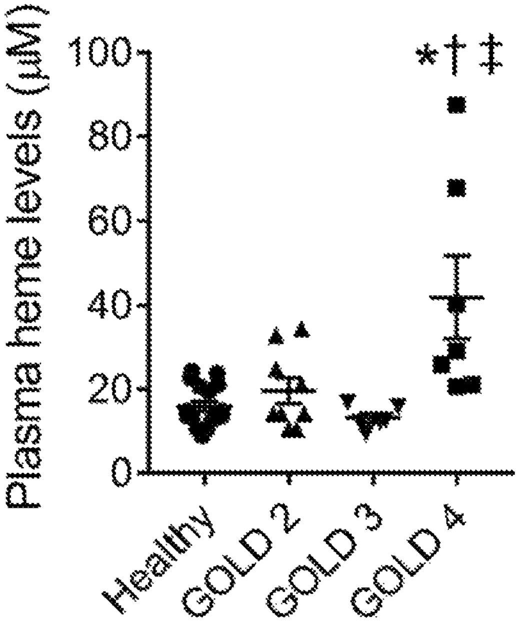
Figure 1C:
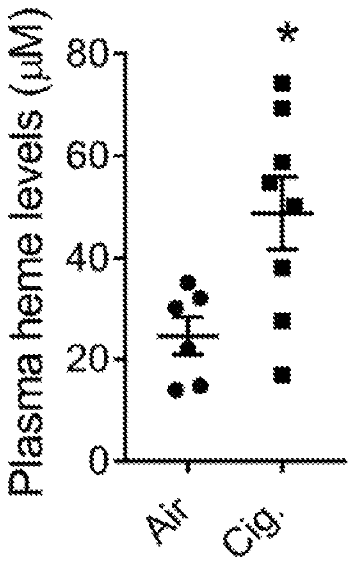
Figure 1D:
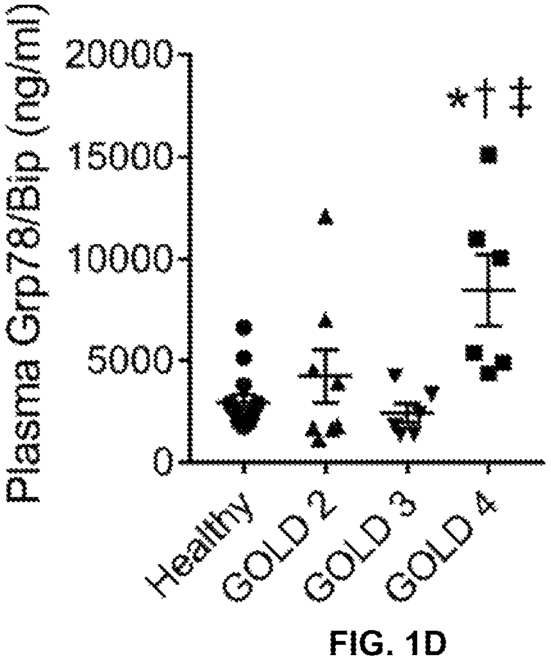

Plasma heme and ER stress is elevated in patients with severe COPD and in a ferret model of COPD. Total heme levels were measured in the plasma of COPD patients and their healthy counterparts. Demographic and clinical data for these patients is shown in Table 1 below. As shown in FIG. 1A, total heme levels were not significantly higher in COPD patients compared with the healthy individuals. However, as shown in FIG. 1B, heme levels were significantly elevated in very severe COPD patients (Global Initiative for Chronic Obstructive Lung Diseases, GOLD stage 4) compared to never-smokers and to those with mild-to-moderate COPD (GOLD stages 2 and 3). Plasma heme levels were also significantly higher in ferrets exposed to 60 minutes of smoke from 3R4F research cigarettes, twice daily for 6 months, which induced emphysema and attenuated lung function (FIG. 1C). Patients with COPD (GOLD stage 4) had significantly elevated levels of ER stress marker Grp78/Bip (FIG. 1D), a master regulator of the UPR.

TABLE 1

Demographic and clinical data of COPD patients

| | Total (n = 40) | Non-COPD (n = 18) | COPD (n = 22) | P value |
|---|---|---|---|---|
| Age in years | 59 ± 9 | 56 ± 12 | 61 ± 7 | 0.13 |
| White race | 17 (43%) | 6 (33%) | 11 (50%) | 0.06 |
| Male sex | 18 (45%) | 5 (28%) | 13 (59%) | 0.35 |
| FEV1 (liters) | 1.85 ± 0.80 | 2.37 ± 0.82 | 1.42 ± 0.45 | <0.001 |
| FEV1, percentage predicted | 67 ± 21 | 86 ± 12 | 52 ± 13 | <0.001 |
| FVC (liters) | 2.96 ± 0.90 | 3.02 ± 0.95 | 2.91 ± 0.88 | 0.90 |
| FVC, percentage predicted | 83 ± 13 | 86 ± 11 | 80 ± 14 | 0.14 |
| FEV1/FVC | 0.64 ± 0.17 | 0.78 ± 0.06 | 0.52 ± 0.13 | <0.001 |
| Current smoker | 18 (45%) | 10 (56%) | 8 (36%) | 0.34 |
| Smoking history, pack-year[1] | 29 ± 25 | 13 ± 18 | 43 ± 23 | <0.001 |

FEV1, postbronchodilator forced expiratory volume in 1 second; FVC, postbronchodilator forced vital capacity. [1]Pack-year = (number of cigarettes smoked per day)/(20 × number of years of cigarette smoking). Data expressed as mean ± SD or n (%). Mann-Whitney U test or Fisher's exact test were used to measure differences between means and proportions, respectively.

Rodent model of airway fibrosis and emphysema after inhalation injury. To investigate the findings that elevated heme levels may be involved in chronic lung damage, a rodent model of inhalation injury was developed. Male C57BL/6 mice were exposed to air or $Br_2$ gas (400 ppm, 30 minutes) and returned to room air. Plasma heme and acute and chronic lung injury parameters were measured in mice on days 1, 7, 14, or 21 after $Br_2$ exposure.

Figure 2A:
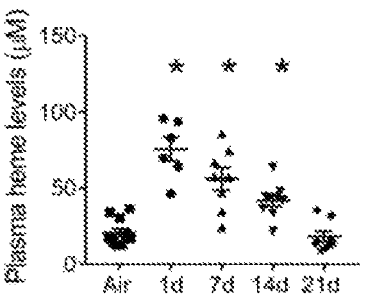
FIGS. 2A-2F show lung injury and fibrosis in rodent model of inhalation injury.
Figure 2B:
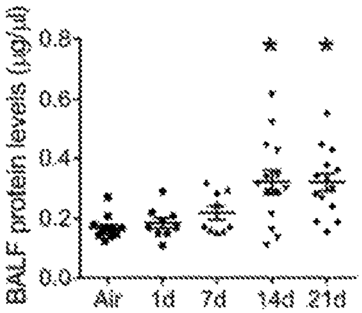
Figure 2C:
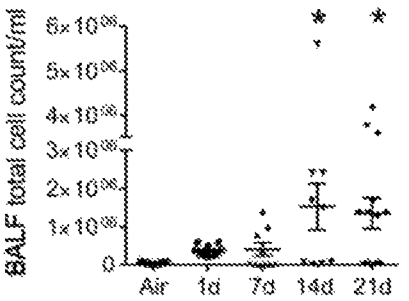
Figure 2D:
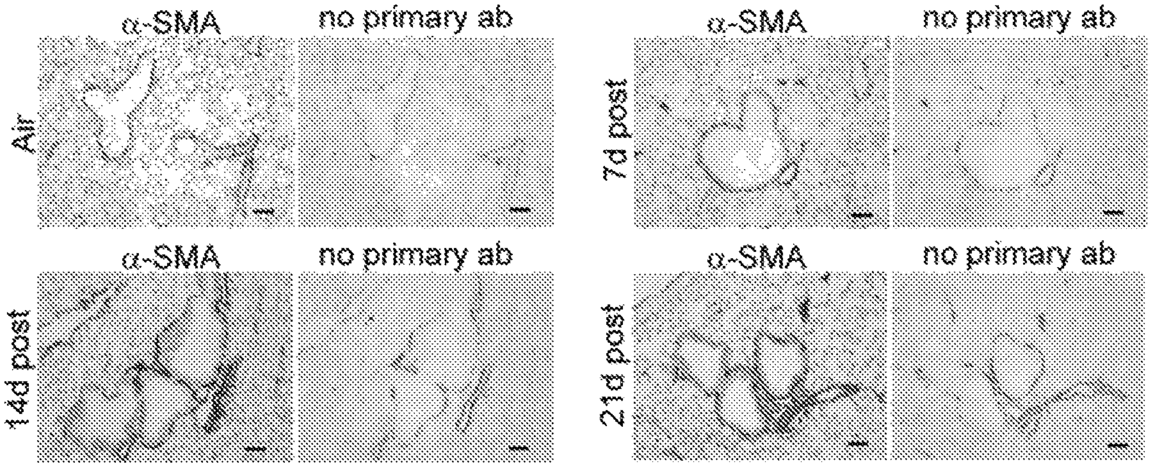
Figure 2E:
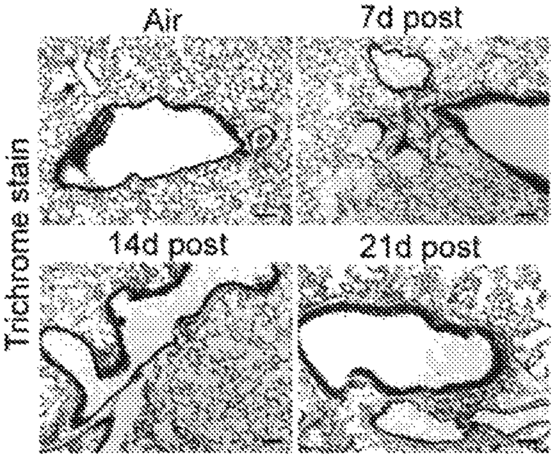
Figure 2F:
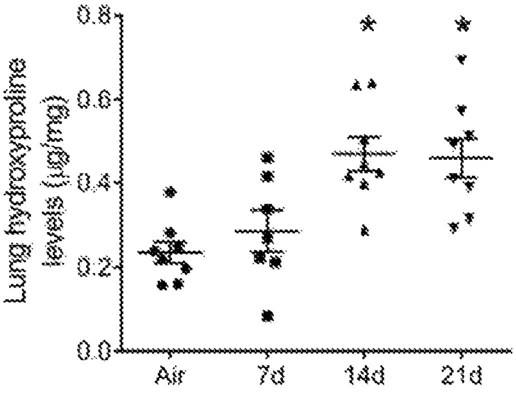

As shown in FIG. 2A, C57BL/6 mice of either sex exposed to 400 ppm of $Br_2$ gas for 30 minutes and returned to room air had elevated plasma heme levels for up to 14 days after exposure. To determine if elevated heme correlated with chronic lung injury, lung injury markers on days 1, 7, 14, and 21 were measured after $Br_2$ exposure. $Br_2$ increased bronchoalveolar lavage fluid (BALF) protein levels (FIG. 2B) and total cell count (FIG. 2C) on days 14 and 21 after exposure. After staining the lungs for α-smooth muscle actin (α-SMA) (as shown FIG. 2D) or with Masson's trichrome stain (as shown FIG. 2E), it was found that there was increased thickening of the smooth muscle layer around bronchioles and marked accumulation of collagen in the lungs, primarily around bronchioles on days 14 and 21 after exposure. Characteristic images were obtained from the indicated number of lungs for each condition. As demonstrated in FIG. 2F, the histological observation of lung airway fibrotic changes was accompanied by a significant increase in lung parenchymal hydroxyproline levels on days 14 and 21 after exposure.

Figure 3A:
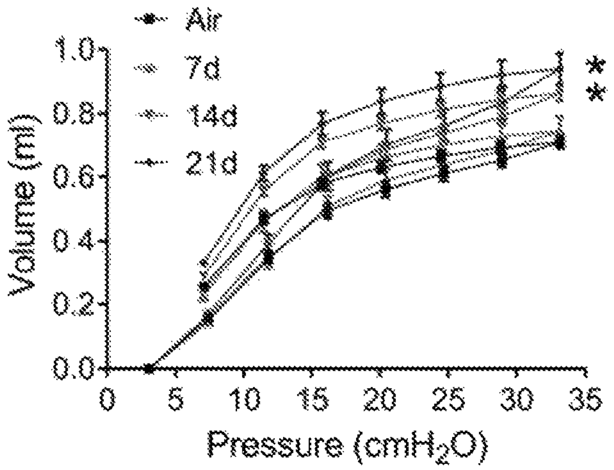
FIGS. 3A-3E show acute exposure to $Br_2$ induces lung emphysematous changes.
Figure 3B:
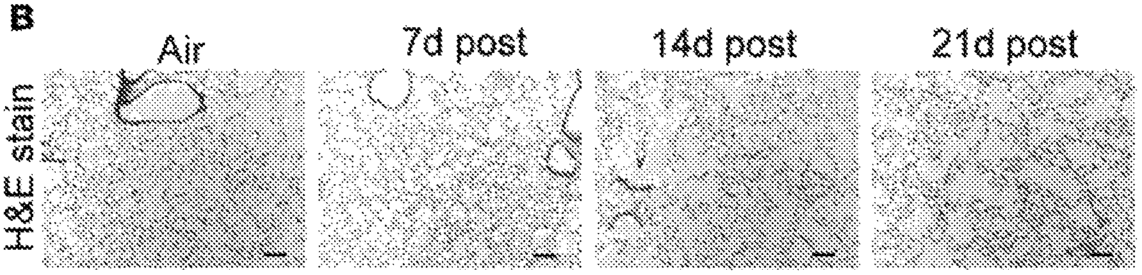
Figure 3C:
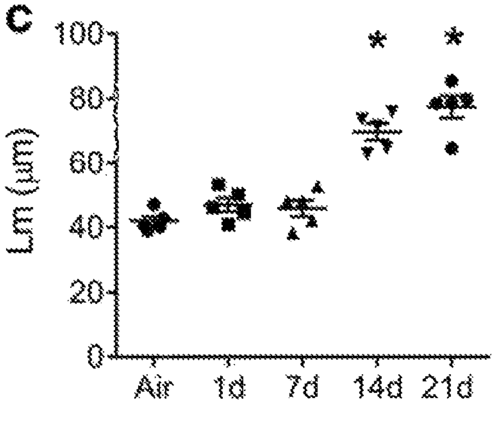
Figure 3D:
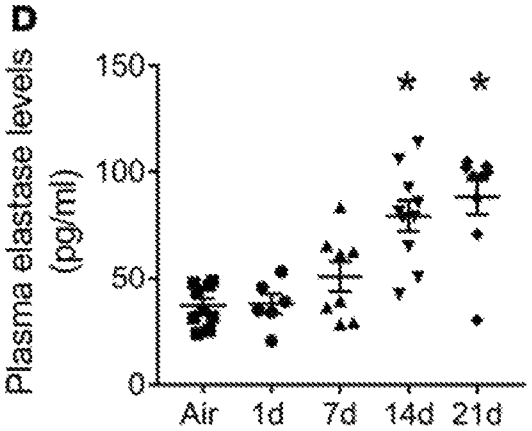
Figure 3E:
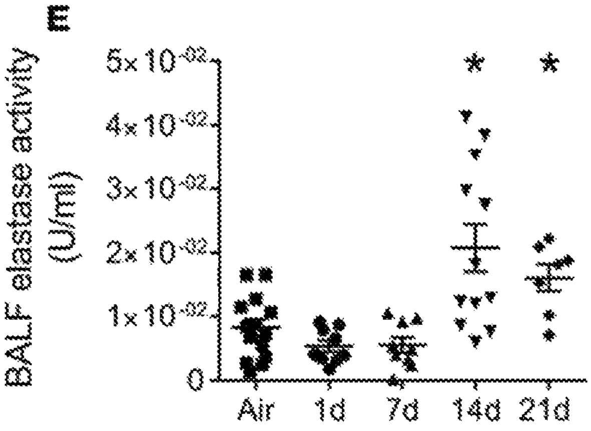

Male C57BL/6 mice were exposed to air or $Br_2$ gas (400 ppm, 30 minutes) and then returned to room air. On days 7, 14, or 21 after $Br_2$ exposure, mouse lung compliance was assessed by the slope of the deflation limbs of pressure-volume (PV) curves. Measurements of pressure-volume (PV) relationships in anesthetized mice with flexiVent at 7 to 21 days after exposure demonstrated that $Br_2$ exposure resulted in increased lung volumes, lung compliance, and inspiratory capacity, starting at 14 days after exposure (FIG. 3A). Subsequently, the lungs were stained with hematoxylin and eosin (H&E) (FIG. 3B) and the alveolar mean linear intercept ($L_m$) was measured (FIG. 3C). $L_m$ was increased in mice on days 14 and 21 after $Br_2$ gas inhalation. These pathological changes in the lung function and structure are characteristic of alveolar wall destruction and airspace enlargement seen in both experimental models of emphysema and in patients. The release of proteinases such as elastase by macrophages and neutrophils plays a significant role in alveolar wall destruction [9]. Plasma elastase levels (FIG. 3D) and BALF elastase activity (FIG. 3E) were increased in mice on days 14 and 21 after $Br_2$ exposure.

Figures 4A, 4B, 4C, 4D, 4E, 4F:
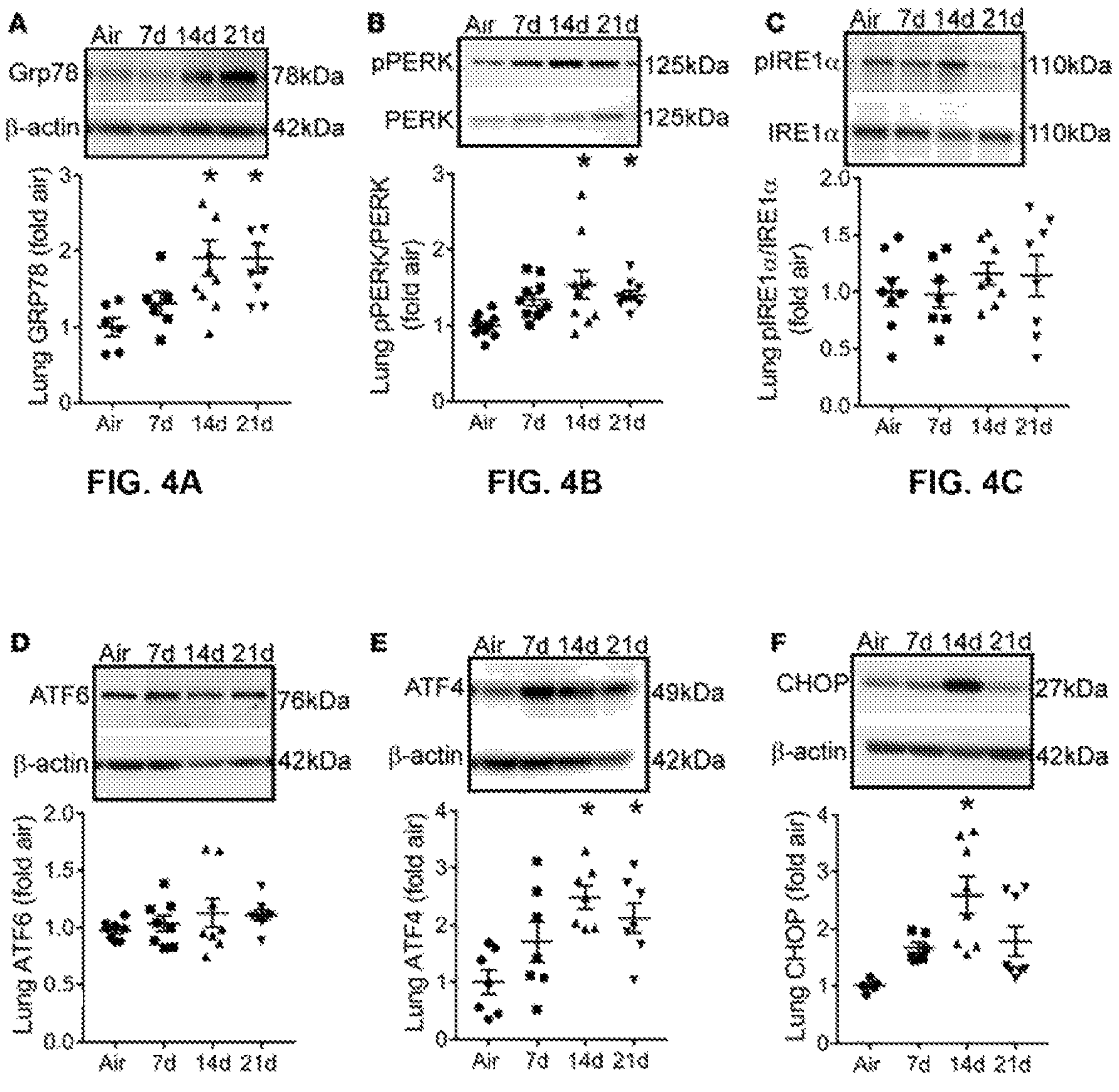
FIGS. 4A-4F show ER stress is increased in $Br_2$-exposed mice.

ER stress is elevated in mice, exposed to $Br_2$ gas. Peripheral lung tissue of mice exposed to $Br_2$ and returned to room air, was immunoblotted with antibodies against Grp78/Bip (FIG. 4A) and the downstream 3 major branches (protein markers) of the UPR: the double-stranded RNA-activated protein kinase-like ER kinase (p-PERK) (phosphorylated active form) (FIG. 4B), the inositol-requiring enzyme 1 (p-IRE1) (active form) (FIG. 4C), and the activating transcription factor 6 (ATF6) (FIG. 4D). GRP78/Bip and p-PERK levels were elevated in lungs of mice at days 14 and 21 after $Br_2$ exposure, while p-IRE1 and ATF6 were not. The activation of PERK leads to global inhibition of protein translation, with the exception of select proteins such as activating transcription factor 4 (ATF4) and the CCAAT/enhancer-binding protein homologous protein (CHOP). Both ATF4 (FIG. 4E) and CHOP (FIG. 4F) protein levels were elevated in the lungs of mice on day 14 after $Br_2$ inhalation.

Figure 5A:
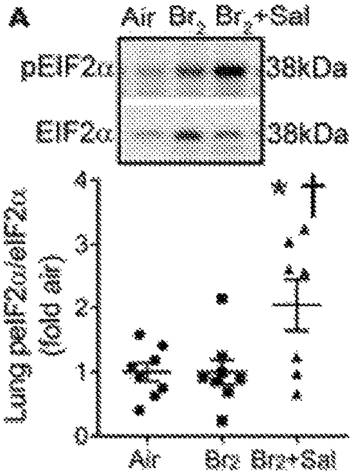
FIGS. 5A-5F show attenuation of ER stress abrogates lung injury and fibrosis.
Figure 5B:
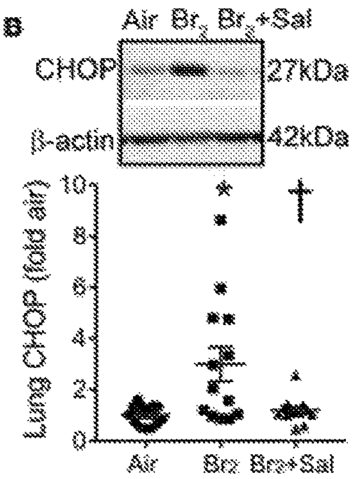
Figure 5C:
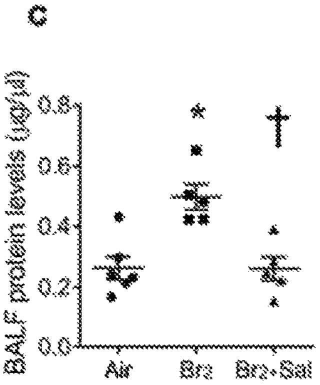
Figure 5D:
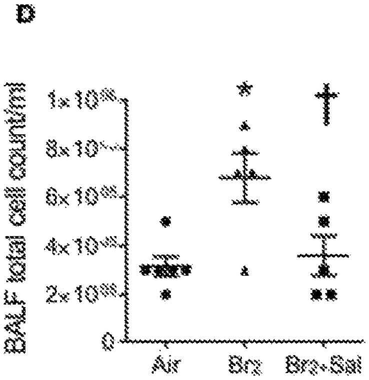
Figure 5E:
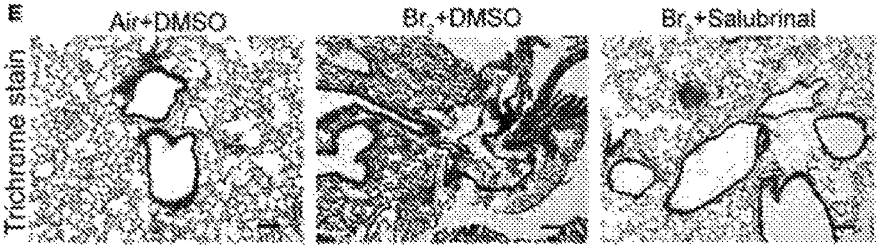
Figure 5F:
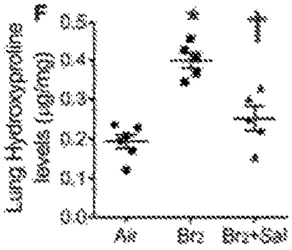

ER stress induces airway fibrosis and distal lung injury resembling human emphysema. To confirm the role of ER stress and the UPR in the pathogenesis of fibrosis and emphysema, mice were treated daily with a single i.p. injection of the ER stress inhibitor salubrinal (1 mg/kg BW), starting at 1 hour after $Br_2$ exposure until day 13, and changes in lung histology and function were analyzed on the 14th day after exposure. Air-exposed and some $Br_2$-exposed mice received DMSO (vehicle) as a control. Salubrinal is a selective inhibitor of eukaryotic initiation factor 2a (eIF2α) dephosphorylation and has been shown to protect against ER stress-mediated apoptosis [10-11]. eIF2α must be dephosphorylated to enable the translation of new proteins. Salubrinal attenuates unfolded or misfolded protein synthesis by inhibiting eIF2α dephosphorylation, thus decreasing CHOP and rescuing cells from apoptosis [12]. A significant increase in lung phosphorylated eIF2α (active form) (FIG. 5A) and a corresponding decrease in CHOP (FIG. 5B) levels were found in mice treated with salubrinal after $Br_2$ exposure. Furthermore, salubrinal ameliorated BALF protein levels (FIG. 5C) and BALF total cell count (FIG. 5D). Masson's trichrome staining of lungs (FIG. 5E) and quantification of lung hydroxyproline levels (FIG. 5F) showed decreased collagen levels and lung fibrotic changes in $Br_2$-exposed mice after treatment with salubrinal.

Figure 6A:
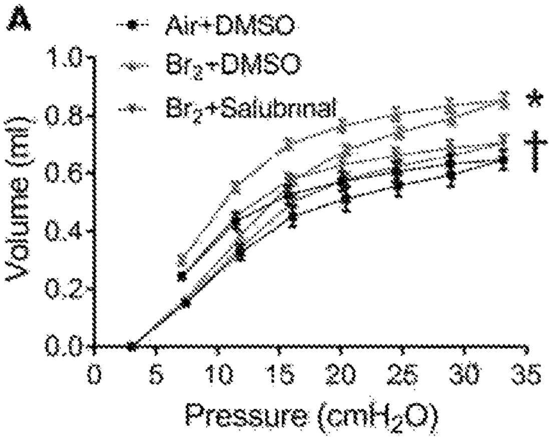
FIGS. 6A-6E show attenuation of ER stress reduces lung emphysematous changes.
Figure 6B:
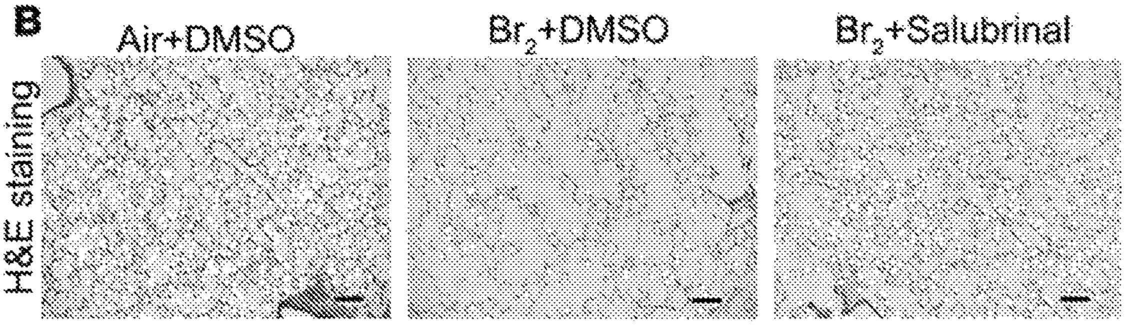
Figure 6C:
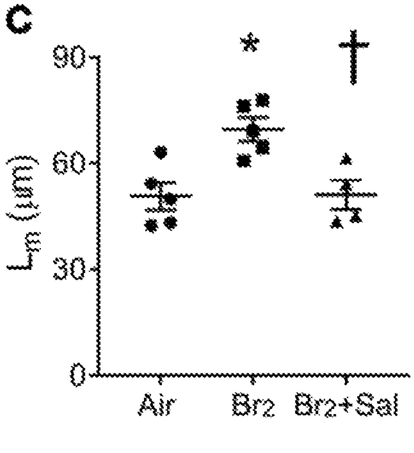
Figure 6D:
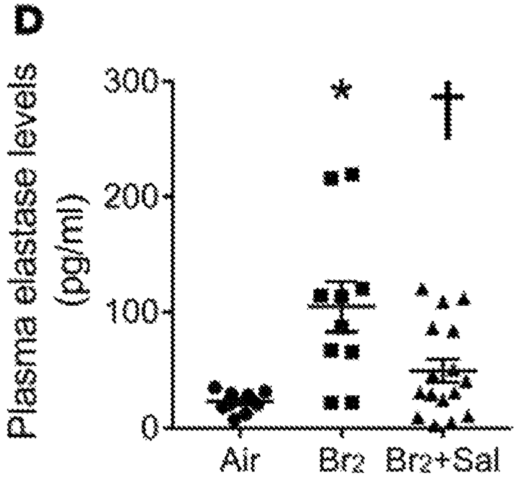
Figure 6E:
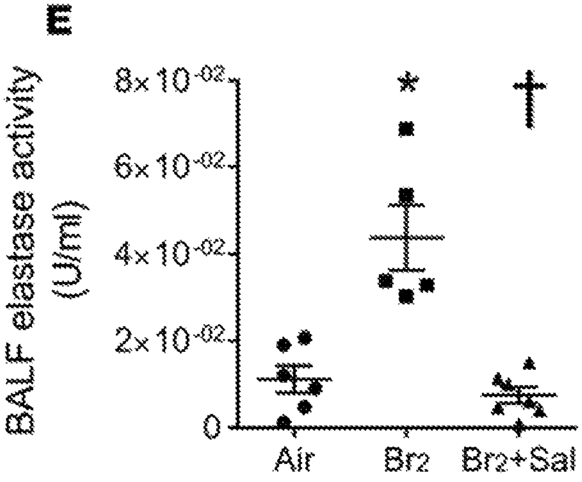

Additionally, PV curve measurements demonstrated that salubrinal prevented $Br_2$-induced increase in lung volumes (FIG. 6A), as well as lung compliance and inspiratory capacity. Salubrinal also attenuated alveolar $L_m$ (FIG. 6C), as shown on H&E staining (FIG. 6B), plasma elastase levels (FIG. 6D), and BALF elastase activity (FIG. 6E) in comparison with the mice treated with DMSO after $Br_2$ exposure.

Figure 7A:
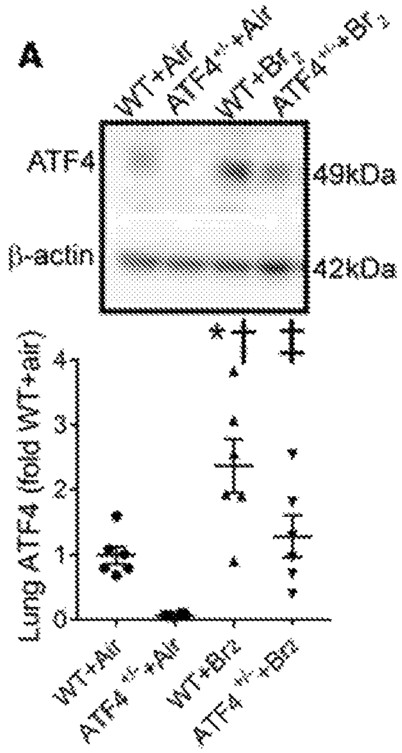
FIGS. 7A-7H show ATF4-haplodeficient mice ($ATF4^{+/-}$) mice are protected against inhalation injury.
Figure 7B:
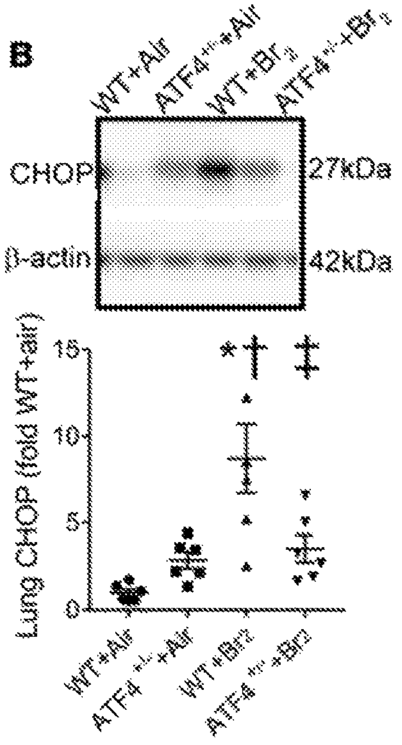
Figure 7C:
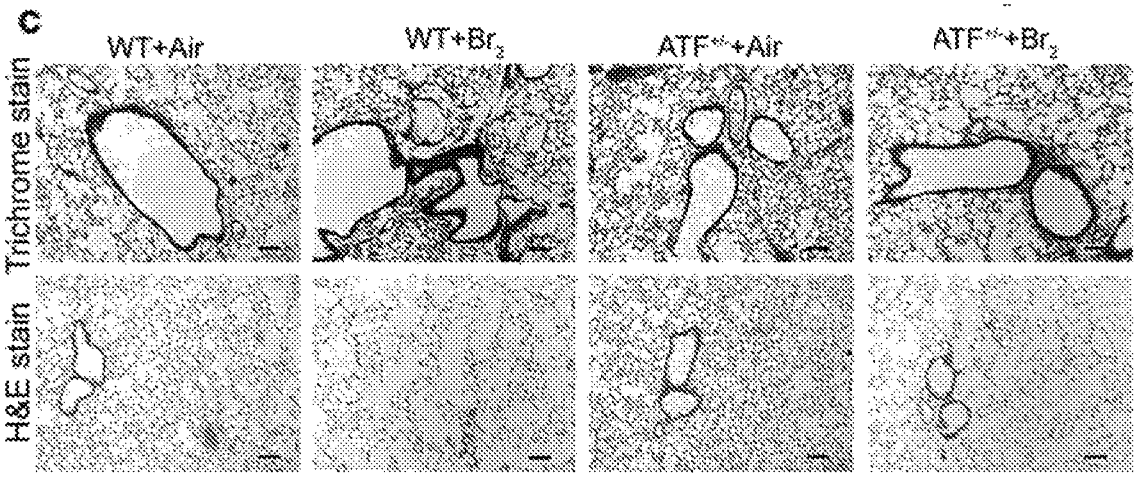
Figure 7D:
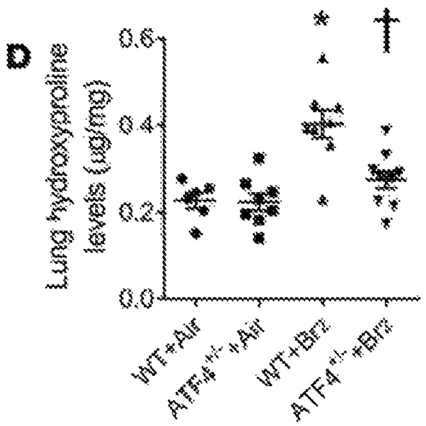
Figure 7E:
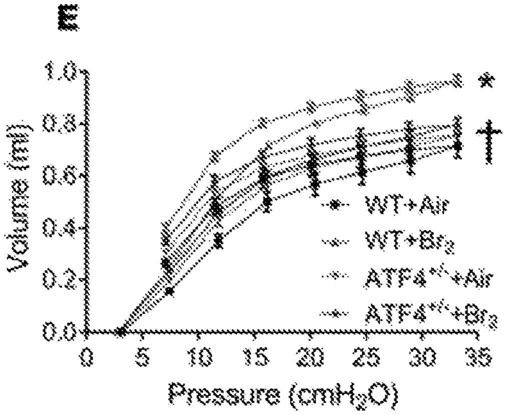
Figure 7F:
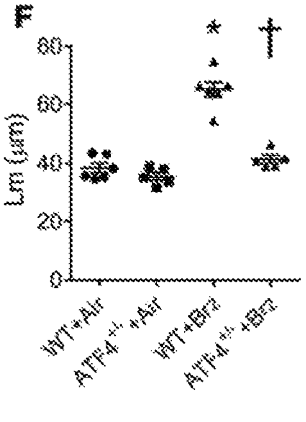
Figure 7G:
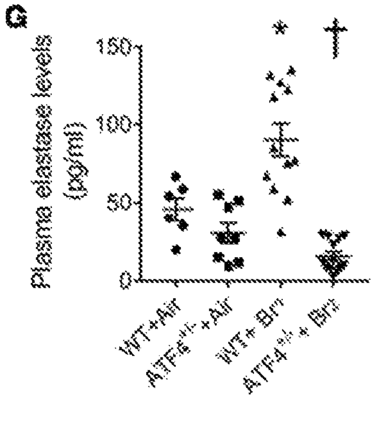
Figure 7H:
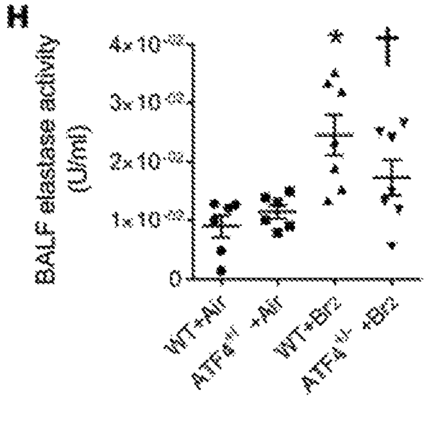

Moreover, ATF4-haplodeficient mice ($ATF4^{+/-}$) were subjected to $Br_2$ (400 ppm, 30 minutes) to investigate whether these mice were protected against $Br_2$-induced lung pathology 14 days after exposure. ATF4-homodeficient mice ($ATF4^{-/-}$) had severe developmental abnormalities and were not used in these experiments. The results demonstrated that $ATF4^{+/-}$ mice had lower lung levels of ATF4 (FIG. 7A) and CHOP (FIG. 7B) after $Br_2$ inhalation compared with the corresponding wild-type (WT) mice. Exposure to $Br_2$ increased lung collagen deposition (trichrome staining) (FIG. 7C) and lung hydroxyproline levels (FIG. 7D) in the WT mice, but not in the $ATF4^{+/-}$ mice. In addition, $ATF4^{+/-}$ mice did not develop an emphysematous phenotype after $Br_2$ inhalation, as demonstrated by the lack of changes in PV curves (FIG. 7E) and the demonstrable no increase in lung compliance and inspiratory capacity. In addition, $ATF4^{+/-}$ mice did not have an increase in $L_m$ (FIG. 7F) on H&E staining (FIG. 7C), plasma elastase levels (FIG. 7G), and BALF elastase activity (FIG. 7H) after $Br_2$ exposure. In comparison, WT mice showed emphysematous lung changes. Together, these results suggest that prolonged ER stress impairs lung injury repair, which leads to the development of lung fibrotic and emphysematous changes.

Figure 8A:
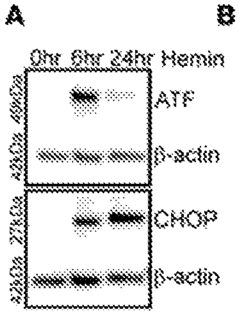
FIGS. 8A-8E show heme scavenging attenuates ER stress.
Figure 8B:
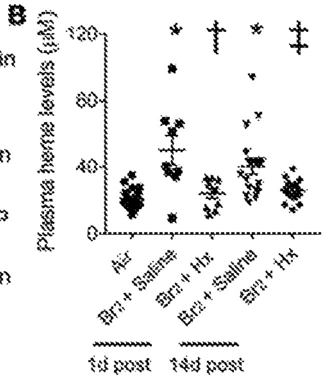
Figure 8C:
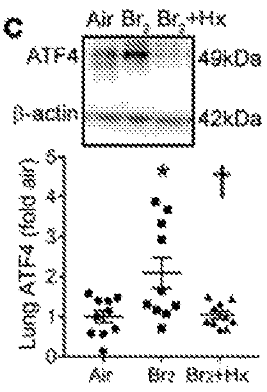
Figure 8D:
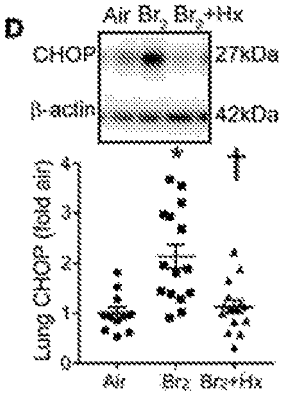
Figure 8E:
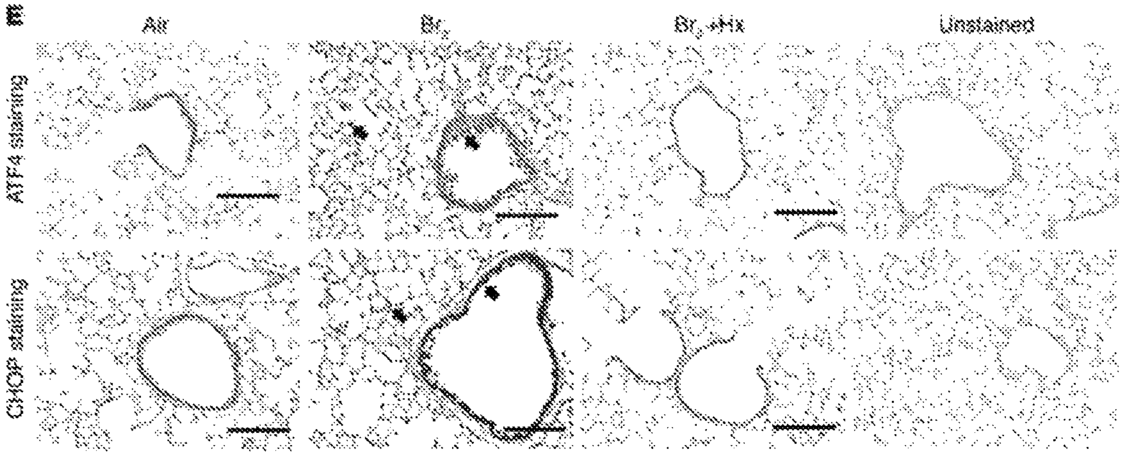

Heme scavenging attenuates ER stress and prevents the development of chronic lung injury. To investigate if heme may lead to ER stress, human bronchial epithelial cells (HBECs) with hemin (a form of heme, 25 μM) were incubated, and increased ER stress markers ATF4 and CHOP (FIG. 8A) were seen within 6 hours after hemin challenge. In contrast, exposure of these cells to $Br_2$ (100 ppm, 10 minutes) (in the absence of exogenous heme) only increased ATF4, while CHOP levels remained unaltered. Next, to determine if heme scavenging can abrogate ER stress, an i.p. injection of the heme-scavenging protein Hpx (purified human plasma Hpx, 4 μg/g BW) was given to mice, 1 hour after $Br_2$ exposure. Hpx administration reduced plasma heme after $Br_2$ exposure (FIG. 8B). Hpx reduced ER stress as indicated by low levels ATF4 (FIG. 8C) and CHOP (FIG. 8D) in the lungs 14 days after $Br_2$ exposure. Similarly, immunohistochemical staining of lung sections showed that ATF4 and CHOP (FIG. 8E) levels were higher and predominantly expressed around bronchioles 14 days after $Br_2$ exposure. Treatment with Hpx attenuated ATF4 and CHOP levels around airways and completely abrogated the ER stress markers in the lung parenchyma.

Figure 9A:
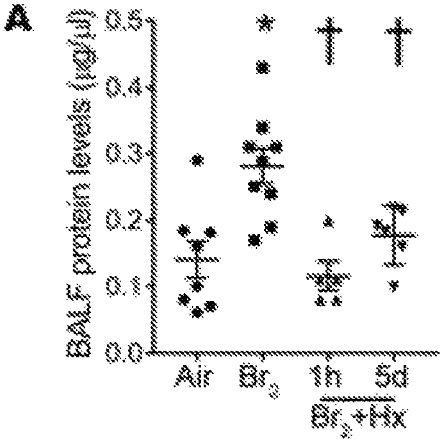
FIGS. 9A-9I show hemopexin attenuates lung injury, airway fibrosis, and lung emphysema.
Figure 9B:
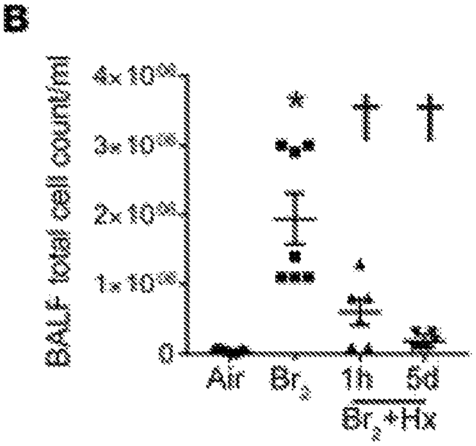
Figure 9C:
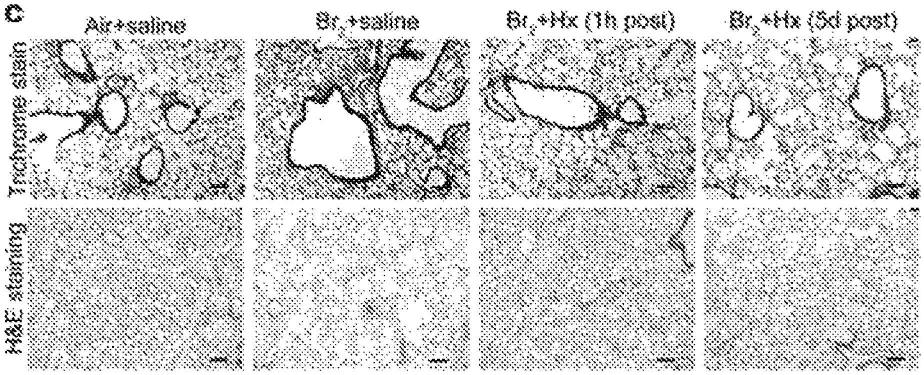
Figure 9D:
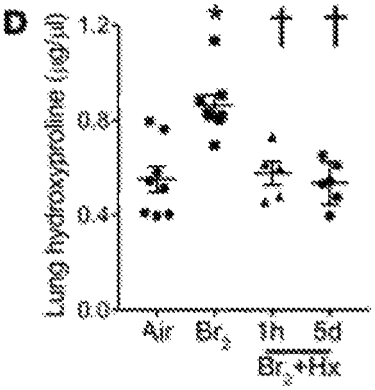
Figure 9E:
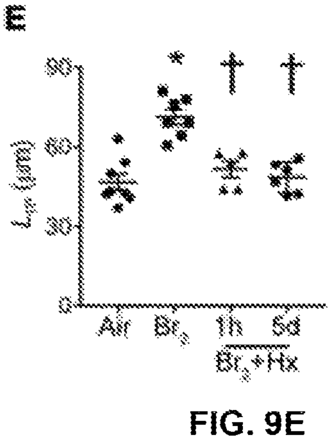
Figure 9F:
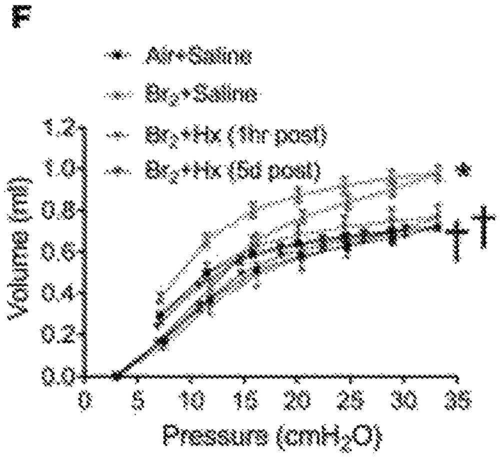
Figure 9G:
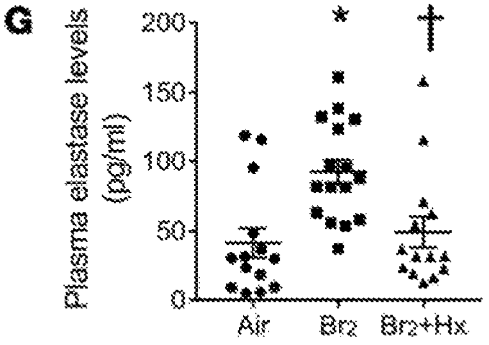
Figure 9H:
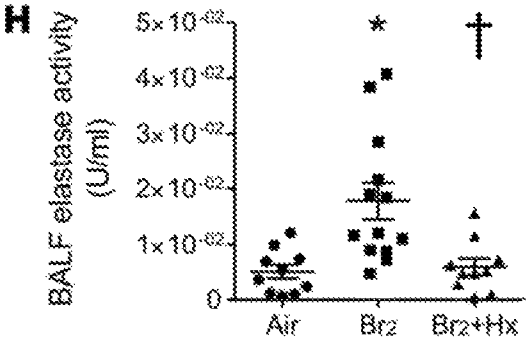
Figure 9I:
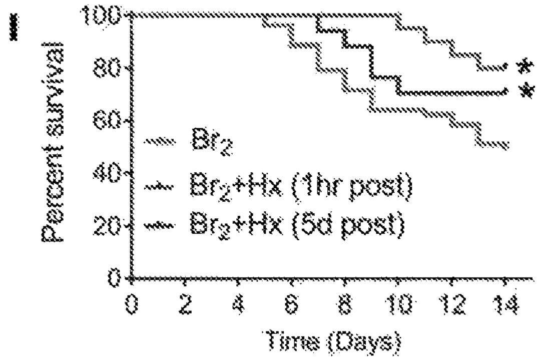

To ascertain the therapeutic potential of Hpx in preventing or reversing chronic lung damage after inhalation injury, an i.p. injection of purified human Hpx (4 μg/g BW) was given to mice, either 1 hour after $Br_2$ exposure, or in some key experiments 5 days after $Br_2$. The results indicate that the plasma concentration of mouse Hpx was significantly higher in mice that were administered purified human Hpx 1 hour after $Br_2$ exposure on day 14 after exposure. Hpx administered either at 1 hour or 5 days after $Br_2$ significantly reduced BALF protein levels (FIG. 9A), BALF total cell count (FIG. 9B), lung collagen levels on Masson's trichrome staining (FIG. 9C), and lung hydroxyproline levels (FIG. 9D) in mice 14 days after $Br_2$ inhalation. Hpx also reduced alveolar $L_m$ (FIG. 9E) upon H&E staining (FIG. 9C), prevented the shifting of the PV curve (FIG. 9F), and an increase in lung compliance and inspiratory capacity. Hpx-treated mice also had lower plasma elastase levels (FIG. 9G) and BALF elastase activity (FIG. 9H) 14 days after $Br_2$ gas inhalation. Finally, postexposure injection with Hpx reduced overall mortality in C57BL/6 mice compared with mice injected with saline after $Br_2$ inhalation (FIG. 9I).

Example 2: Phosgene Inhalation Causes Hemolysis and Acute Lung Injury

The purpose of this working example was to assess the extent of phosgene ($COCl_2$) injury to the blood gas barrier and red blood cells of unanesthetized mice. To accomplish these goals, equal numbers of adult male and female mice were exposed to 10 or 20 ppm $COCl_2$ in environmental chambers for 10 minutes and returned to room air. The following parameters were assessed at different times post-exposure: survival, body weight changes, physiological and histochemical indices of lung function and injury including arterial blood gases, plasmalogen levels, and levels of hemoglobin and free heme in the plasma. Mice exposed to $COCl_2$ showed evidence for increased RBC fragility, oxidative injury to RBC membranes, damage to plasma plasmalogens and the onset of delayed but severe lung injury which mimics human Adult Respiratory Distress Syndrome. Furthermore, there was considerable oxidation of important RBC structural proteins and band 3 which may contribute to hemolysis.

Materials and Methods

Reagents. Ketamine was obtained from Vedco Inc. (St. Joseph MO); Xylazine from Vet One, (Boise, ID); the heme assay kit was from QuantiChrom (Product No. DIHM-250; BioAssaySystems, Hayward, CA); 4 mm Pyrex solid glass beads from Sigma-Aldrich (St Louis, MS); 4-20% Tris-HCl Criterion precast gels from Bio-Rad Laboratories (Product number: 567-1094, Hercules, CA); Amido Black from Sigma-Aldrich (St Louis, MS); RIPA buffer from Thermo Fisher Scientific (MA); Oxyblot protein oxidation detection kit from EMD Millipore (Product number: S7150, Billerica, MA).

Animals. Adult male and female C57BL/6 mice (20-25 g) were bought from Charles River (Wilmington, MA). Mice were allowed to acclimatize in the Animal Vivarium located in the basement of the Biomedical Research Building II for at least four days, where they were cared for by personnel from Animal Resources Program. All animal care and experimental procedures were approved by the Institutional Animal Care and Use Committee at the University of Alabama in Birmingham (protocol #21451). Mice that exhibited respiratory symptoms, or refused to eat and drink, were not included in these studies.

Exposure to phosgene gas. On the day of the exposure, mice of either sex were placed, five at a time, in a 4.5 L glass exposure chamber. The exposure chambers were located inside a negative pressure hood, inside a room at the Animal Vivarium, maintained at negative pressure compared to the rest of the Vivarium. The exposure chamber was connected to either compressed air or $COCl_2$ gas (nominal concentrations of 20 or 10 ppm, certified within 2%, purchased from SpecGas, Inc. Warminster, PA). The flow rate was set at 2.5 L/min. The concentration of $COCl_2$ was monitored by an Analytical Technology, Inc. (Collegeville, PA) A21 Gas Sampling System, F12D Gas Transmitter with Phosgene Sensor (00-1016) Standard Range=0-100 ppm; Resolution=0.1 ppm) in a random fashion in 30% of the exposures. In addition, the concentration of $CO_2$ in the chambers was monitored by a UEi C20 combustion meter (Beaverton OR). The gas exiting the chamber was passed through a 10% solution of NaOH to scavenge the $COCl_2$ and vented to the roof of the building.

At the end of each ten minute exposure, the gas was turned off, the chamber lid was removed and after a short period of time, the mice were returned to their cages in the Vivarium where they were provided with food and water ad libitum and observed by both laboratory and technicians of the Animal Facility. All personnel involved in the exposure of mice to $COCl_2$ underwent special training by the Occupational Health and Safety division of the University of Alabama at Birmingham. A $COCl_2$ detector, (purchased from Gas Sensing, Hull IA), equipped with an audible alarm and a strobe light was mounted on the wall of the exposure room and was set to sound an alarm if the $COCl_2$ concentration in the room exceeded 0.5 ppm.

Histological analysis of the mouse lung. Mice were euthanized with an intra-peritoneal injection of ketamine and xylazine (160 and 80 mg/kg body weight, respectively). The chest was opened and the lungs were removed, fixed in 10% alcoholic formalin for 24 h and dehydrated in 70% ethanol before embedding in paraffin. Paraffin-embedded tissues were cut into 4 μm sections then de-paraffinized and rehydrated using Citrisolv (d-limonene based solvent) and isopropanol, respectively. The sections were stained with hematoxylin and eosin (H & E). Images were captured using a Leica DMI 6000 B microscope (Leica Microsystems Inc., Bannockburn, IL) and Leica Application Suite V4.2 software.

Plasma heme assays. Non-encapsulated heme levels were measured in plasma samples by two different methods: first, by using the QuantiChrom heme assay kit (Product No. DIHM-250; BioAssay Systems, Hayward, CA), according to the manufacturer's instructions. This method measures total non-encapsulated heme and hemoglobin levels and second, by spectral deconvolution with least square fitting analyses, which allows for separate measurements of non-encapsulated hemoglobin and heme.

Red blood cell fragility. Red blood cells from air and $COCl_2$ exposed mice were washed thoroughly to remove free heme. RBCs were re-suspended, at 1.0% hematocrit, with 4 mm Pyrex solid glass beads (10 beads, 0.4 ml RBC suspension volume in 2 ml round bottom Eppendorf tubes) in DPBS. This solution was rotated 360° for 2 h at 24 rpm at 37° C. The hemoglobin released from the RBCs during rotation was transferred into a new tube and centrifuged at 13,400 g for 4 min and the absorbance of the supernatant were recorded at 540 nm. Subsequently, one hundred percent hemolysis of RBCs was achieved by treating them with 1% Triton x-100 solution. The fractional hemolysis of the sample was then obtained by dividing the optical density of the sample by the optical density of the 100% hemolyzed sample.

Respiratory mechanics. Mice were mechanically ventilated and challenged with increasing concentrations of methacholine as described previously [13]. Briefly, mice were anesthetized with pentabarbitol (90 mg/kg), intubated, connected to a ventilator (flexiVent; SCIREQ, Montreal, PQ, Canada) and ventilated at a rate of 160 breaths per minute at a tidal volume of 0.2 ml with a positive end-expiratory pressure of 3 cm $H_2O$. Total respiratory system resistance (R) and elastance (E) were recorded continuously as previously described [13]. Baseline lung volume was set via deep inhalation. Increasing concentrations of methacholine chloride (0-50 mg/ml, Sigma-Aldrich, St Louis, MS) were administered via aerosolization within an administration time of 10 seconds. Airway responsiveness was recorded every 15 seconds for 3 minutes after each aerosol challenge. Broadband perturbation was used and impedance was analyzed via constant phase model.

Arterial blood gases. Mice were anesthetized with Isoflurane (5% for induction, 2% for maintenance) using compressed air as vehicle. The abdomen was opened, the mesentery was externalized to the left side of the mouse to visualize the abdominal aorta. Arterial blood was collected into a heparinized syringe through a 23-gauge needle inserted into the aorta. Blood gas analysis was performed immediately after collection using an Element POC analyzer (Heska, Loveland, CO).

SDS-PAGE and oxyblots. Mice were anesthetized and euthanized. Their lungs were then lavaged with one mL of saline which was instilled and withdrawn three times. The cells were pelleted by centrifugation (5 min at ×200 g) 1000 g. Cleared supernatants were used to measure the protein concentration by the BCA assay; equal volume of BAL (2 μl) were loaded on 4-20% Tris-HCl Criterion precast gels (Product number: 567-1094, Bio-Rad Laboratories, Hercules, CA). In addition, RBCs were separated from the plasma and hemolyzed with 20 mM hypotonic HEPES (4-(2-hydroxyethyl)-1-piperazineethanesulfonic acid) buffer. The mixture was centrifuged at 14000×g for 20 min and the RBC pellet was dissolved in RIPA (Radioimmunoprecipitation assay) buffer. The protein was quantified by the BCA method and equal amounts of proteins (10 μg) were loaded into a 4-20% gradient gel and proteins were separated and stained with Amido Black.

The presence of protein carbonyl groups was assessed using the Oxyblot protein oxidation detection kit (Product number: S7150, EMD Millipore, Billerica, MA), according to the manufacturer's protocol. Briefly, the carbonyl groups in the protein side chains were derivatized to 2,4-dinitrophenylhydrazone by reacting with 2,4-dinitrophenylhydrazine. Precisely, 10 μg of protein was used for each sample, and the 2,4-dinitrophenol-derivatized protein samples were separated by polyacrylamide gel electrophoresis. Polyvinylidene fluoride membranes were incubated for 1 hour in the stock primary antibody (1:150 in PBST buffer), and after washing, for 1 hour in the stock secondary antibody (1:300 in PBST buffer). Membranes were washed 3 times in PBST and visualized. The abundance of protein carbonylation was assessed by densitometry of each lane and normalization for each lane protein loading was done by SDS PAGE gel quantification.

Quantification of plasmalogens in plasma. Equal number of male and female mice were sacrificed 24 hours post exposure to either air or $COCl_2$. Plasma was subjected to a modified Bligh-Dyer lipid extraction (Blight and DYER, 1959) in the presence of lipid class internal standards including 1-0-tetradecanoyl-sn-glycero-3-phosphoethanolamine and 1,2-ditetradecanoyl-sn-glycero-3-phosphoethanolamine. Lipid extracts were diluted in methanol/chloroform (1/1, v/v) and molecular species were quantified using electrospray ionization mass spectrometry on a triple quadrupole instrument (Thermo Fisher Quantum Ultra) employing shotgun lipidomics methodologies [14]. Ethanolamine glycerophospholipid and lysophosphatidylethanolamine molecular species were first converted to 9-fluorenylmethoxycarbonyl (fMOC) derivatives and then quantified in the negative ion mode using neutral loss scanning for 222.2 amu (collision energy=30 eV).

Statistical analysis. Statistical analysis was performed using GraphPad Prism version 4.01 for Windows (GraphPad Software, San Diego, CA). The mean±SEM was calculated in all experiments, and statistical significance was determined by either the one-way or the two-way ANOVA. For one-way ANOVA analyses, Tukey's post-test post-hoc testing was employed, while for two-way ANOVA analyses, Bonferroni post-tests were used. Overall survival was analyzed by the Kaplan-Meier method. Differences in survival were tested for statistical significance by the log-rank test. A value of $P<0.05$ was considered significant.

Results

Figure 10:
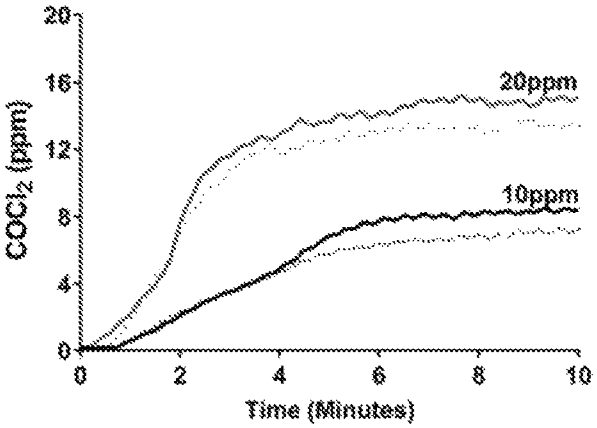
FIG. 10 is a graph showing continuous measurement of $COCl_2$ concentrations inside the exposure chambers. Measurements were conducted with five mice in the chamber (dotted lines) or with empty chambers (solid lines). Measurements were repeated twice with similar results.

Whole body exposure to $COCl_2$ in glass chamber. $COCl_2$ gas (nominal concentrations of 20 ppm or 10 ppm flowed into the exposure chambers (volume=4.5 L) at 2.5 L/min starting at zero time. The concentration of $COCl_2$ was monitored by Analytical Technology, Inc. (Collegeville, PA) A21 Gas Sampling System, F12D Gas Transmitter with Phosgene Sensor. As shown in FIG. 10, $COCl_2$ concentrations in the exposure chamber rose after onset of $COCl_2$ flow and reached a steady state after approximately five minutes. There were no differences in the concentration profiles whether or not mice were present in the chambers, indicating that absorption of $COCl_2$ by the fur was negligible. The differences in steady state concentrations recorded by the $COCl_2$ detector and the certified nominal $COCl_2$ concentrations were within the stated accuracy of the detector. Based on the profiles shown in FIG. 10, the areas under the concentration profiles were 57.5 and 156 ppm×min. For simplicity the exposures are referred to as 10 and 20 ppm. $CO_2$ concentrations in the exposure chamber were undetectable during the exposure period.

Figure 11A:
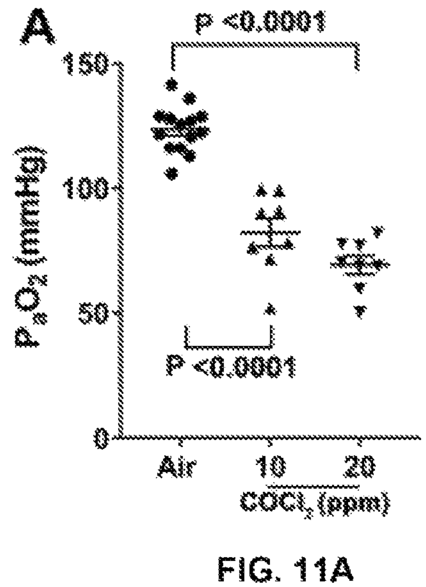
FIGS. 11A-11D show measurements of arterial blood gases in $COCl_2$ exposed mice.
Figure 11B:
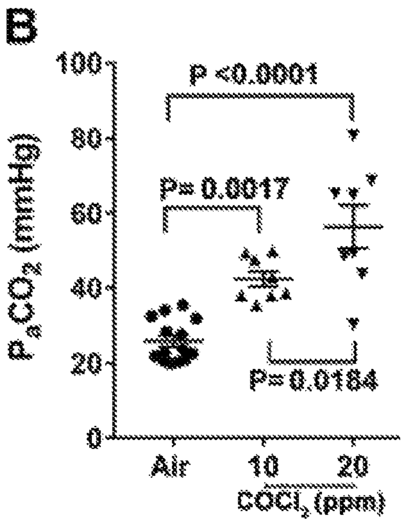
Figure 11C:
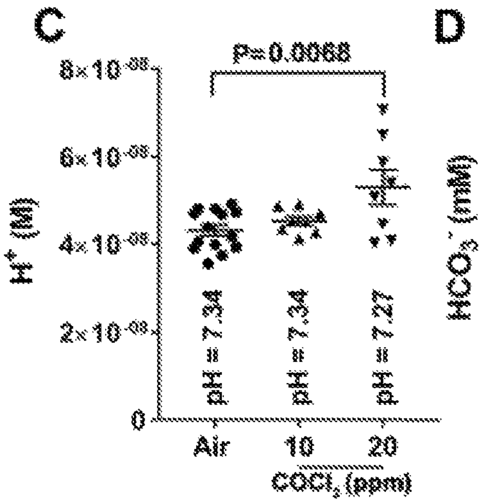
Figure 11D:
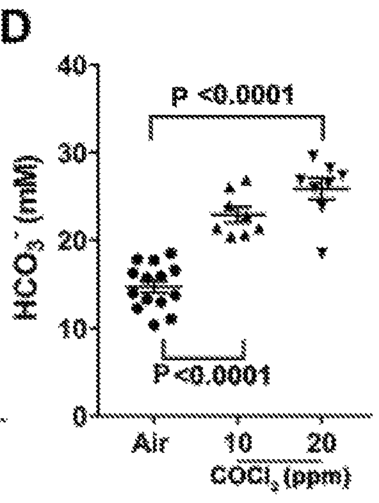

Exposure to $COCl_2$ results in hypoxemia and respiratory acidosis. Adult C57BL/6 mice were exposed to air or $COCl_2$ (10 ppm or 20 ppm) for 10 minutes. Mice appeared alert and unaffected by $COCl_2$ both during the exposure and within the first 12 hours of return to air. After that time until they were sacrificed 24 hours later, the mice exhibited reduced activity levels but they did not exhibit overt respiratory distress, i.e., lacked labored breathing, flaring of the nostrils and expiratory grunting. Measurements of arterial blood gases (FIG. 11), $Pa_{O2}$ (FIG. 11A), $Pa_{CO2}$ (FIG. 11B), pH (FIG. 11C), and $HCO_3^-$ (FIG. 11D) were performed in anesthetized mice using an Element POC analyzer (Heska, Loveland, CO). Twenty four hours post $COCl_2$, mice developed dose-dependent hypoxemia [$Pa_{O2}$ (torr)=124±2.6 [15]; 82±6 [16]; 69±4 [16]; X±SEM; (number of mice) for air, 10 ppm and 20 ppm $COCL_2$ respectively] and hypercapnia [$Pa_{CO2}$ (torr)=26±1.5 [15]; 42.3±2 [16]; 56±6 [16]] and respiratory acidosis, which was compensated by an increase in plasma bicarbonate [$HCO_3^-$ (mM)=15±0.7; 23±0.9 [16];

26±1.3 [16]]. The increase in $HCO_3^-$ was consistent with a decrease in plasma chloride (Cl—) concentration (data not shown).

Figure 12A:
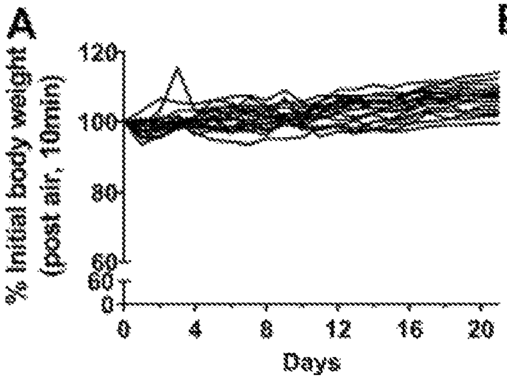
FIGS. 12A-12D show measurements of body weight and mortality in mice exposed to $COCl_2$.
Figure 12B:
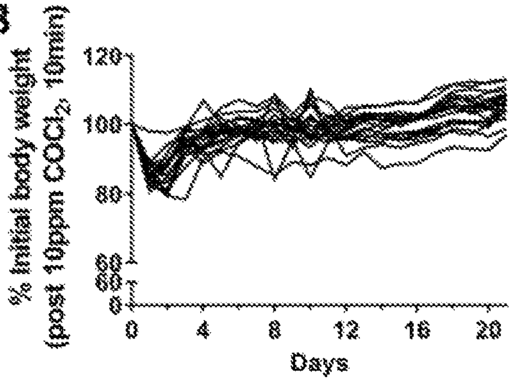
Figure 12C:
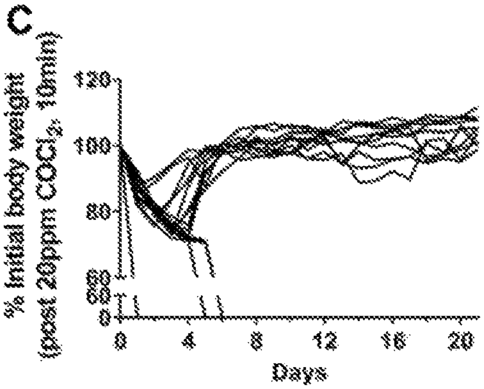
Figure 12D:
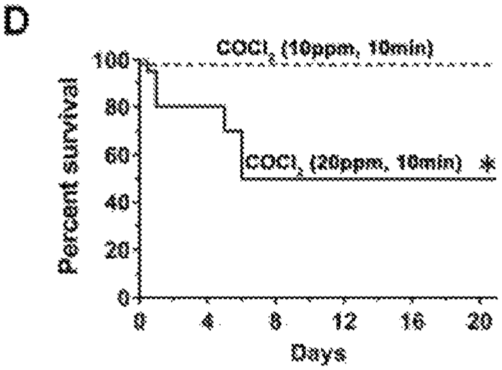

Exposure to $COCl_2$ increases mortality in mice. Equal number of male and female C57BL/6 were placed five at a time in the environmental exposure chambers and exposed to air (n=18), 10 ppm $COCl_2$ (n=20) or 20 ppm $COCl_2$ (n=20) for 10 minutes. At the end of the exposure, the gas flow was stopped, the top lid of the chamber removed and the mice were transferred to their normal holding cages. Their body weights were measured daily and expressed as % of initial (i.e. pre-exposure) weights. As shown in FIG. 12A, air breathing mice continued to gain weight, eat and drink for the next 21 days. Mice exposed to 10 ppm $COCl_2$ experienced a transient 15% decrease of body weight during the first 24 hours post exposure, but resumed eating and drinking and gaining weight as the air controls (FIG. 12B). All of these mice were alive at 21 days post exposure. On the other hand, mice exposed to 20 ppm $COCl_2$ for 10 minutes and returned to room air, continued to lose weight during the first 5 days post exposure (FIG. 12C). Two of these mice died during the first 24 hour post exposure and three mice were sacrificed because their body weights dropped below 30% of their pre-exposure weights. Kaplan-Meyer curves for mice exposed to 10 or 20 ppm $COCl_2$ are shown in FIG. 12D. Mice exposed to 20 ppm for 10 minutes $COCl_2$ exhibited approximately 50% survival following return to room air; all deaths occurring in the first six days post exposure (FIG. 12D).

Figure 13A:
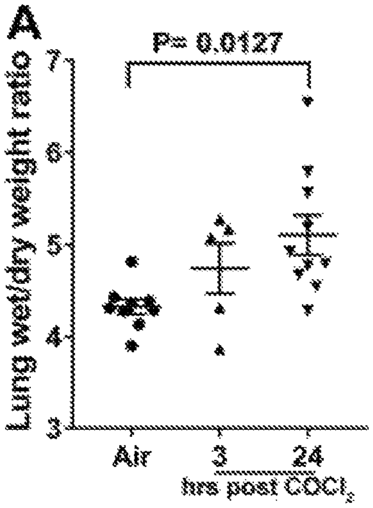
FIGS. 13A-13C show measurements of lung edema in mice exposed to $COCl_2$.
Figure 13B:
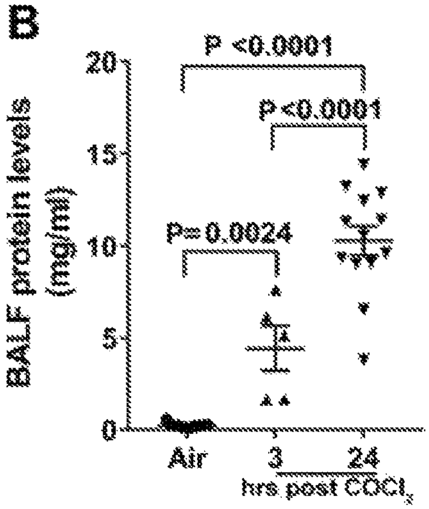
Figure 13C:
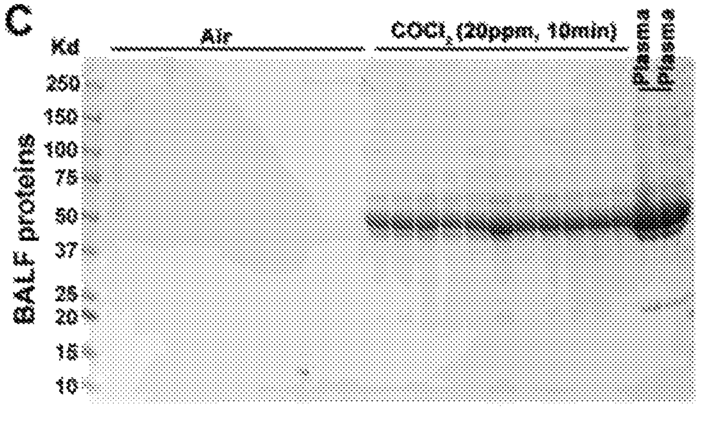

Exposure to 20 ppm $COCl_2$ damages the distal lung regions and results in inflammation. An equal number of male and female mice were sacrificed 3- or 24-hours post exposure to either air or 20 ppm $COCl_2$ for 10 min; their chests were opened and lungs removed en bloc, blotted and non-lung tissue was removed. They were then weighted for determination of wet weight and placed in an oven at 70° C. for seven days at which point they were reweighted for measurement of dry weights. Consistent with the data shown in FIGS. 12A-12D, mice exposed to $COCl_2$ (20 ppm, 10 min) had severe injury to the blood gas barrier 24 hours post exposure. As shown in FIGS. 13A and 13B, there was a progressive and significant increase of the lung/wet dry weight (FIG. 13A) (W/D=4.3±0.1 [17]; 4.7±0.3 [18]; 5.1±0.22(10); X±SEM; (number of mice) for air, 10 ppm and 20 ppm $COCl_2$ respectively) consistent with the presence of interstitial and alveolar edema, and a 10 fold increase of plasma proteins in the bronchoalveolar lavage fluid (BALF) (FIG. 13B) [BAL Pr. (mg/ml)=0.2±0.03 [19]; 4.45±1.34 [18]; 10.3±0.84 [19]]. Interestingly, the magnitude of increased lung edema far exceeded (by 5-10 fold) that observed in mice exposed to HCl [13], $Cl_2$ or $Br_2$ ([8], [20]; [21]); maximal BALF protein levels in these mice are in the 1-2 mg/ml range. No significant amount of proteins was detected in the BALF of air breathing mice; however, SDS PAGE analysis of cell free BALF showed a large increase in a number of protein bands, including a 67 kDA band, in mice harvested 24 hours post $COCl_2$ exposure (FIG. 13C). Previous Western blotting studies [4] have shown that the 67 kDa band corresponds to plasma albumin. It should be noted that the pattern observed in SDS-PAGE gels was similar to that of plasma (far right two lanes in FIG. 13C), indicating complete breakdown of the alveolar barrier.

Figure 14A:
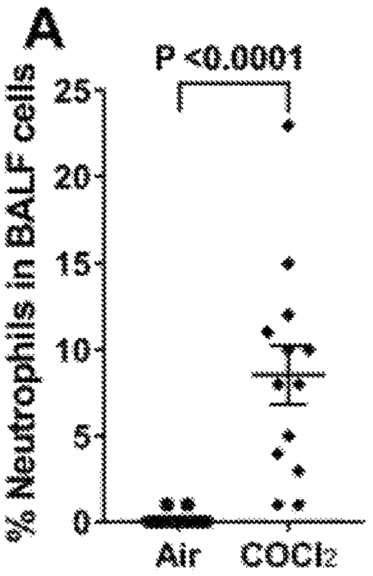
FIGS. 14A-14C show measurements of distal lung injury in mice exposed to $COCl_2$.
Figure 14B:
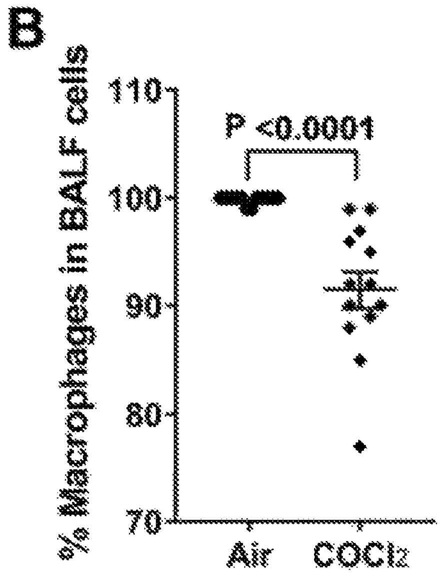
Figure 14C:
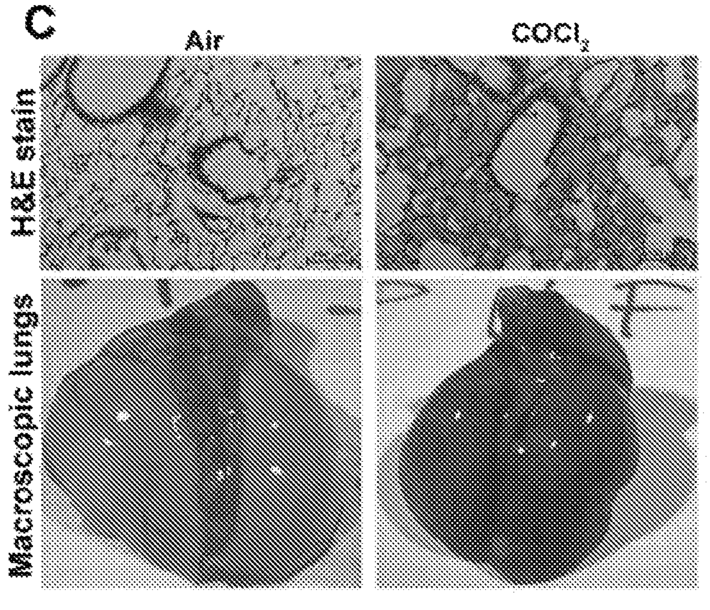

The total cell count remained unchanged at both 3 and 24 h post exposure (data not shown). However at 24 h post exposure there was a significant increase of the %-neutrophils in the BAL (FIG. 14A) [% of neutr.=0.14±0.1 [15]; 8.5±1.8 [19]; X±SEM; (number of mice) for air and 20 ppm $COCL_2$ respectively] and a concomitant decrease of the % of alveolar macrophages (FIG. 14B) [% mac.=100±0.1 [15]; 91±1.8]. In addition, the lungs were fixed with formalin at a 25 $cmH_2O$ constant pressure. Thin sections were cut from all lobes, fixed and stained with hematoxylin and eosin. H&E staining of the lungs of mice sacrificed at 24 h post $COCl_2$ (20 ppm for 10 min) showed that most alveoli were filled with exudate exhibiting eosin staining, indicative of high protein content (FIG. 14C), consistent with data shown in FIGS. 13A-13C. In contrast, H&E stains of the distal lung regions of mice exposed to air, were free of exudate and showed normal architecture. Macroscopic examination of the lungs of $COCl_2$ exposed mice showed severe hemorrhage (FIG. 14C).

Figure 15A:
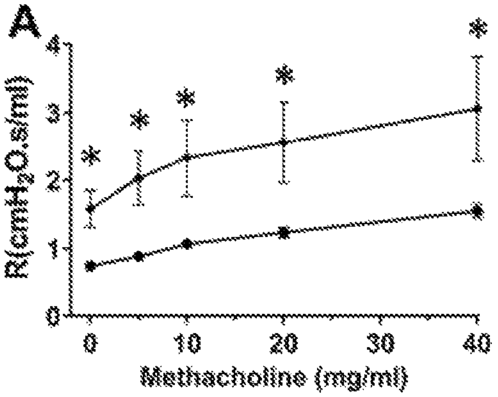
FIGS. 15A-15B show measurements of airway resistance and elastance in mice exposed to $COCl_2$.
Figure 15B:
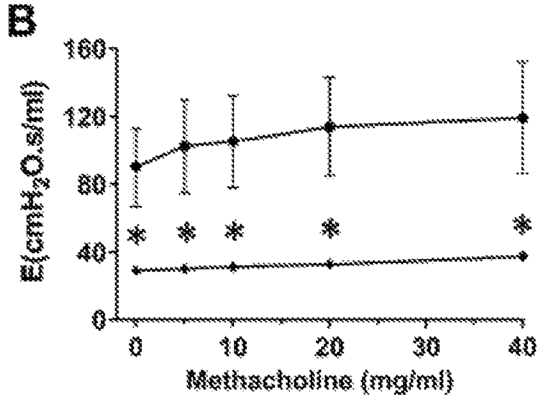

Exposure to 20 ppm $COCl_2$ increases airway resistance. Male only C57BL/6 mice were exposed to either air or $COCl_2$ (20 ppm for 10 min) and returned to room air for 24 h. They were then anesthetized and connected to a flexi Vent for measurements of airway resistance or elastance. Measurements of airway resistance and elastance with flexi Vent showed a large increase of baseline airway resistance and a concomitant decrease of dynamic elastance at 24 h post exposure (FIGS. 15A-15B). Following methacholine challenge, airway resistance (FIG. 15A) and elastance (FIG. 15B) changed similarly in both $COCl_2$ and air exposed mice; these data indicate that in spite of the large increase of baseline airway resistance, airways did not become hyperreactive following exposure to $COCl_2$, in contrast to what is seen in $Cl_2$ and $Br_2$ exposed mice. Surprisingly, Newtonian airway resistance, an index of injury to upper airways, did not change in the $COCl_2$ group indicating that the increase of airway resistance was mainly due to damage to small airways.

Figure 16A:
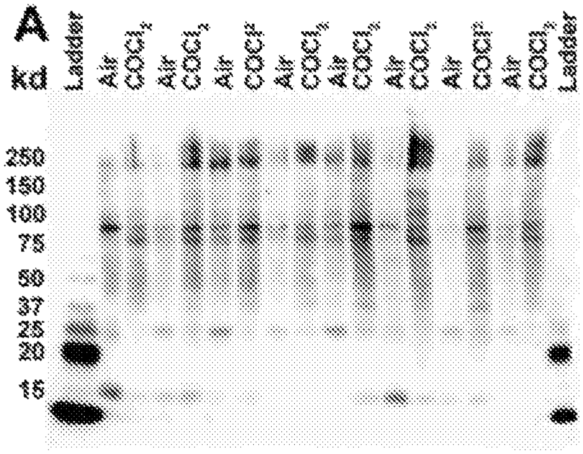
FIGS. 16A-16B show carbonyl adducts are increased in RBC ghosts post $COCl_2$ exposure.
Figure 16B:
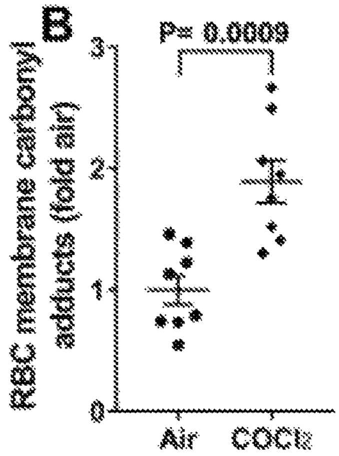

Exposure to $COCl_2$ damages red blood cells and causes hemolysis. First, RBC membranes were analyzed for the presence of oxidative damage (FIGS. 164-16B). For these studies, RBC were collected and membranes prepared as outlined in Methods. The measurement of membrane associated carbonyl adducts (FIGS. 164-16B) from RBC collected 24 h post exposure to $COCl_2$ (20 ppm, 10 min) showed significantly higher levels of oxidation (FIGS. 164-16B) of a 90-95 kDa protein as well as a number of higher molecular weight proteins [fold increase over air: 1.9±0.2 (8)]. Due to the limited repertoire of proteins in RBC membrane, the 90-95 kDa protein is likely to be band 3 [30]; notice that both 4.1a and 4.1b bands are clearly visible and their ratio is about 1:1 in most of the preparation, as previously reported [31]; the high molecular species are likely to be ankyrin and spectrin. SDS-PAGE of RBC ghosts revealed no difference in total levels of these proteins (data not shown).

Figure 17A:
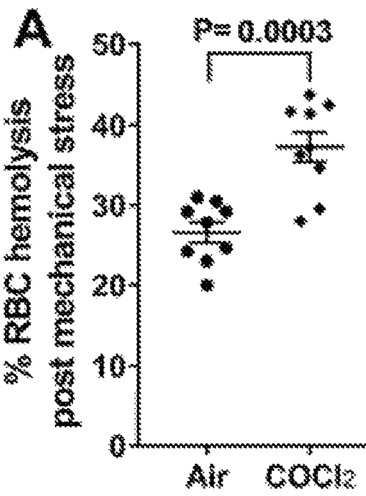
FIGS. 17A-17D show $COCl_2$ exposure increases RBC fragility in mice.
Figure 17B:
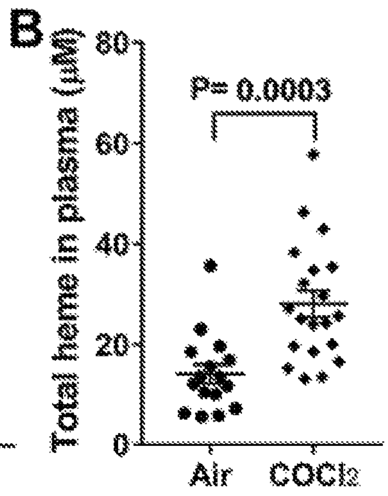
Figure 17C:
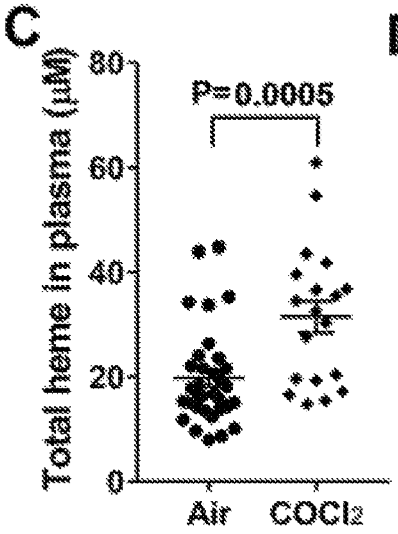
Figure 17D:
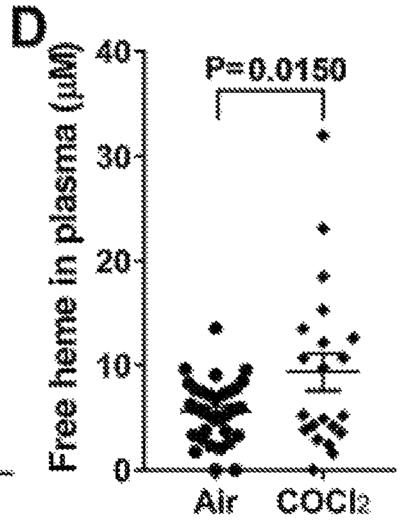

Next, to determine RBC fragility in mice, an equal number of male and female mice were sacrificed 24 h post exposure to either air or $COCl_2$ (20 ppm for 10 min). Blood was withdrawn from the left ventricle and plasma separated. RBCs from these mice were washed thoroughly to remove free heme; RBC suspensions of 1.0% hematocrit along with 4 mm solid glass beads (Pyrex) in DPBS were rotated 360° for 2 h at 24 rpm at 37° C. The hemoglobin released from the RBCs during rotation was transferred into a new tube and centrifuged at 13,400 g for 4 min and the absorbance of the supernatant were recorded at 540 nm. The analysis of RBC fragility showed that exposure to mechanical stress (rotation of RBCs with glass beads for 2 h) caused significantly more hemolysis in the RBCs obtained from the mice exposed to $COCl_2$ (20 ppm for 10 min) than the air exposed mice (FIG. 17A). Next, total levels of non-encapsulated heme were measured using an ELISA method which does not discriminate between free heme and heme bound to hemoglobin. There was a doubling of non-encapsulated heme at 24 h post 20 ppm $COCl_2$ for 10 min (FIG. 17B), [Total heme (mM)=14±2 [22]; 28±2.7 [23]; X±SEM; (number of mice) for air and 20 ppm $COCl_2$ respectively]. Measurements of non-encapsulated heme using a spectrophotometric technique followed by spectra deconvolution revealed a similar increase in this variable FIG. 17C) [Total heme (mM)=20±1.6 [24]; 31±3.1 [25]; X±SEM; (number of mice) for air and 20 ppm $COCL_2$ respectively]. Using the latter method, it was determined that, at 24 h post-exposure to 20 ppm $COCl_2$ for 10 min, approximately 25-30% of the non-encapsulated heme existed as free heme, formed most-likely by the oxidation of hemoglobin (FIG. 17D) (Free Heme (mM)=5.6±0.5 [24]; 9.3±1.8 [25]).

Figure 18A:
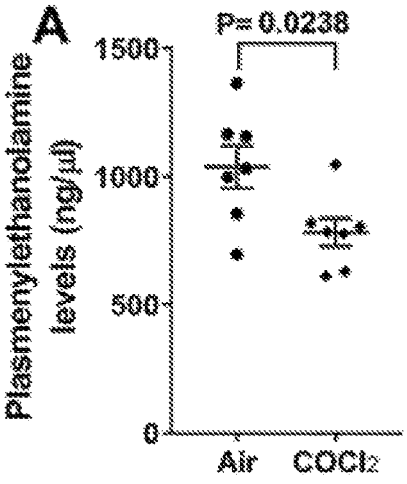
FIGS. 18A-18B show the measurement of plasmalogens and their breakdown product in $COCl_2$ exposed mice.
Figure 18B:
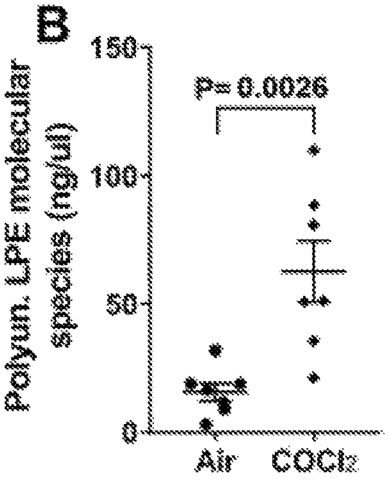

Exposure to $COCl_2$ damages plasmalogens. Previous data show that the halogens $Cl_2$ and $Br_2$ interact with lung plasmalogens resulting in the formation of halogenated lipids (fatty acids and aldehydes), which cause extensive injury to RBCs and distant targets [26-28]. To measure plasmalogens and their breakdown product in $COCl_2$ exposed mice, an equal number of male and female mice were sacrificed 24 h post exposure to either air or 20 ppm $COCl_2$ for 10 min. Plasma was subjected to a modified Bligh-Dyer lipid extraction in the presence of lipid class internal standards including 1-0-tetradecanoyl-sn-glycero-3-phosphoethanolamine and 1,2-ditetradecanoyl-sn-glycero-3-phosphoethanolamine. Lipid extracts were diluted in methanol/chloroform (1/1, v/v) and molecular species were quantified using electrospray ionization mass spectrometry on a triple quadrupole instrument employing shotgun lipidomics methodologies. Exposure of mice to $COCl_2$ (20 ppm for 10 min) resulted in a significant decrease of plasmenylethanoamine (FIG. 18A) [PE (ng/±μl)=1038±89 [29]; 783±58 [29]] and an increase of its breakdown product, polyunsaturated lysophosphatidylethanolamine (FIG. 18B) [LPE (ng/μl)=16±3.7; 62±13 for air and 20 ppm $COCL_2$ respectively].

Example 3: Reactive Species Generated by Heme Impair Alveolar Epithelial Sodium Channel Function in Acute Respiratory Distress Syndrome In this working example, it is shown that cell-free heme (CFH) and chlorinated lipids (formed by the interaction of halogen gas, $Cl_2$, with plasmalogens) are increased in the plasma of patients exposed to $Cl_2$ gas. Ex vivo incubation of red blood cells (RBC) with halogenated lipids caused oxidative damage to RBC cytoskeletal protein spectrin, resulting in hemolysis and release of CFH. Patch clamp and short circuit current measurements revealed that CFH inhibited the activity of amiloride-sensitive epithelial $Na^+$ channel (ENaC) and cation sodium ($Na^+$) channels in mouse alveolar cells and trans-epithelial $Na^+$ transport across human airway cells with $EC_{50}$ of 125 nM and 500 nM, respectively. Molecular modeling identified 22 putative heme-docking sites on ENaC (energy of binding range: 86-1563 kJ/mol) with at least 2 sites within its narrow transmembrane pore, potentially capable of blocking $Na^+$ transport across the channel. A single intramuscular injection of the heme-scavenging protein, hemopexin (4 μg/kg body weight), one-hour post halogen gas exposure, decreased plasma CFH and improved lung ENaC activity in mice. These results suggest that CFH mediated inhibition of ENaC activity may be responsible for pulmonary edema post inhalation injury.

Materials and Methods

Humans. The study was approved by the University of Alabama at Birmingham Institutional Review Board (IRB Protocol 300002065 and 300000860) and the Saint Louis University Institutional Review Board (IRB 9952). Demographic information was recorded on all volunteers and blood was drawn from the peripheral vein. Plasma was isolated from the blood, aliquoted, and stored at −80° C. using Freezerworks Sample Inventory Management software (Dataworks Development, Inc, Mountlake Terrace, WA, USA). No samples had undergone freeze-thaw cycles prior to use in the study.

Animals. Adult male C57BL/6 mice (20-25 g) were bought from Charles River, non-Frederick/NCI. All mice used in the study were males. All mice were raised under a 12-h dim light/12-h dark cycle with access to a standard diet and tap water ad libitum. Euthanasia protocol based on intraperitoneal injections of ketamine and xylazine was used in the study for mice to minimize pain and distress. All animal care and experimental procedures were approved by the Institutional Animal Care and Use Committee at the University of Alabama in Birmingham.

Exposure to halogen gas. Mice were exposed to $Br_2$ gas (600 ppm) or $Cl_2$ gas (400 ppm) in a cylindrical glass chamber for 30 min, as previously described [8, 27]. Control mice were exposed to room air in the same experimental conditions as $Br_2$ or $Cl_2$ exposed mice. Exposures were performed with two mice in the same chamber at any one time, and all exposures were performed between 6:00 a.m. and 12:00 p.m. Tanks were replaced when the pressure in the tanks reached 500 psi. In each case, immediately following exposure, mice were returned to room air. All experiments involving animals were conducted according to protocols approved by the UAB IACUC.

Treatment of animals with hemopexin. Adult male C57BL/6 mice were exposed to $Br_2$ gas (600 ppm), $Cl_2$ gas (400 ppm), or air in a cylindrical glass chamber for 30 min, as described above. Following exposure, mice were returned to room air and then 1 h later, mice were treated with an intramuscular injection of either saline or purified human hemopexin (4 mg/kg body weight, dissolved in saline) (Product No. 16-16-080513-LEL; Athens Research and Technology, Athens, GA). All experiments involving animals were conducted according to protocols approved by the UAB IACUC.

Measurement of Br-lip. Mice were euthanized at various times post-$Br_2$ gas exposure using a mixture of ketamine/xylazine (200/10 mg/kg) administered by intraperitoneal injection. Blood was collected via cardiac puncture, lungs were excised, and urine was collected from the bladder. Blood was centrifuged at 6000 rpm for 5 min to obtain the plasma fraction. Lungs, urine, and plasma samples were flash-frozen in liquid nitrogen and stored at −80° C. In some mice, the lungs were lavaged, and the recovered bronchoalveolar lavage fluid (BALF) was centrifuged immediately at 3000 g for 10 min to pellet the cells. Supernatants were flash-frozen. All samples were shipped overnight on dry ice to Dr. Ford at St. Louis University. Br-FALD was measured following conversion to its pentafluorobenzyl oxime using negative ion-chemical ionization GC/MS as previously described [32]. Free, esterified, and total (free+esterified) Br-FA were measured as previously described for chlorine by LC/MS following Dole extraction [27,33]. Total lipids were measured by LC/MS after base hydrolysis and esterified Br-FA calculated by subtracting free lipids from total lipids. Extractions were performed using 25 μl of plasma spiked with 517 fmol of 2-chloro-[$d_4$-7,7,8,8] palmitic acid (2-[$d_4$]CIPA) as the internal standard, and for lungs, 40-50 mg of tissue was used, spiked with 20 pmol of 2-[$d_4$]CIPA internal standard as mentioned earlier for Cl-FAs [27].

Measurement of glutathione adducts of 2-Br-PALD. Plasma, lung, BALF, and urine samples were analyzed as previously described [27]. Briefly, 25 µl of plasma, RBCs (diluted with 75 µl of water), BALF or urine were spiked with 90 fmol of [$d_4$]HDAGSH and 10 mg of pulverized lung tissue was spiked with 900 fmol [$d_4$]HDAGSH. Plasma, lung, RBCs, BALF, and urine were then extracted according to a similar Bligh and Dyer method as described for the Cl-lipids [33]; however, the aqueous layer was saved as the GSH adducts partition to the aqueous layer. The organic layer was subsequently washed with 1 volume of methanol: water (1:1 v:v) and combined with the previous aqueous layer. The combined aqueous layers were diluted with 1/3 vol of water and extracted on a Strata-X followed by ESI-LC/MS/MS quantitation, as previously described [34].

Ex Vivo RBC mechanical fragility. Blood was obtained from adult C57BL/6 mice in the presence of an anticoagulant and incubated with 1 µM each of Br-lip (16BrFA, 16BrFALD, 18BrFA, 18BrFALD), Cl-lip (16CIFA, 16CIFALD, 18CIFA, or 18CIFALD) or the corresponding non-halogenated lipids as vehicle (16 and 18 carbon palmitic acid or palmitaldehyde) for 4 h with rotations. In a separate set of experiments, blood was obtained from mice exposed to $Br_2$, $Cl_2$, or air in the presence or absence of treatment with hemopexin as mentioned above. Plasma was separated and the RBCs were washed with isotonic solution 3 times to remove traces of plasma. RBCs were then re-suspended in normal saline. The RBC suspensions along with 4×4 mm glass beads (Pyrex) in DPBS were then rotated 360° for 2 h at 24 rpm at 37° C. The RBC suspension was then centrifuged at 13,400 g for 4 min to separate the intact or damaged cells from the supernatant containing heme/hemoglobin from the lysed cells during this mechanical stress. Free heme/hemoglobin was transferred into a new tube and the absorbance of the supernatant recorded at 540 nm as described earlier [35]. Subsequently, one hundred percent hemolysis of RBCs was achieved by treating them with 1% Triton x-100 solution. The fractional hemolysis of the sample was then obtained by dividing the optical density of the sample by the optical density of the 100% hemolyzed sample.

Measurement of protein carbonyl adducts in RBC ghosts. RBCs were separated from the plasma and hemolyzed with 20 mM hypotonic Hepes Buffer. The mixture was centrifuged at 14,000 g for 20 min and RBC pellet was dissolved in RIPA buffer (Thermo Fisher Scientific, MA). The protein was quantified by the BCA method and equal amounts of proteins (10 µg) were loaded into a 4-20% gradient gel and proteins were separated and stained with Amido Black (Sigma-Aldrich, St Louis, MS). The presence of protein carbonyl adducts in RBC ghosts were assessed using the Oxyblot protein oxidation detection kit (Product number: S7150, EMD Millipore, Billerica, MA), according to the manufacturer's protocol. Briefly, the carbonyl groups in the protein side chains were derivatized to 2,4-dinitrophenylhydrazone by reacting with 2,4-dinitrophenylhydrazine. Precisely, 10 µg of protein was used for each sample, and the 2,4-dinitrophenol-derivatized protein samples were separated by polyacrylamide gel electrophoresis, as described previously [8]. Polyvinylidene fluoride membranes were incubated for 1 h in the stock primary antibody (1:150 in 1% PBS/TBST buffer), and after washing, for 1 h in the stock secondary antibody (1:300 in % PBS/TBST buffer). Membranes were washed 3×in TBST and visualized. The abundance of protein carbonylation was assessed by densitometry of each lane and normalization for each lane protein loading was done by SDS PAGE gel quantification.

Lung slices preparation. Eight-week-old C57BL/6 male mice (~20-25 g body weight) were purchased from The Jackson Laboratory (Bar Harbor, ME). Lung slices were prepared as previously described [36]. The right lower lobes were dissected, attached to tissue holder using cyanoacrylate adhesive gel, and sectioned into slices of 200 µm thick. The slices were transferred to a six-well plate containing Dulbecco's Modified Eagle's Medium without serum, supplemented with penicillin-streptomycin, and allowed to recover at 37° C. in a humidified environment of 95% air/5% $CO_2$ for 2-3 h.

ENaC single channel activity in AT2 cells in situ. A lung slice was transferred to the recording chamber on the stage of an upright Olympus microscope EX51WI (Olympus, Pittsburgh, PA). Single-channel activity in AT2 cells was recorded using the cell-attached mode of the patch clamp technique. AT2 cells were identified by the presence of scattered green fluorescence after incubation with Lysotracker Green (catalogue number DND-26; Invitrogen, Eugene, OR).

Human bronchial epithelial cells isolation, culture, and short circuit currents recording. Human bronchiolar epithelial cells (HBECs) were provided by UAB CF Center upon request. Cells were isolated from human lungs not used for transplantation, HBECs were seeded onto permeable support and allowed to form confluent monolayers (3-4 weeks in culture). Tight monolayers were mounted in an Ussing chambers system and short circuit currents were monitored and recorded using an amplifier (physiologic instruments, San Diego, CA). Monolayers were bathed in Ringer solution bubbled with 95% air 5% $Co_2$. Hemin (ferric chloride heme, mentioned as heme throughout the text), dissolved in DMSO, was added to both sides of monolayers.

ENaC expression in *Xenopus* oocytes. Oocytes isolated from *Xenopus laevis* frogs, were injected with cRNAs encoding for wild-type α, β, γ-hENaC (8.4 ng each), dissolved in 50 nl of RNase-free water per oocyte, and incubated in half-strength L-15 medium for 24-48 h. Whole-cell cation currents were measured by the two-electrode voltage clamp. A TEV 200 voltage clamp amplifier (Dagan Corp., Minneapolis, MN) was used hold oocytes membrane potential at −40 mV. Current-voltage (I-V) relationships were obtained by stepping the Vm from −140 mV to +60 mV in 20 mV increments. Sampling protocols were generated by pCLAMP 9.0 (Molecular Devices, Union City, CA). Currents were sampled at the rate of 1 kHz, filtered at 500 Hz, and simultaneously stored electronically and displayed in real time. Hemin was diluted to the desired final concentration in ND96 and applied to the oocytes through the perfusion system at a rate of 1 ml/min.

Mass spectrometry. Sample Preparation. Samples were denatured in 1×final NuPAGE™ LDS Sample Buffer (Cat. #NP0007, Invitrogen), and the resultant enriched proteins were separated onto a NuPAGE™ 10% Bis-Tris Protein gel (Cat. #NP0315BOX, Invitrogen) at 200 V constant for 25 min. The gel was stained using a Colloidal Blue Staining Kit (Cat. #LC6025, Invitrogen) following manufacturer's instruction. Each gel lane was excised (two equal-sized fractions pertaining to spectrin alpha and beta molecular weights) and digested overnight at 37° C. with Pierce™ Trypsin Protease, MS Grade (Cat. #90058, Thermo Scientific) as per manufacturer's instruction. Digests were reconstituted in 0.1% FA in 5:95 ACN:ddH2O at ~0.1 µg/uL.

nLC-ESI-MS2 Analysis & Database Searches. Peptide digests (8 µL each) were injected onto a 1260 Infinity nHPLC stack (Agilent Technologies), and separated using a 100 μm I.D.×13.5 cm pulled tip C-18 column (Jupiter C-18 300 Å, 5 μm, Phenomenex). This system runs in-line with a Thermo Orbitrap Velos Pro hybrid mass spectrometer, equipped with a nano-electrospray source (Thermo Fisher Scientific), and all data were collected in CID mode. The nHPLC was configured with binary mobile phases that included solvent A (0.1% FA in ddH2O), and solvent B (0.1% FA in 15% ddH2O/85% ACN), programmed as follows; 10 min @5% B (2 μL/min, load), 60 min @5%-40% B (linear: 0.5 nL/min, analyze), 5 min @70% B (2 μL/min, wash), 10 min @0% B (2 μL/min, equilibrate). Following each parent ion scan (300-1200 m/z @60 k resolution), fragmentation data (MS2) was collected on the top most intense 15 ions. For data dependent scans, charge state screening and dynamic exclusion were enabled with a repeat count of 2, repeat duration of 30 s, and exclusion duration of 90 s.

The XCalibur RAW files were collected in profile mode, centroided and converted to MzXML using ReAdW v. 3.5.1. The data was searched using SEQUEST Version 27, rev. 12 (Thermo Fisher Scientific), which was set for two maximum missed cleavages, a precursor mass window of 20 ppm, trypsin digestion, variable modification P @−27.9949, R @−43.0534, K @−1.0316, T @−2.0157, C @57.0293, and M @15.9949. Searches were performed with a mouse-specific subset of the UniRefKB database.

Peptide Filtering, Grouping, and Quantification. The list of peptide IDs generated based on SEQUEST search results were filtered using Scaffold Version 4.8.9 (Protein Sciences, Portland Oregon). Scaffold filters and groups all peptides to generate and retain only high confidence IDs while also generating normalized spectral counts (N-SC's) across all samples for the purpose of relative quantification. The filter cut-off values were set with minimum peptide length of >5 AA's, with no MH+1 charge states, with peptide probabilities of >80% C.I., and with the number of peptides per protein >2. The protein probabilities were then set to a >99.0% C.I., and an FDR<1.0. Scaffold incorporates the two most common methods for statistical validation of large proteome datasets, the false discovery rate (FDR) and protein probability. In addition, for all PTM's, the exported Scaffold files were further analyzed within Scaffold PTM (Protein Sciences) where the use of assigned A-scores and localization C.I.'s allowed for filtering out potential false positive PTM assignments. Those PTM's that pass these filters were also manually checked for quality of fit.

Molecular modeling and heme docking. To determine potential mechanisms by which heme exposure impairs ENaC activity within few seconds, computer modeling using YASARA software was performed to simulate heme docking and binding to the known cryo-electron microscopy structure of ENaC (Protein Data Bank: 6BQN). The docking of the heme molecule to the ENaC structure was performed using AutoDock program developed at the Scripps Research Institute using the default docking parameters and point charges initially assigned according to the AMBER03 force field, and then damped to mimic the less polar Gasteiger charges used to optimize the AutoDock scoring function. The YASARA molecular modeling program was set up to determine the best 25 hits and determine their free energy of binding in kJ/mol.

Results

Figure 19A:
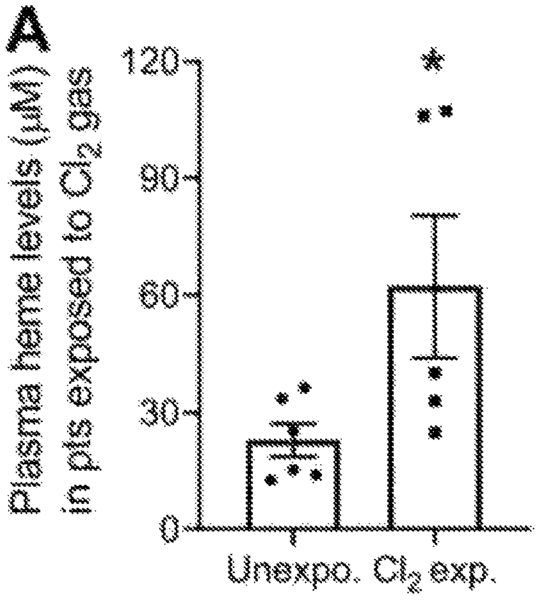
FIGS. 19A-19D show plasma cell-free heme (CFH) and chlorinated lipids are elevated in humans and mice exposed to $Cl_2$ gas.
Figure 19B:
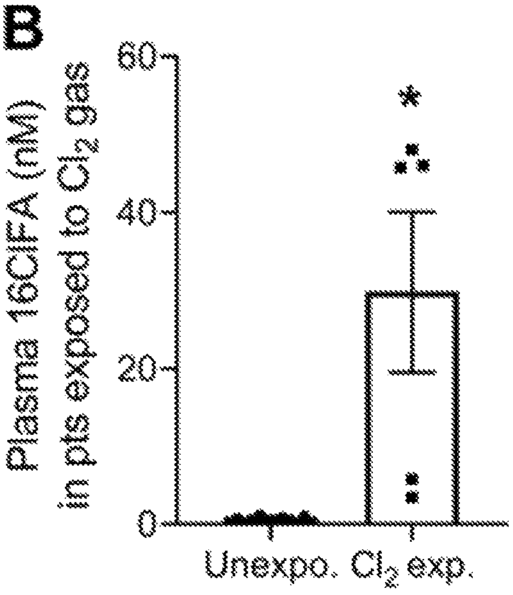
Figure 19C:
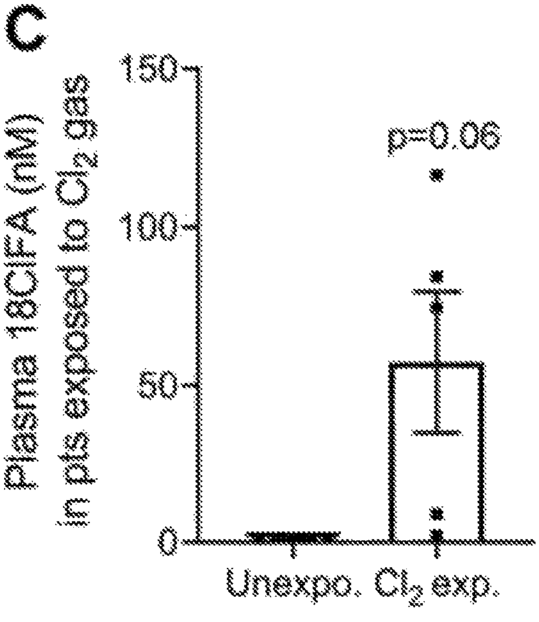
Figure 19D:
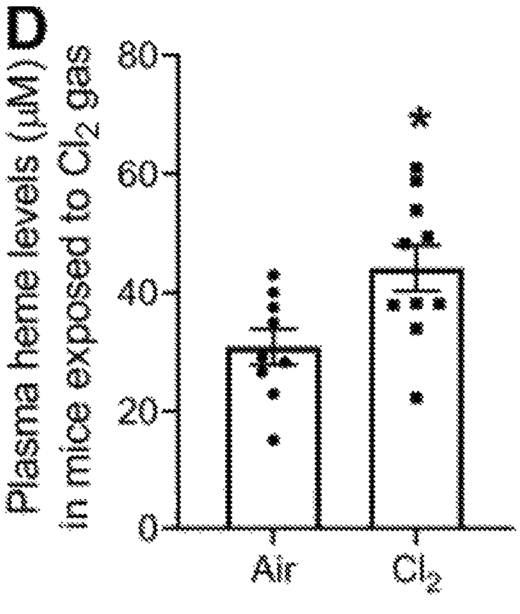

Cell-free heme (CFH) and chlorinated lipids are elevated in plasma of humans and animals exposed to $Cl_2$ gas. Plasma CFH was measured in 5 adult humans, which were admitted to the University of Alabama at Birmingham Emergency Department, post accidental exposure to $Cl_2$ gas at the Birmingham water treatment plant. The average age of exposed humans was 48 years with 80% of them being males. Blood was also collected from corresponding age and sex matched non exposed humans. As shown in FIG. 19A, plasma CFH levels were significantly increased in $Cl_2$ gas exposed patients compared to their sex- and age-matched non-exposed individuals. People exposed to $Cl_2$ gas also had elevated plasma levels of 16-carbon chlorinated fatty acid (CIFA) (FIG. 19B) and 18-carbon CIFA (FIG. 19C), as measured in plasma obtained from these individuals 3-6 h post exposure in the emergency room. These values were about 20-fold higher than those found in patients with sepsis [37]. Similarly, exposure of adult C57BL/6 male mice to $Cl_2$ gas (400 ppm, 30 min) increased plasma levels of CFH levels (24 h post exposure) (FIG. 19D).

Figure 20A:
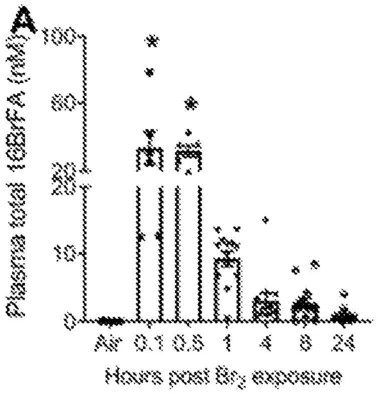
FIGS. 20A-20F show brominated fatty acids (BrFA) are elevated in plasma of $Br_2$ exposed mice.
Figure 20B:
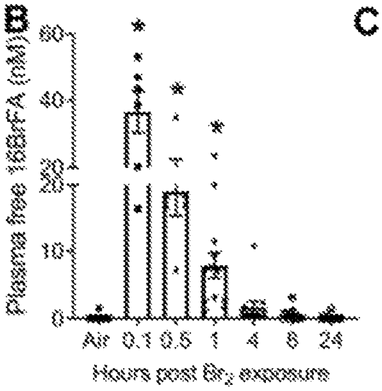
Figure 20C:
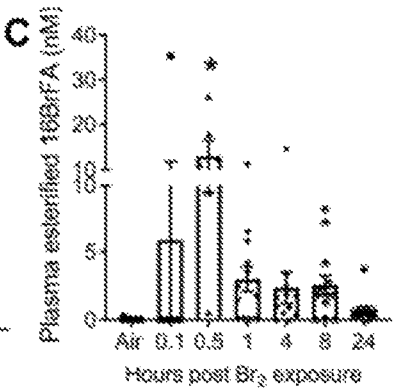
Figure 20D:
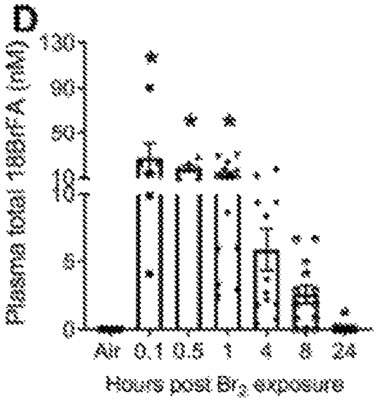
Figure 20E:
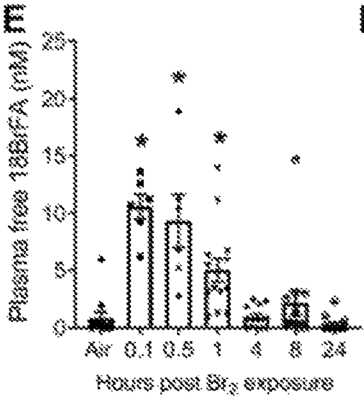
Figure 20F:
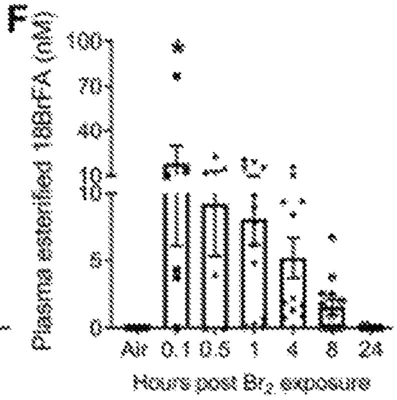
Figures 21A, 21B, 21C, 21D, 21E, 21F, 21G, 21H:
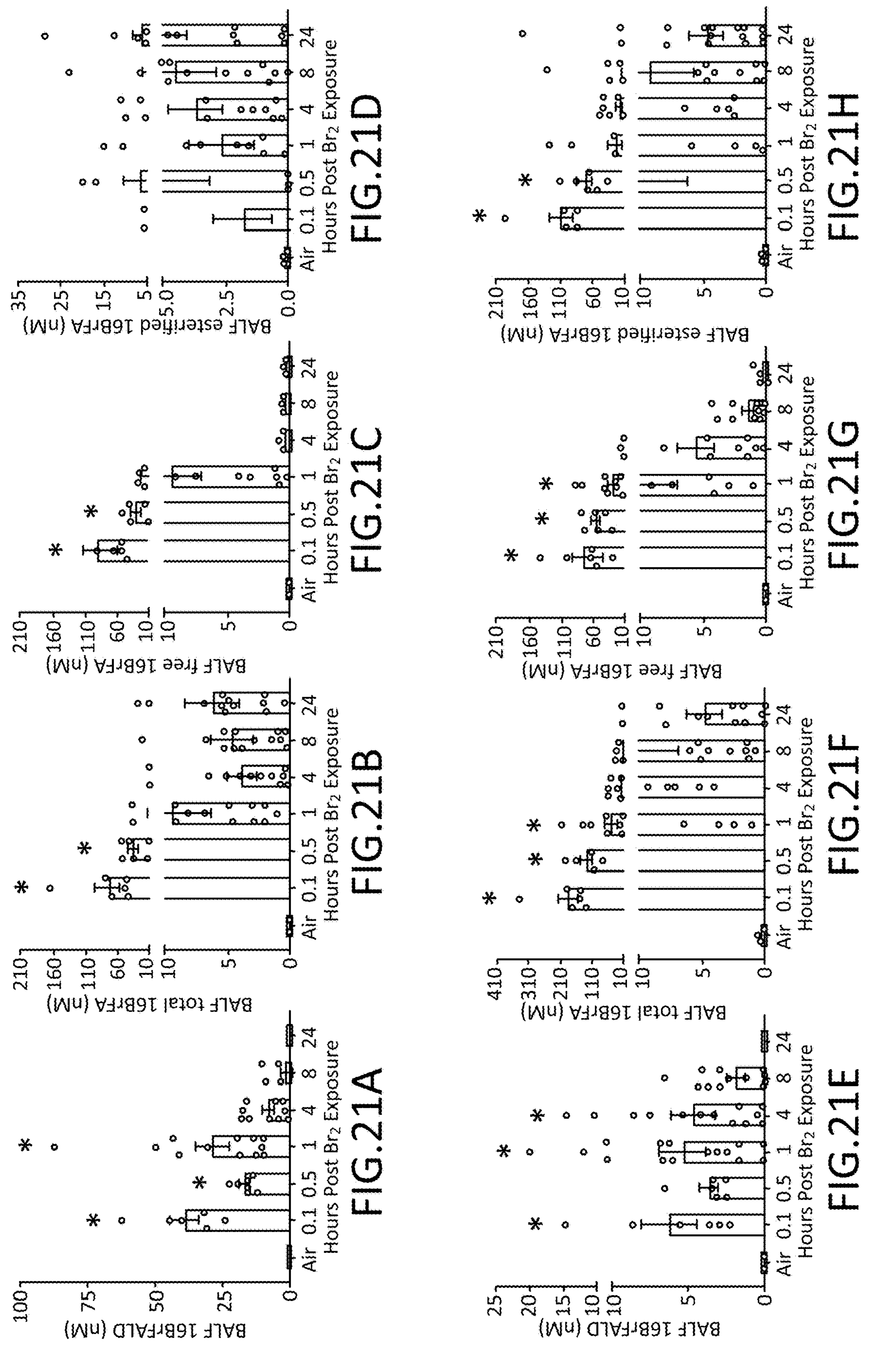
FIGS. 21A-21H show brominated fatty aldehyde (BrFALD) and fatty acids (BrFA) levels in broncholaveolar lavage fluid (BALF) of $Br_2$ exposed mice.
Figure 22A:
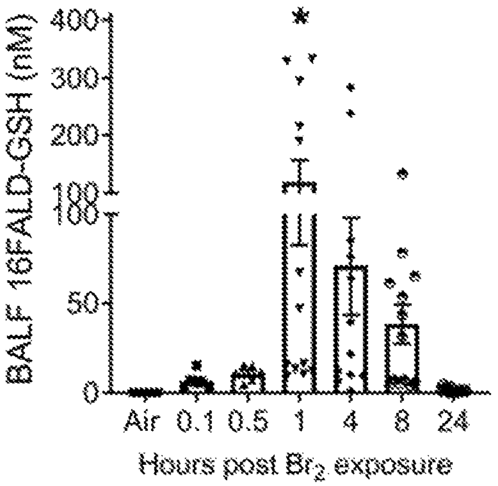
FIGS. 22A-22D show glutathionylated fatty aldehyde (FALD-GSH) levels in broncholaveolar lavage fluid (BALF) and peripheral lung tissue of $Br_2$ exposed mice.
Figure 22B:
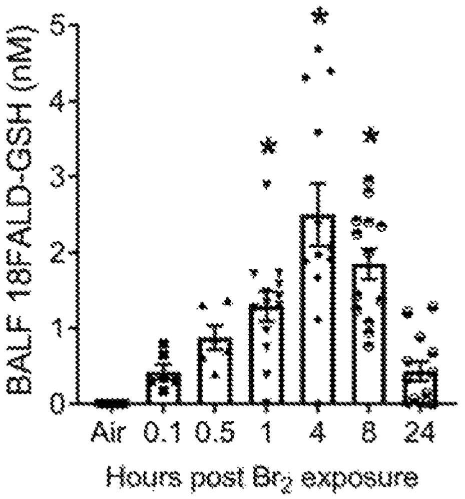
Figure 22C:
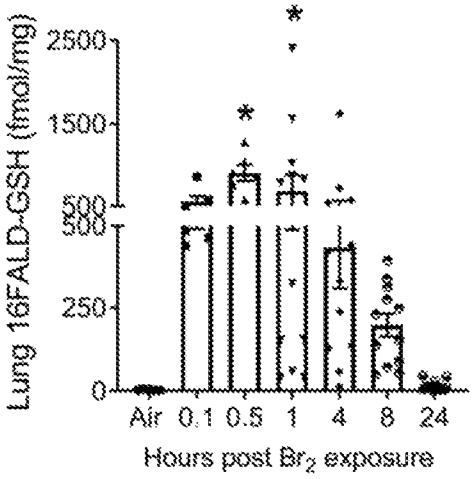
Figure 22D:
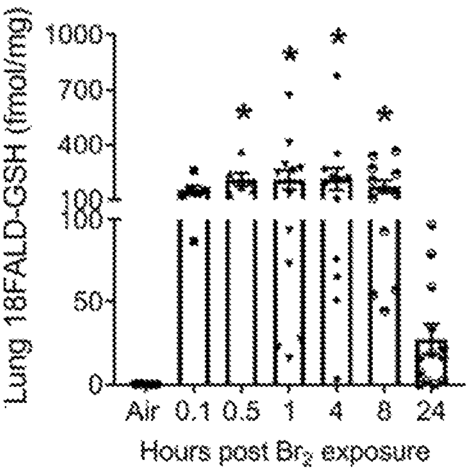
Figure 23A:
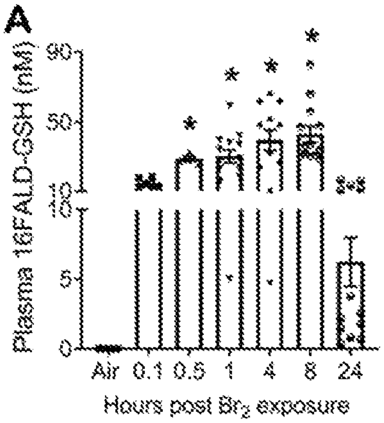
FIGS. 23A-23F show glutathionylated fatty aldehyde (FALD-GSH) levels in plasma, urine, and RBCs of $Br_2$ exposed mice.
Figure 23B:
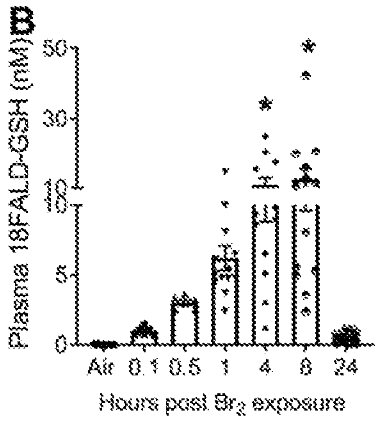
Figure 23C:
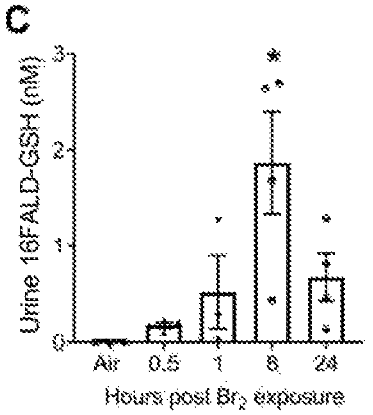
Figure 23D:
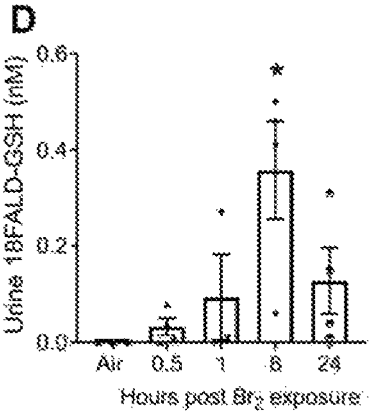
Figure 23E:
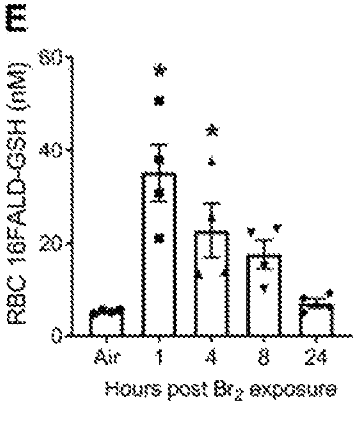
Figure 23F:
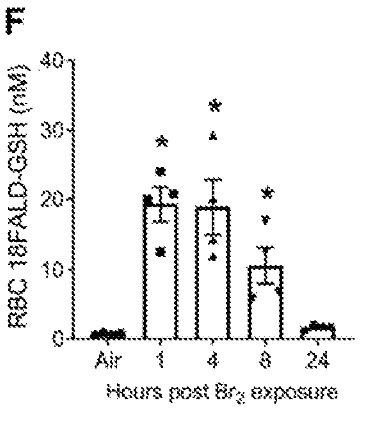

Halogenated lipids increase RBC hemolysis and cell-free heme. To explore the role of halogenated lipids in increasing RBC fragility and plasma CFH levels, it was determined whether exposure to other halogen gases, such as bromine ($Br_2$), also increases halogenated lipids. Male C57BL/6 mice were exposed to $Br_2$ gas (600 ppm, 30 min) and then returned to room air. Using LC/MS quantitation, it was found that plasma levels of 16-carbon (FIGS. 20A-20C) and 18-carbon (FIGS. 20D-20F) free- and esterified-brominated fatty acids (BrFA) were elevated in the exposed animals. Even at 24 h post exposure, the values of these variables were higher than those measured in patients with ARDS [37]. Elevated levels of brominated fatty aldehyde (Br-FALD) were also identified in the broncholaveolar lavage fluid (BALF) of exposed animals (FIGS. 21A and 21E). Aldehydes can be oxidized to fatty acids which may exist either in the esterified (bound) or free form. The BALF levels of esterified- and free-BrFA were increased in mice exposed to $Br_2$ (FIGS. 21B-21D, 21F-21H). The aldehydes can also react with the antioxidant, glutathione, which exists in mM concentrations in the lung epithelial lining and plasma, to form glutathionylated fatty aldehyde (FALD-GSH). High levels of 16- and 18-carbon FALD-GSH were found in the BALF (FIGS. 22A-22B), lung (FIGS. 22C-22D), plasma (FIGS. 23A-23B), urine (FIGS. 23C-23D), and RBCs (FIGS. 23E-23F), of $Br_2$ exposed mice. Because of their high reactivity, aldehydes could not be detected in the plasma in their natural configuration.

Figure 24A:
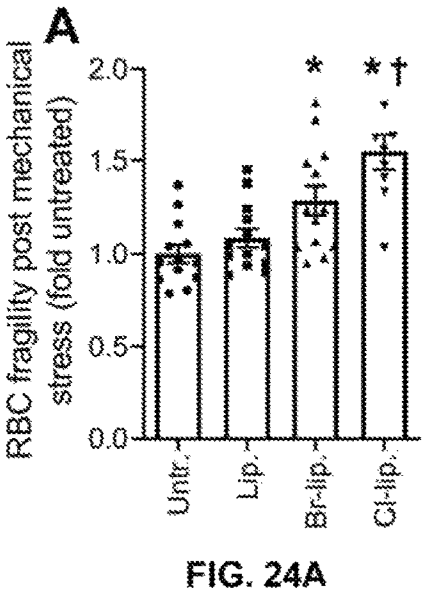
FIGS. 24A-24C show halogenated lipids increase carbonylation and hemolysis of RBC.
Figure 24B:
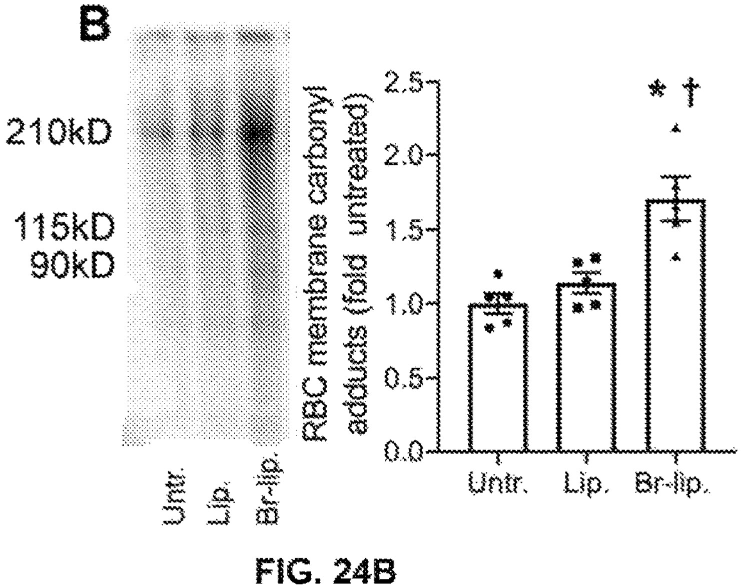
Figure 24C:
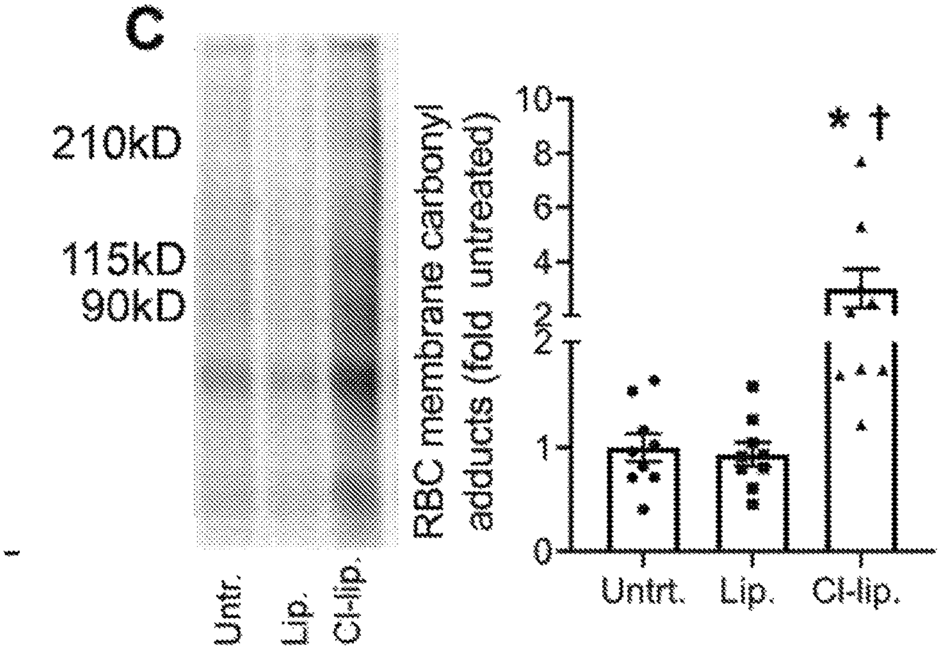

Next, to determine if halogenated lipids in the circulation or BALF are responsible for hemolysis and elevated CFH in plasma, RBCs were isolated from air exposed adult male C57BL/6 mice. The RBCs were then incubated ex vivo with the 16- and 18-carbon brominated or chlorinated lipids [fatty acid (FA) and fatty aldehyde (FALD), 1 μM each], or their corresponding vehicle (FA and FALD) for 4 h. The RBCs were then subjected to mechanical stress by mixing them with glass beads; the mixtures were shaken for 2 h. Data showed that both the brominated and the chlorinated lipids increased the hemolysis of RBCs significantly (FIG. 24A). In addition, the treatment of RBCs ex vivo with either brominated or chlorinated lipids resulted in increased oxidation of RBC membrane proteins, as indicated by elevated levels of carbonyl (aldehydes and ketones) adducts in protein side chains (FIGS. 24B and 24C).

To confirm the presence of carbonylation sites, as an indicator of oxidative stress and damage to RBC, adult male C57BL/6 mice were exposed to either $Br_2$ (600 ppm, 30 min) or $Cl_2$ (400 ppm, 30 min) gas. Twenty-four hours post exposure, blood was drawn from these mice and RBC ghosts were isolated. High resolution LCMS2 identified carbonylation changes for 6 putative amino acid sites within the RBC structural protein, spectrin alpha chain, and one site within spectrin beta chain, 24 h post-halogen exposure (shown in Table 2 below). The sites listed were all confirmed using a number of high confidence filters that included A-score and localization probabilities as indicated in the table and in more detail within the methods section. While exposure to both $Br_2$ and $Cl_2$ induced carbonylation, $Br_2$ appeared to have yielded a higher number of modifications indicating that it may be more damaging. Furthermore, each modification site appeared to be specific to the type of halogen gas, since no overlaps were found between the two exposures. The peptide marked with an asterisk in Table 2 was found to be modified at K1988, and was chosen to be highlighted for the LCMS2 results (FIGS. 25A-25B), where an example of MS2 spectra are also illustrated to point out how these modifications can be putatively identified. Together, the results indicate that carbonylation of RBC structural proteins may induce hemolysis and increase CFH post exposure to toxic insult.

TABLE 2

| Peptide Carbonylation Modification Site/Sequence | Tx | Localization Probability | A-score | Peptide Probability | Xcorr | m/z | Δppm |
|---|---|---|---|---|---|---|---|
| **Spectrin Alpha Chain, Erythocytic Protein** | | | | | | | |
| Spectrin Alpha Chain, Erythocytic Protein (P08032) | | | | | | | |
| (K640) QQDFEEELAVNEIMLNNLE***K*** (SEQ ID NO: 4) | $Cl_2$ | 100% | 1000 | 97% | 4.1 | 3 | -3.5 |
| (K1401) G***KC***DQVESWMVAR (SEQ ID NO: 5) | $Br_2$ | 100% | 1000 | 99% | 2.7 | 3 | -0.6 |
| (K1484) AL***K***EQLLTELGK (SEQ ID NO: 6) | $Br_2$ | 100% | 152 | 97% | 2.7 | 2 | -0.0 |
| (K1706) MNGVNERFENVQSLAAAHHE***K*** (SEQ ID NO: 7) | $Cl_2$ | 100% | 1000 | 99% | 3.7 | 3 | -2.9 |
| (K1988) LSEIAEL***K***DQLVAGEHSQAK* (SEQ ID NO: 8) | $Br_2$ | 100% | 165 | 100% | 5.5 | 3 | -1.7 |
| (K2259) MQHNLEQQIQA***K***DTIGVSEETLK EFSTTYK (SEQ ID NO: 9) | $Br_2$ | 100% | 25 | 96% | 3.3 | 5 | -7.1 |
| Spectrin Beta Chain, Erythocytic Protein (P15508) | | | | | | | |
| (K960) *VNNYCVDCEETS*___K___*WIMDK* (SEQ ID NO: 10) | $Br_2$ | 100% | 88 | 100% | 4.6 | 2 | 8.0 |

Figure 25A:
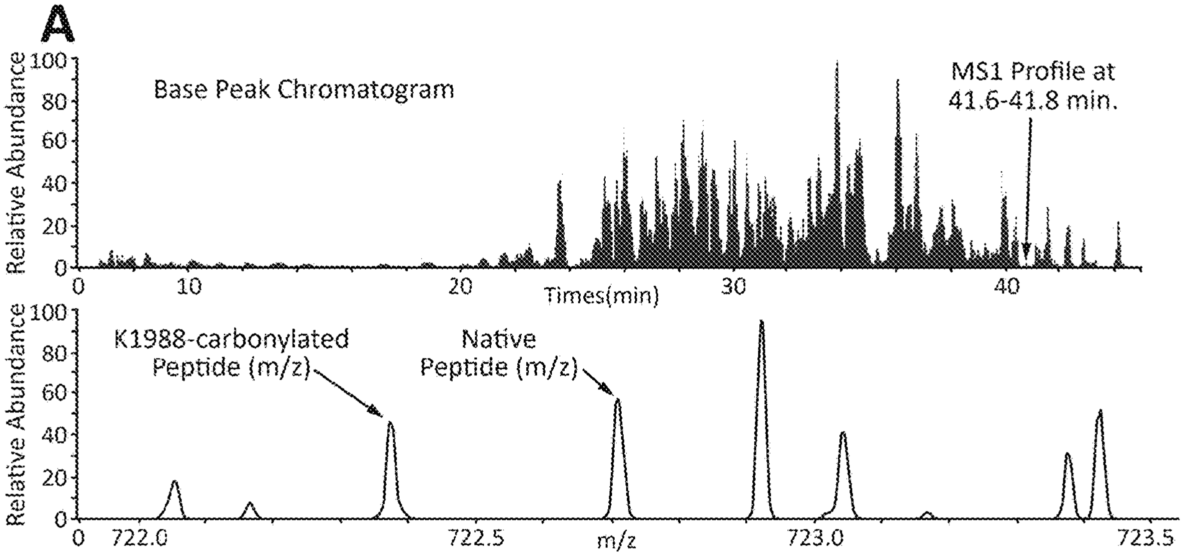
FIGS. 25A-25B show halogen gas exposure increased carbonylation of RBC spectrin A and B chains in mice.
Figure 25B:
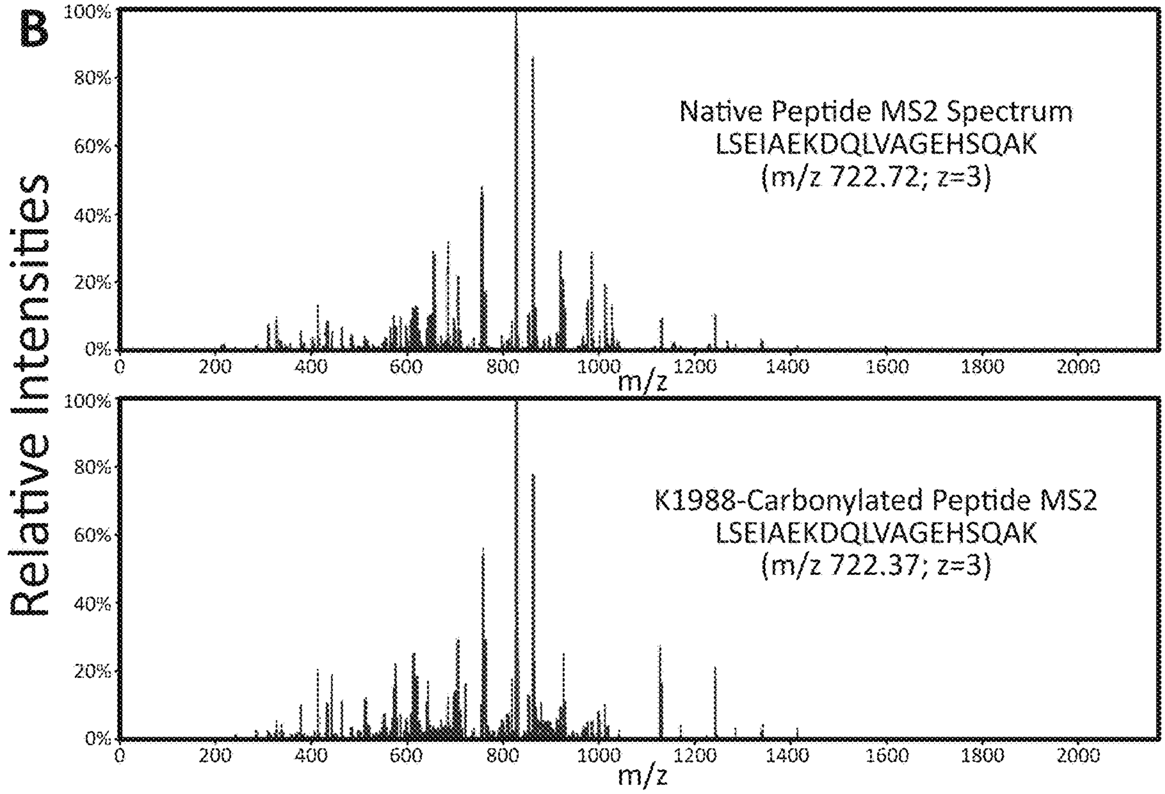

A representative LCMS2 analysis is illustrated with a focus on the tryptic peptide (LSEIAEL-KDQLVAGEHSQAK) (SEQ ID NO: 8) from spectrin alpha chain as highlighted in Table 2 above. FIG. 25A is an illustration of the LCMS base-peak chromatogram. FIG. 25B is the parent-ion spectra from the peptide peaks of interest using data dependent analysis at 41.7 min along with the resulting MS2 spectra for those ions representing the native (top) vs. Ox-K1988 (bottom) peptide of interest. The tables below, native peptide (Table 3), and Ox-K1988 peptide (Table 4) represent the corresponding fragments for the peptides from the MS2 spectra. The highlighted sections (b-ions/bold, y-ions/italic) represent those fragments that were observed in the MS2 spectra. The MS2 spectra illustrate that the two peptides (native vs. modified) fragment are nearly identical at charge state 3, with only 1-Da shifts that indicate K1988 is modified, which is made clear in the fragmentation tables. It's noted that all the 1-Da fragmentation shifts between the two tables are apparent below the b-8 ion and above the y-13 ion, both corresponding with AA #8 (K1988). MS was performed from RBC ghosts pooled from 4 to 5 animals.

TABLE 3

Native Peptide MS2 Fragment Table (LSEIAELKDQLVAGEHSQAK) (SEQ ID NO: 8)

| B | B Ions | B + 2H | B − NH3 | B − H2O | AA | Y Ions | Y + 2H | Y − NH3 | Y − H2O | Y |
|---|---|---|---|---|---|---|---|---|---|---|
| 1 | 114.1 | 57.5 | | | L | 2,166.1 | 1,083.6 | 2,149.1 | 2,148.1 | 20 |
| 2 | 201.1 | 101.1 | | 183.1 | S | 2,053.1 | 1,027.0 | 2,036.0 | 2,035.0 | 19 |
| 3 | 330.2 | 165.6 | | 312.2 | E | 1,966.0 | 983.5 | 1,949.0 | 1,948.0 | 18 |
| 4 | 443.3 | 222.1 | | 425.2 | I | 1,837.0 | 919.0 | 1,820.0 | 1,819.0 | 17 |
| 5 | 514.3 | 257.6 | | 496.3 | A | 1,723.9 | 862.5 | 1,706.9 | 1,705.9 | 16 |
| 6 | 643.3 | 322.2 | | 625.3 | E | 1,652.9 | 826.9 | 1,635.8 | 1,634.8 | 15 |
| 7 | 756.4 | 378.7 | | 738.4 | L | 1,523.8 | 762.4 | 1,506.8 | 1,505.8 | 14 |
| 8 | 884.5 | 442.8 | 867.5 | 866.5 | K | 1,410.7 | 705.9 | 1,393.7 | 1,392.7 | 13 |

TABLE 3-continued

Native Peptide MS2 Fragment Table
(LSEIAELKDQLVAGEHSQAK) (SEQ ID NO: 8)

| B | B Ions | B + 2H | B − NH3 | B − H2O | AA | Y Ions | Y + 2H | Y − NH3 | Y − H2O | Y |
|---|---|---|---|---|---|---|---|---|---|---|
| 9 | 999.5 | 500.3 | 982.5 | 981.5 | D | 1,282.6 | 641.8 | 1,265.6 | 1,264.6 | 12 |
| 10 | 1,127.6 | 564.3 | 1,110.6 | 1,109.6 | Q | 1,167.6 | 584.3 | 1,150.6 | 1,149.6 | 11 |
| 11 | 1,240.7 | 620.8 | 1,223.7 | 1,222.7 | L | 1,039.6 | 520.3 | 1,022.5 | 1,021.5 | 10 |
| 12 | 1,339.7 | 670.4 | 1,322.7 | 1,321.7 | V | 926.5 | 463.7 | 909.4 | 908.5 | 9 |
| 13 | 1,410.8 | 705.9 | 1,393.8 | 1,392.8 | A | 827.4 | 414.2 | 810.4 | 809.4 | 8 |
| 14 | 1,467.8 | 734.4 | 1,450.8 | 1,449.8 | G | 756.4 | 378.7 | 739.3 | 738.4 | 7 |
| 15 | 1,596.8 | 798.9 | 1,579.8 | 1,578.8 | E | 699.3 | 350.2 | 682.3 | 681.3 | 6 |
| 16 | 1,733.9 | 867.5 | 1,716.9 | 1,715.9 | H | 570.3 | 285.7 | 553.3 | 552.3 | 5 |
| 17 | 1,820.9 | 911.0 | 1,803.9 | 1,802.9 | S | 433.2 | 217.1 | 416.2 | 415.2 | 4 |
| 18 | 1,949.0 | 975.0 | 1,932.0 | 1,931.0 | Q | 346.2 | 173.6 | 329.2 | | 3 |
| 19 | 2,020.0 | 1,010.5 | 2,003.0 | 2,002.0 | A | 218.1 | 109.6 | 201.1 | | 2 |
| 20 | 2,166.1 | 1,083.6 | 2,149.1 | 2,148.1 | K | 147.1 | 74.1 | 130.1 | | 1 |

TABLE 4

K1988-Carbonylated Peptide Fragment Table
(LSEIAELKDQLVAGEHSQAK) (SEQ ID NO: 8)

| B | B Ions | B + 2H | B − NH3 | B − H2O | AA | Y Ions | Y + 2H | Y − NH3 | Y − H2O | Y |
|---|---|---|---|---|---|---|---|---|---|---|
| 1 | 114.1 | 57.5 | | | L | 2,165.1 | 1,083.1 | 2,148.1 | 2,147.1 | 20 |
| 2 | 201.1 | 101.1 | | 183.1 | S | 2,052.0 | 1,026.5 | 2,035.0 | 2,034.0 | 19 |
| 3 | 330.2 | 165.6 | | 312.2 | E | 1,965.0 | 983.0 | 1,948.0 | 1,947.0 | 18 |
| 4 | 443.3 | 222.1 | | 425.2 | I | 1,835.9 | 918.5 | 1,818.9 | 1,817.9 | 17 |
| 5 | 514.3 | 257.6 | | 496.3 | A | 1,722.9 | 861.9 | 1,705.8 | 1,704.9 | 16 |
| 6 | 643.3 | 322.2 | | 625.3 | E | 1,651.8 | 826.4 | 1,634.8 | 1,633.8 | 15 |
| 7 | 756.4 | 378.7 | | 738.4 | L | 1,522.8 | 761.9 | 1,505.8 | 1,504.8 | 14 |
| 8 | 883.5 | 442.2 | 866.5 | 865.5 | K-1 | 1,409.7 | 705.4 | 1,392.7 | 1,391.7 | 13 |
| 9 | 998.5 | 499.8 | 981.5 | 980.5 | D | 1,282.6 | 641.8 | 1265.6 | 1,264.6 | 12 |
| 10 | 1,126.6 | 563.8 | 1,109.5 | 1,108.6 | Q | 1,167.6 | 584.3 | 1,150.6 | 1,149.6 | 11 |
| 11 | 1,239.6 | 620.3 | 1,222.6 | 1,221.6 | L | 1,039.6 | 520.3 | 1,022.5 | 1,021.5 | 10 |
| 12 | 1,338.7 | 669.9 | 1,321.7 | 1,320.7 | V | 926.5 | 463.7 | 909.4 | 908.5 | 9 |
| 13 | 1,409.8 | 705.4 | 1,392.7 | 1,391.7 | A | 827.4 | 414.2 | 810.4 | 809.4 | 8 |
| 14 | 1,466.8 | 733.9 | 1,449.7 | 1,448.8 | G | 756.4 | 378.7 | 739.3 | 738.4 | 7 |
| 15 | 1,595.8 | 798.4 | 1,578.8 | 1,577.8 | E | 699.3 | 350.2 | 682.3 | 681.3 | 6 |
| 16 | 1,732.9 | 866.9 | 1,715.8 | 1,714.9 | H | 570.3 | 285.7 | 553.3 | 552.3 | 5 |
| 17 | 1,819.9 | 910.5 | 1,802.9 | 1,801.9 | S | 433.2 | 217.1 | 416.2 | 415.2 | 4 |
| 18 | 1,948.0 | 974.5 | 1,930.9 | 1,930.0 | Q | 346.2 | 173.6 | 329.2 | | 3 |
| 19 | 2,019.0 | 1,010.0 | 2,002.0 | 2,001.0 | A | 218.1 | 109.6 | 201.1 | | 2 |
| 20 | 2,165.1 | 1,083.1 | 2,148.1 | 2,147.1 | K | 147.1 | 74.1 | 130.1 | | 1 |

Figure 26A:
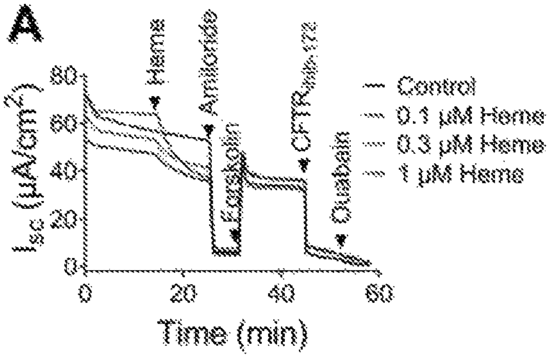
FIGS. 26A-26D show heme impairs short circuit current (Isc) in human bronchiolar epithelial cells.
Figure 26B:
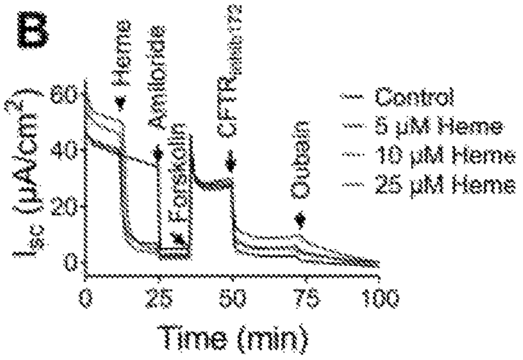
Figure 26C:
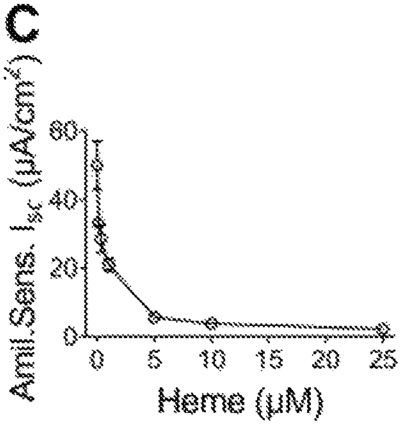

Heme impairs ENaC activity and $Na^+$ transport across lung epithelium. To determine the mechanism of CFH-induced lung edema, in the first series of experiments, it was determined whether heme inhibits active $Na^+$ transport across human bronchial epithelial cells (HBEC). Although, HBEC are not the primary cells, which are involved in the development of edema, they are $Na^+$ absorptive, and amiloride-sensitive ENaC-mediated ion transport has been detected in them [38] and are therefore an excellent substitute to study ENaC activity in human cells. Hemin (ferric chloride heme, mentioned just as heme throughout the text) was added in both the apical and basolateral compartments of Ussing chambers mounted with confluent monolayers. Data demonstrated that heme inhibited amiloride-sensitive, ENaC, but not forskolin-stimulated, GlyH-101-inhibited, CFTR, currents within few seconds post exposure (FIGS. 26A and 26B) with an $IC_{50}$ of about 500 nM (FIG. 26C). Transepithelial. resistance did not decrease with increased heme concentrations but even at a heme concentration of 10 μM, remained above 1500 Ohms*$cm^2$, indicating that the monolayers remained intact (data not shown).

Figure 26D:
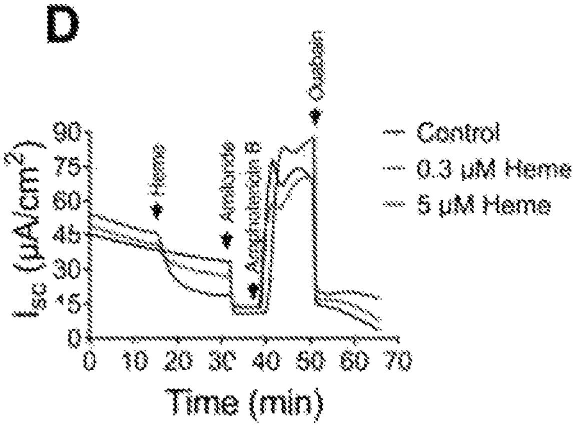
Figure 27A:
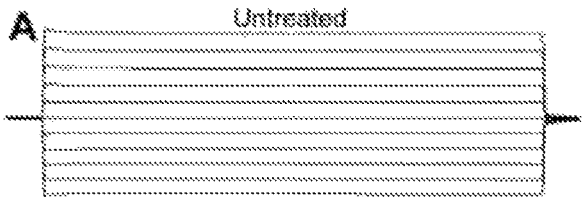
FIGS. 27A-27F show heme inhibits ENaC heterologously expressed in oocytes.
Figure 27B:
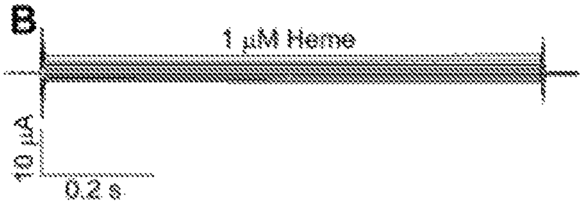
Figure 27C:
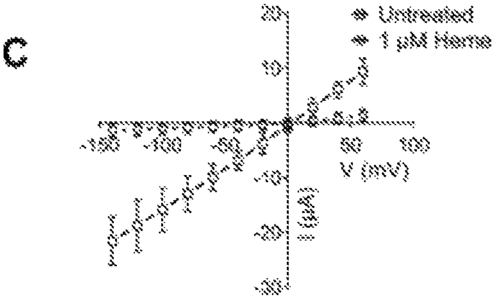
Figure 27D:
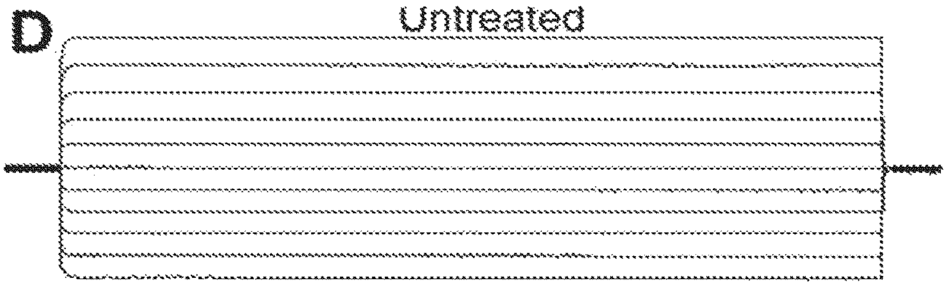
Figure 27E:
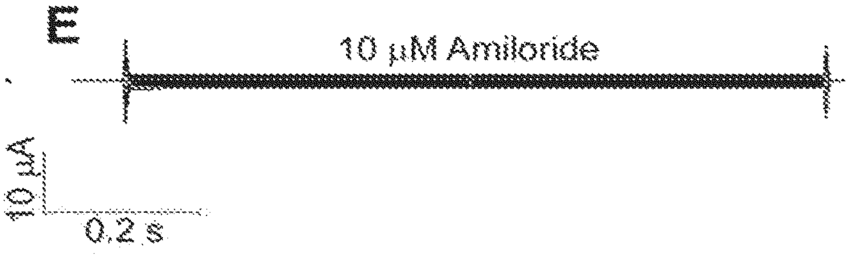
Figure 27F:
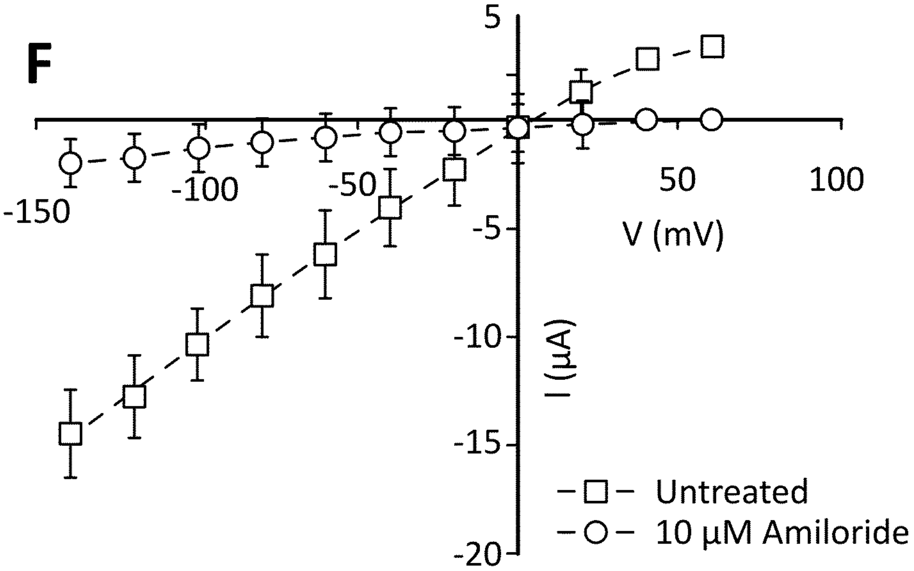

In the next series of experiments, the apical membranes of these monolayers were permeabilized and the ouabain-sensitive components of $Na^+/K^+$-ATPase activity were measured. Data showed that heme did not impair (alter) $Na^+/K^+$-ATPase function even at concentrations that totally inhibited ENaC activity (5-25 μM) (FIG. 26D). To further demonstrate that heme inhibited ENaC, *Xenopus* oocytes were injected with α-, β-, and γ-human ENaC cRNAs and current-voltage relationships were measured 48 h later. Oocytes injected with ENaC express significant amounts of $Na^+$ currents, 90% of which are inhibited by 10 μM amiloride [39]. Treatment of oocytes with 1 μM of heme immediately inhibited whole-cell $Na^+$ current by 80% (FIGS. 27A-27C). This decline in whole-cell $Na^+$ current was similar to amiloride-mediated inhibition of $Na^+$ current (FIGS. 27D-27F).

Figure 28A:
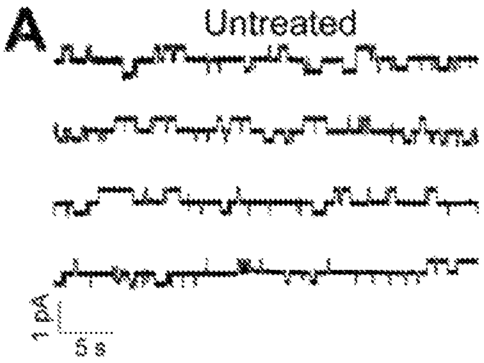
Figure 28B:
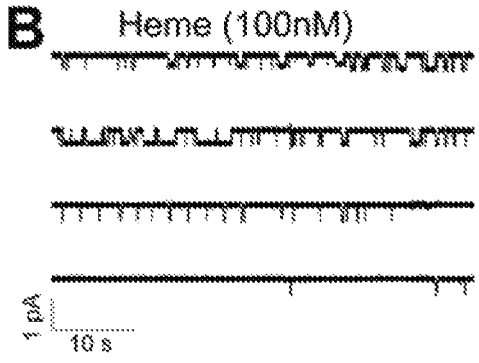
Figure 28C:
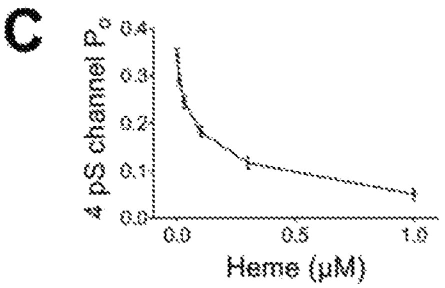
Figure 28D:
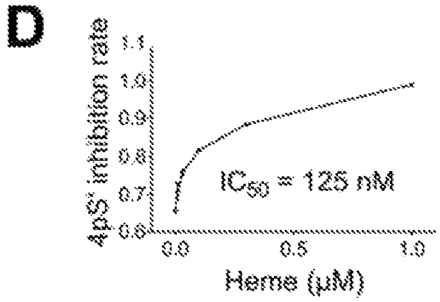
Figure 28E:
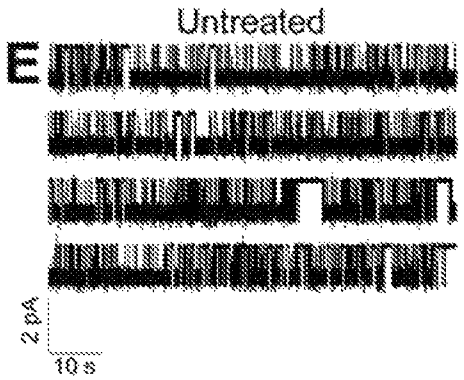
Figure 28F:
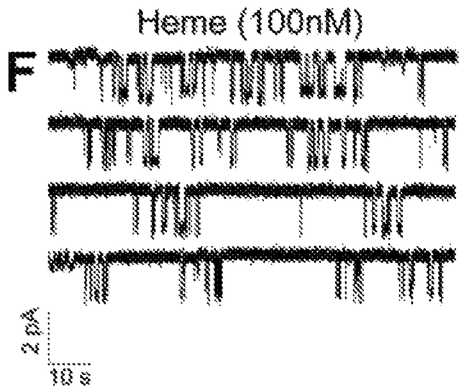

Further, ENaC activity was measured in alveolar type II (AT2) cells in-situ (lung slices) using the cell-attached mode of patch-clamp technique. Heme was added in the upper portion of the pipette which allowed for the recording of baseline ENaC activity prior to heme reaching the membrane patch under the pipette. Recordings from AT2 cells show the activity of two characteristic conductances: a 4 pS (pS) conductance of the highly $Na^+$ selective channel (FIG. 28A) and a 16 pS conductance of the non-selective cation channel (FIG. 28E). However, once heme diffused through the pipette and reached the membrane patch under the pipette tip, it decreased the open probabilities of both the 4 pS (FIGS. 28B and 28C) and 16 pS channels (FIGS. 28F and 28G) with an $IC_{50}$ of 125 nM for both 4 pS (FIG. 28D) and 16 pS (FIG. 28H).

To further understand the mechanism by which CFH instantaneously inhibits ENaC activity and $Na^+$ conductance across the lung epithelium, computer modeling was performed using YASARA software to identify potential heme binding sites and their potential ability to block $Na^+$ conductance. For this purpose, a recently developed cryo-electron microscopy structure of ENaC (Protein Data Bank: 6BQN) was used. The ion channel has large extracellular domains and a narrow transmembrane pore and the α:β:γ subunits are arranged in a counter-clockwise manner in a 1:1:1.stoichiometry. The software predicted 22 potential docking sites of heme on ENaC with the energy of binding ranging from 86 to 1563 kJ/mol. Close analysis of these docking sites showed that at least two heme-bonding sites are located within the ENaC transmembrane pore (energy of binding 390.5 and 313.2 kJ/mol) (FIGS. 29A and 29B), which can potentially block $Na^+$ transport through the channel. Together, these results demonstrated that heme mediated decrease in ENaC activity may be responsible for lung edema during ARDS.

Figure 30A:
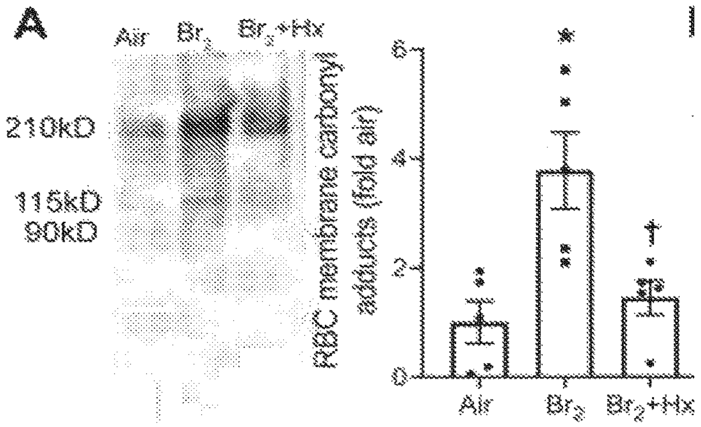
FIGS. 30A-30C show heme scavenging attenuates RBC membrane protein oxidation and RBC fragility.
Figure 30B:
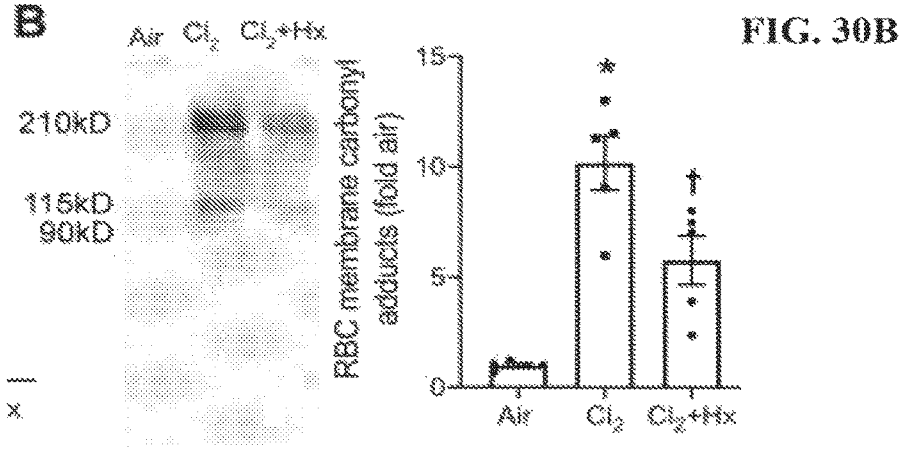
Figure 30C:
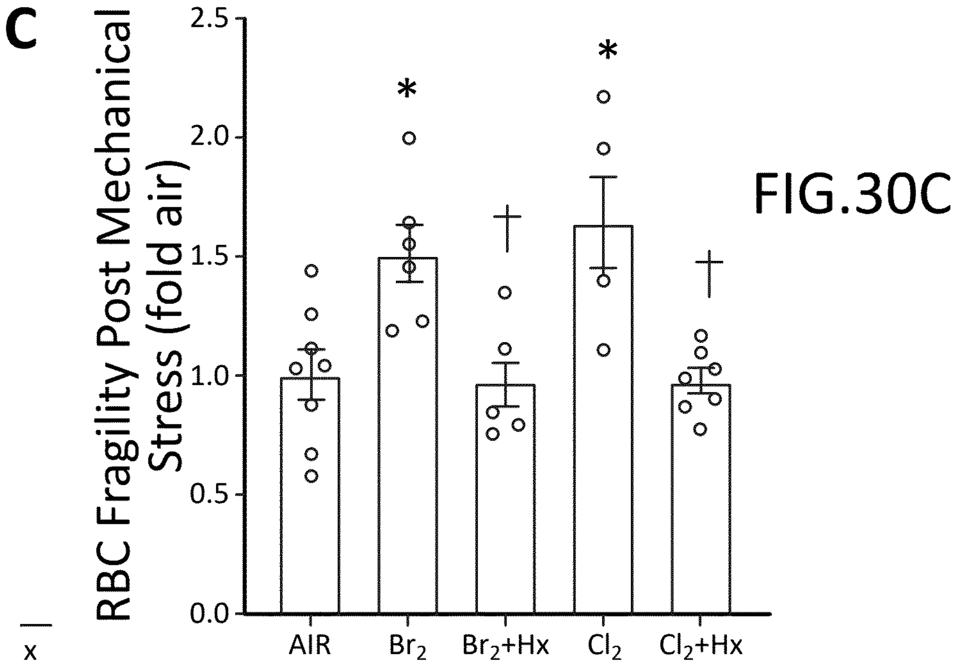
Figure 31A:
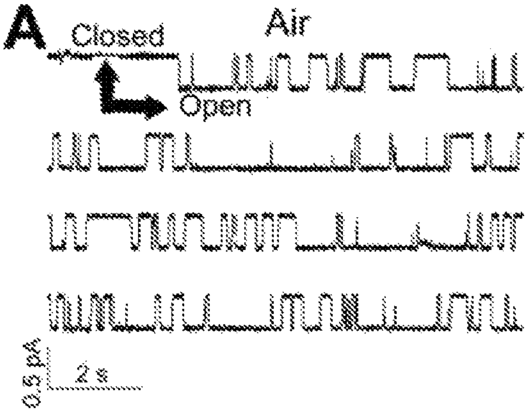
FIGS. 31A-31H show heme scavenging improves EnaC function.
Figure 31B:
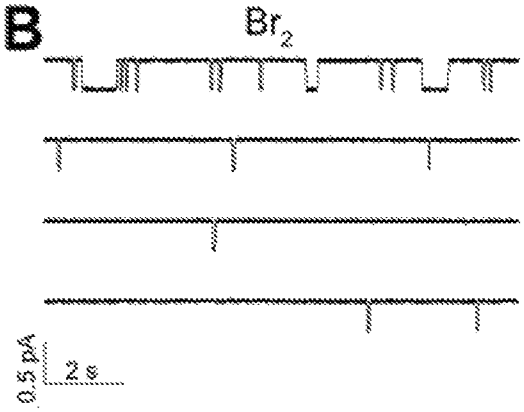
Figure 31C:
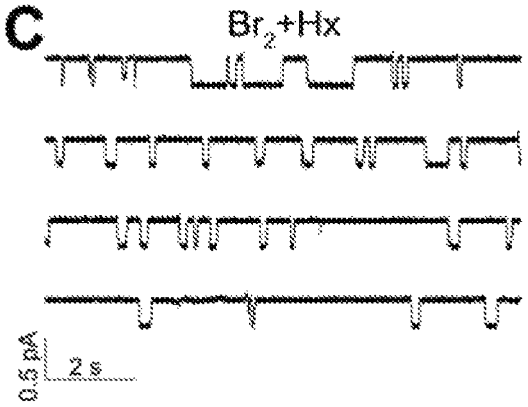
Figure 31D:
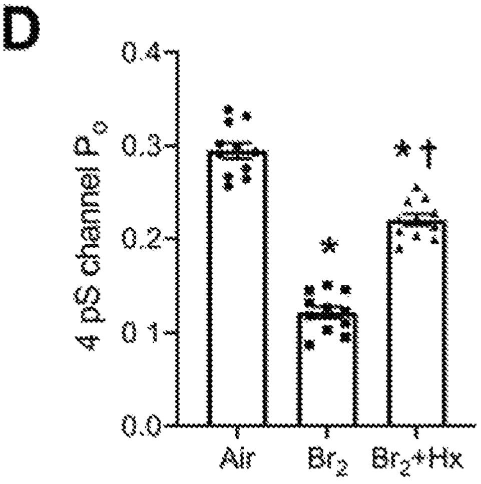
Figure 31E:
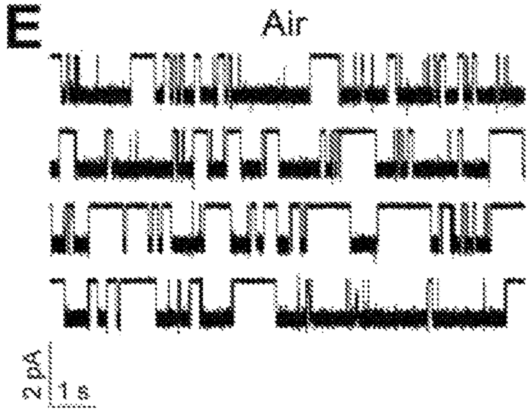
Figure 31F:
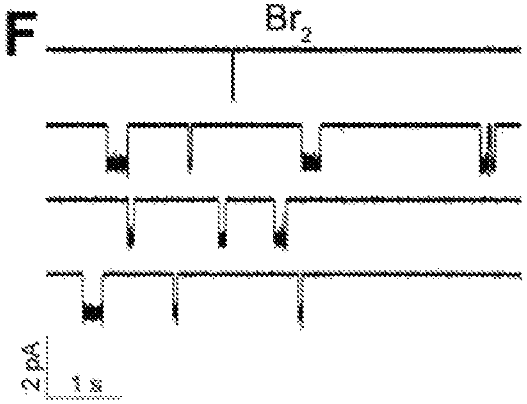
Figure 31G:
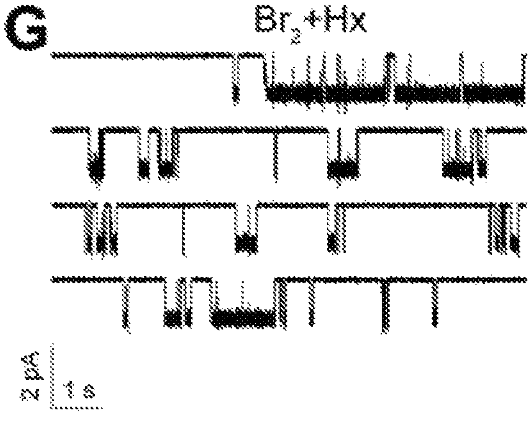
Figure 31H:
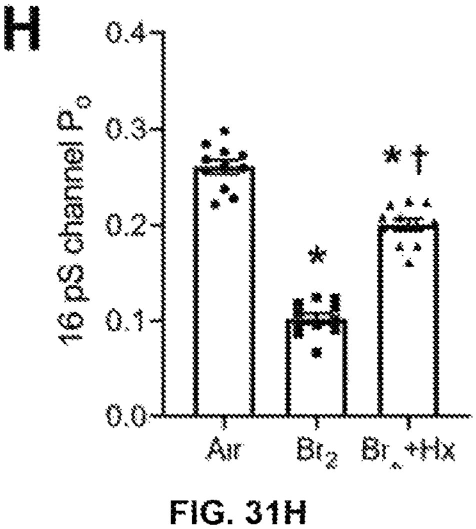

Heme scavenging attenuates RBC hemolysis and improves ENaC activity post halogen gas exposure. Next, to determine whether scavenging CFH would improve the integrity of RBC's plasma membrane and prevent hemolysis, C57BL/6 mice were exposed to $Br_2$ (600 ppm) or $Cl_2$ (400 ppm) for 30 min and then treated with an intramuscular injection of the heme scavenging protein, hemopexin, (4 mg/kg BW) 1 h later. The plasma bioavailability of hemopexin in a 25 g mouse receiving 100 μg hemopexin intramuscularly is about 25 μg/ml (total volume of blood in a 25 g mouse is about 1 ml) for at least 24 h. The serum half-life of hemopexin is approximately 7 days, while that of heme-Hpx complex is about 7 h. The RBCs were isolated from mice 1-day post exposure. Results demonstrated that hemopexin attenuated RBC plasma membrane protein carbonyl adducts post $Br_2$ (FIG. 30A) and $Cl_2$ (FIG. 30B) gas exposure. The exposure of isolated RBC to mechanical stress also showed that hemopexin reduced RBC hemolysis in the RBCs obtained from mice exposed to $Br_2$ or $Cl_2$ gas (FIG. 30C).

Lastly, to determine whether heme scavenging would improve ENaC activity by increasing the open probability ($P_0$) of 4 pS and 16 pS channels in a mouse model of $Br_2$ induced lung injury, adult male C57BL/6 mice were exposed to air or $Br_2$ and then treated with either saline or hemopexin (4 mg/kg BW) as mentioned above. Mice were sacrificed 24 h post exposure and lungs were isolated. AT2 cells in lung slices were patched in the cell-attached mode. Our data showed that the open probability of 4 pS (FIGS. 31A-31D) and 16 pS (FIGS. 31E-31H) was significantly attenuated after $Br_2$ exposure. However, mice that were treated with hemopexin after $Br_2$ exposure had significant recovery in the open probability of both the 4 pS (FIGS. 31A-31D) and 16 pS (FIGS. 31E-31H) channels. Together these results show that CFH released post exposure to halogen gas or halogenated lipids exaggerates RBC hemolysis and further contributes to RBC defect. The scavenging of free heme by hemopexin not only reduces RBC hemolysis, it also improves the activity of ENaC post lung injury.

Example 4: Chlorine and Phosgene Exposure in Neonatal Animals Results in Aberrant Lung Development Materials and Methods Neonatal mice were exposed to air or to $Cl_2$ (400/30), treated with vehicle or hemopexin (10 mg/kg, IM) 1-hour post exposure and lungs were prepared for histology at 24-hour post exposure. Neonatal mice were also exposed to $COCl_2$ and respiratory mechanics were assessed at P14 (stage of 2-4 year old child).

Results

Figures 32A, 32B, 32C:
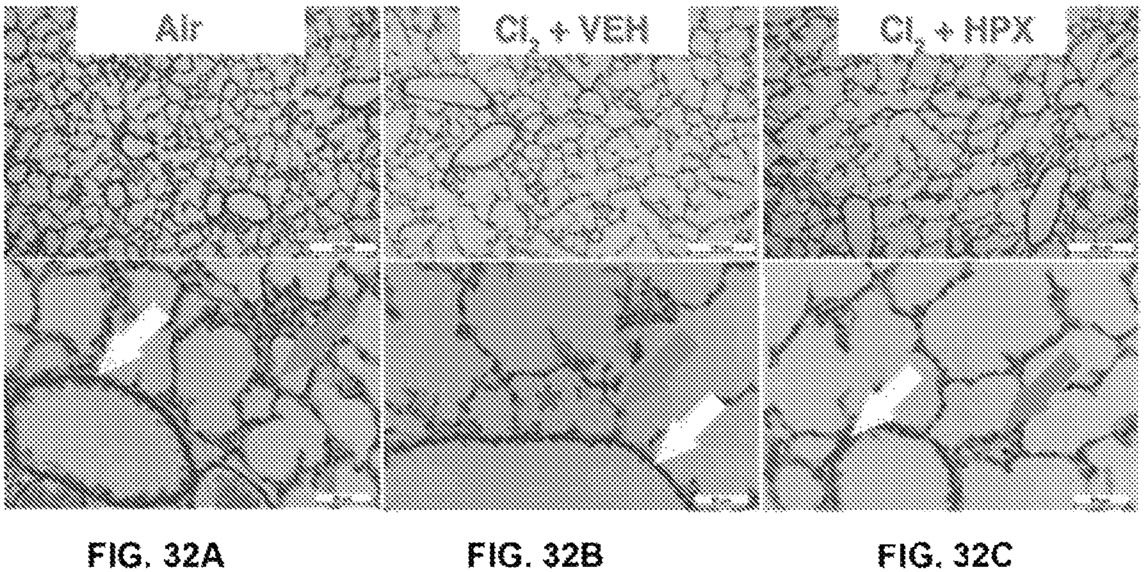
FIGS. 32A-32C show neonatal acute lung injury elicited by $Cl_2$ exposure and treatment effects of hemopexin.
Figure 33A:
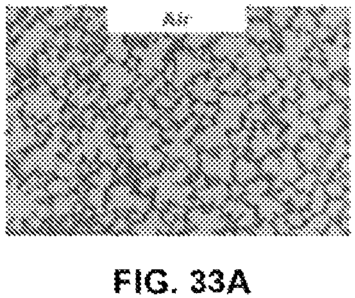
FIGS. 33A-33E show neonatal acute lung injury elicited by $Cl_2$ exposure and treatment effects of hemopexin at the P14 stage.
Figure 33B:
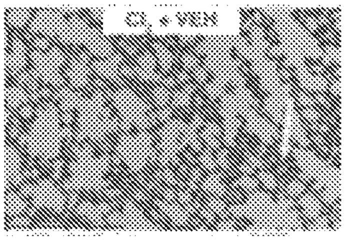
Figure 33C:
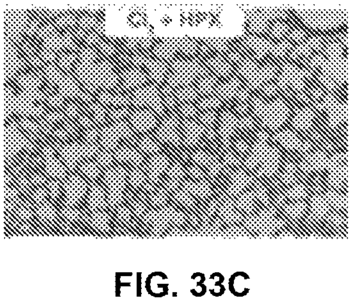

Neonatal mice were exposed to $Cl_2$ (400/30) at P3 (full term newborn stage) and their lung morphology was evaluated 24 h later at P4 (FIGS. 32A-32C). Alternatively, some mice were monitored for survival and their lung morphology was evaluated at P14 (stage of 2-4 year old child) (FIGS. 33A-33C). At P3, in the normal developing mouse lung the alveolar septae are thick (FIG. 32A, blue arrow), due to an extensive amount of mesenchymal cells which are required for alveolar growth and septation. In the lungs of mice exposed to $Cl_2$ at 24 h post-exposure, this high cellularity of septae is diminished (FIG. 32B, blue arrow) and exhibited some recovery in HPX-treated $Cl_2$ exposed mice (FIG. 32C, blue arrow). There were RBCs observed in the alveoli of $Cl_2$ exposed mice (FIG. 32B, middle, magenta asterisk). The apical cytoplasm of the bronchial epithelium appeared diminished in $Cl_2$ exposed vehicle treated mice (FIG. 32B, yellow arrow) and exhibited some improvement in HPX-treated $Cl_2$ exposed mice (FIG. 32C, yellow arrow).

Figure 33D:
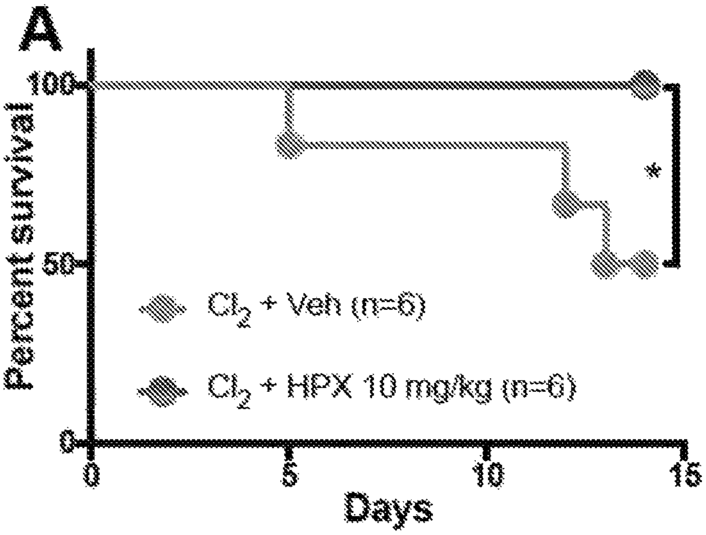
Figure 33E:
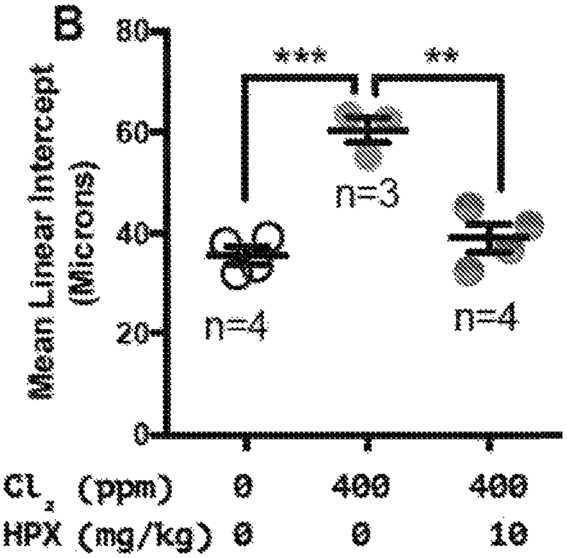

When mice exposed to $Cl_2$ (400/30) at P3 were monitored until P14, mortality (FIG. 33D) and altered alveolar development, as shown on histology images (FIGS. 33A-33C), were observed. In addition, the mice manifested an increase in mean linear intercept (MLI; FIG. 33E), i.e., MLI is inversely correlated with alveolar size and MLI normally exhibits a gradual decrease from P3 to P14 as a function of alveolar septation. Post-exposure administration of HPX improved survival and resulted in decreased MLI.

Figure 34A:
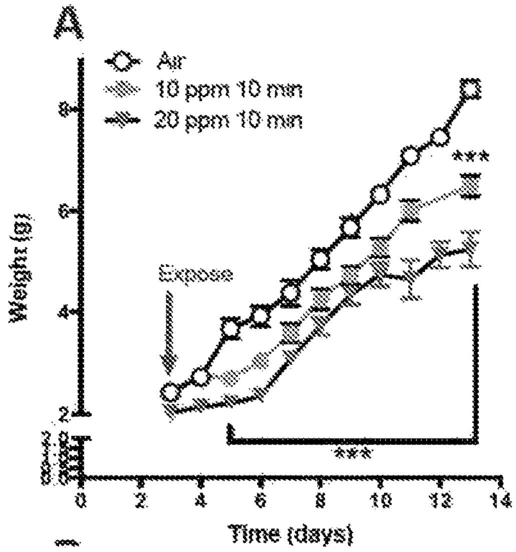
Figure 34B:
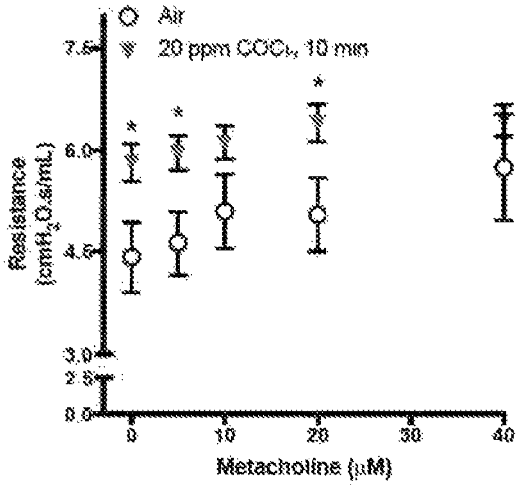
Figure 34C:
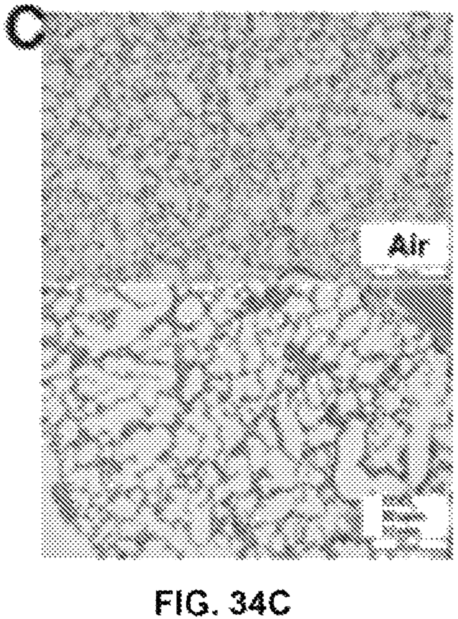
Figure 34D:
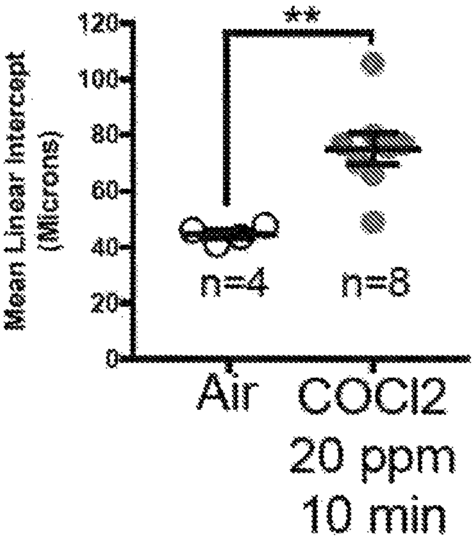
FIG. 34D is a graph showing the mortality of mice exposed to $Cl_2$ and the mortality of mice exposed to $Cl_2$ with a hemopexin treatment.

Similar to $Br_2$ and $Cl_2$, exposure of neonatal mice to $COCl_2$ caused an exposure level-dependent failure to thrive (FIG. 34A) and when respiratory mechanics were assessed on P14, it was found that mice exposed to $COCl_2$ had a highly increased baseline airway resistance, which was not responsive to methacholine (FIG. 34B). When lung morphology was assessed at P14, a drastic alteration of alveolar morphology (FIG. 34C) was shown, which manifested in a doubling of MLI (FIG. 34D). These findings support the hypothesis that exposure to toxic gases early in lung development results in aberrant development, manifesting in abnormal structure and diminished function.

Figure 35A:
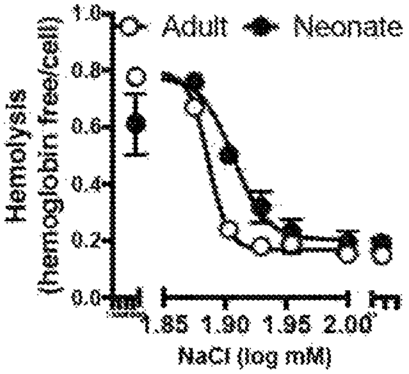
FIGS. 35A-35D show free heme and regulation of HO1 in neonates.
Figure 35B:
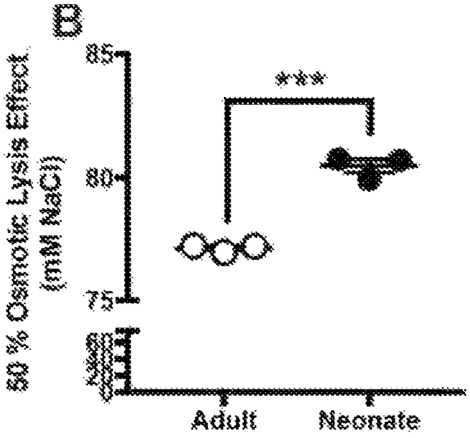
Figure 35C:
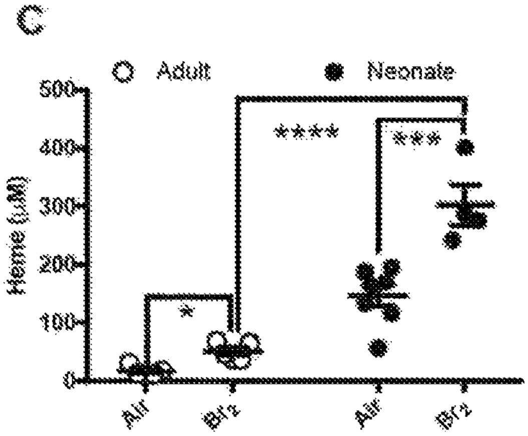
Figure 35D:
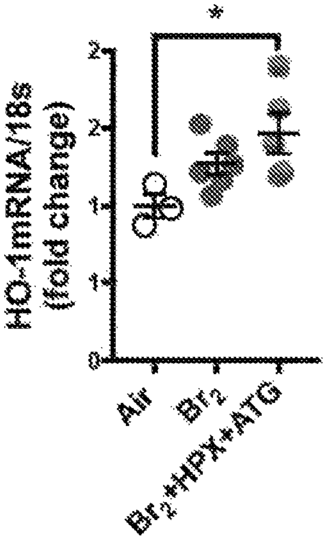

Example 5: Assessment of Differences in Toxicant Metabolism Between Adult and Neonatal Mice Oxidant damage and accumulation of oxidized lipids in the RBC membrane increase osmotic fragility of red blood cells [40]. Fetal and neonatal RBCs are larger and have significantly higher osmotic fragility compared to adult BRCs [41-42]. To assess corpuscular fragilities of adult and neonatal RBCs, they were subjected to assays of osmotic fragility. In this assay, percent lysis was plotted as a function of log[NaCl]. The points were fitted with a sigmoidal curve (FIG. 35A) and mean corpuscular fragility index (MCF; NaCl concentration causing 50% lysis) was determined (FIG. 35B). Neonatal RBCs exhibited higher mean corpuscular fragility. When heme levels were evaluated in plasma samples of adult and neonatal mice exposed to $Br_2$ (600/30) 24 h post exposure, significantly higher levels were found in neonates as compared to adults (FIG. 35C).

Figure 36:
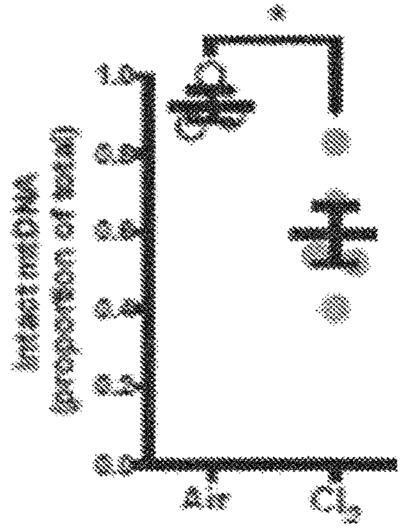
FIG. 36 shows mitochondrial DNA damage assessed by real time PCR with or without FPG treatment of DNA. Intact mtDNA=relative concentration of FPG treated/non-FPG treated DNA by real time PCR. $P<0.05$; t test.

In addition, studies were performed in DNA isolated from lung tissue of neonatal mice 24 h after exposure to $Cl_2$ (400/30) at P3 to quantify mitoDNA integrity. DNA was either untreated or was treated with formamidopyridine DNA glycosylase (FPG), then subjected to real time PCR quantification using primers specific to the mitoDNA-encoded subunit 4 of NADH dehydrogenase (ND4) gene. FPG creates strand breaks at formamidopyrimidine and 8-oxo-G modifications, and thus, samples with damaged mitoDNA exhibited increased CT values in qPCR reactions using FPG-treated DNA relative to reactions using untreated DNA. FIG. 36 shows DNA concentration ratios of FPG treated/non-FPG-treated samples calculated using the 2DDCt method, which represent the relative proportion of intact DNA in the sample. There is a decrease of intact mitoDNA at 24 h after exposure to $Cl_2$ (400/30) (FIG. 36).

Example 6: Administration of ATG Improves the Efficacy of HPX

Figure 37A:
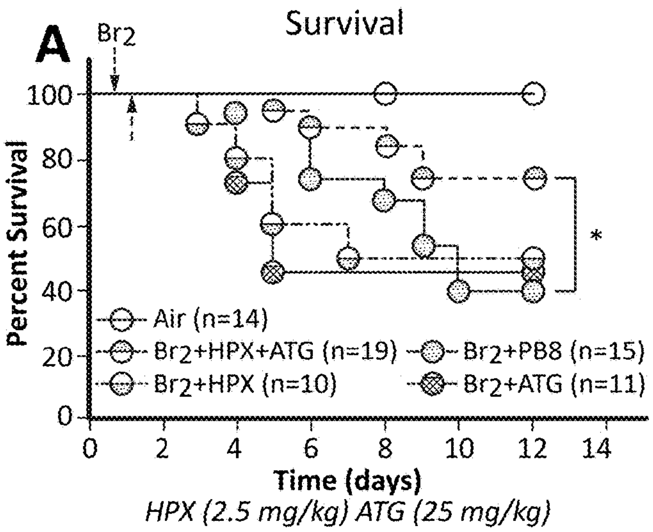
FIGS. 37A-37B show the effects of administration of both HPX and ATG.
Figure 37B:
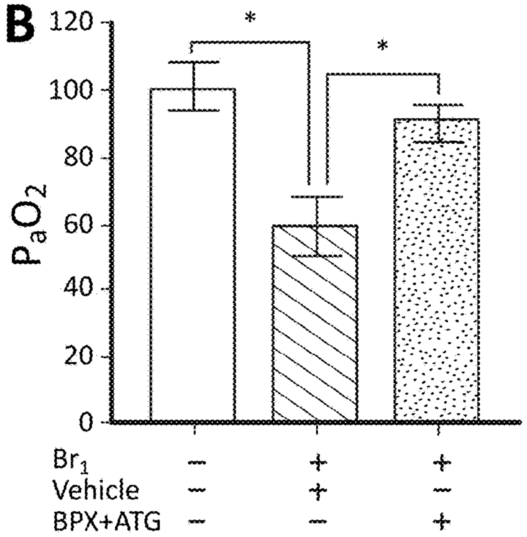
Figure 38A:
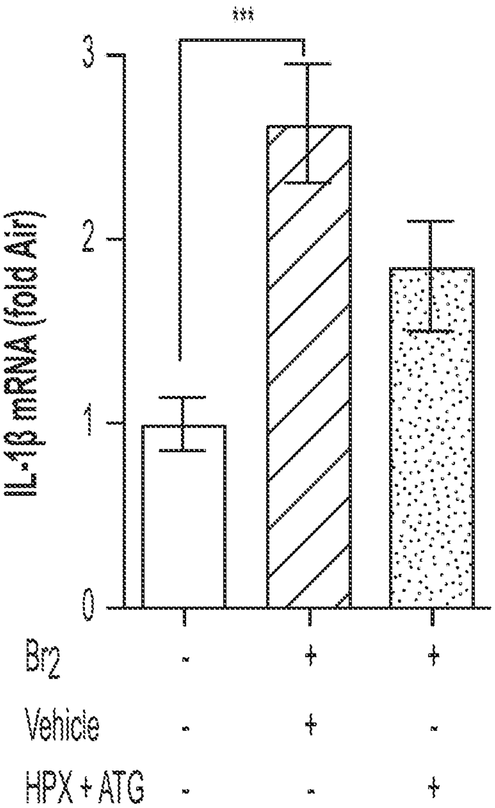
FIGS. 38A-38C show that treatment with HPX and ATG reduces persistent inflammation in neonatal mice at P14, 11 days after exposure to $Br_2$.
Figure 38B:
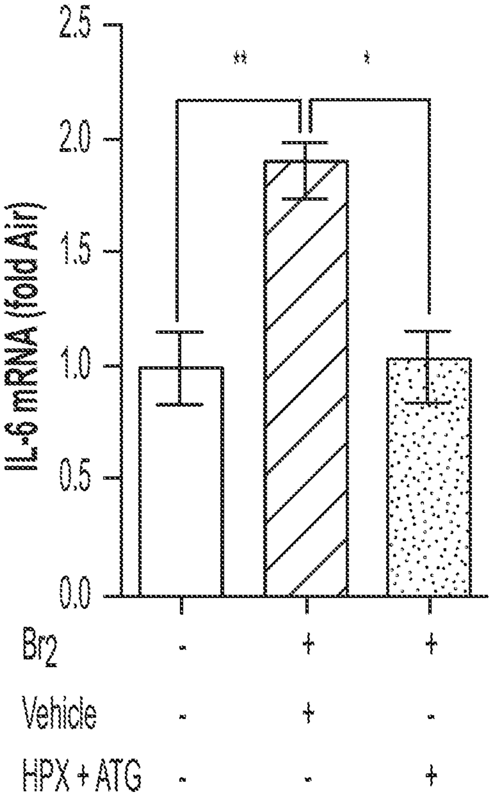
Figure 38C:
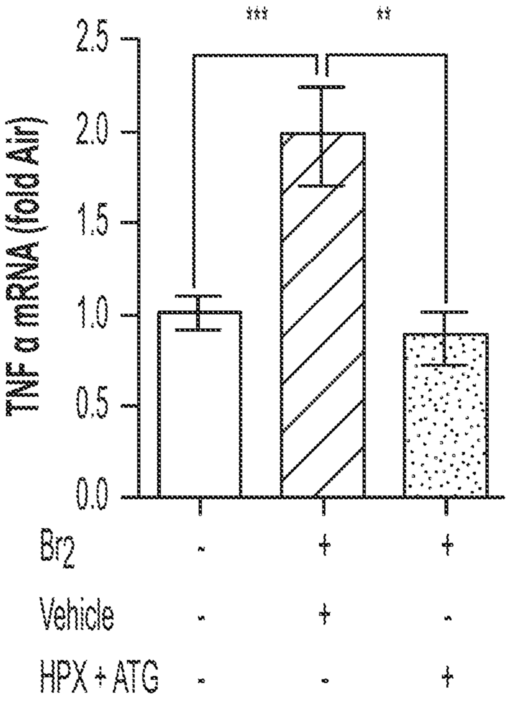

Neonatal mice were exposed to $Br_2$ (600/30) and treated with doses of 2.5 mg/kg HPX (IM) or 25 mg/kg ATG (IM). It was found that the doses of 2.5 mg/kg HPX (IM) or 25 mg/kg ATG (IM) alone were not effective to alleviate mortality and systemic hypoxia in $Br_2$ (600/30) exposed neonatal mice, but the administration of both compounds improved survival (FIG. 37A) and $PaO_2$ (FIG. 37B). Indeed, the combination of HPX and ATG improved mortality and arterial oxygenation of $Br_2$ exposed mice. Additionally, there was a sustained increase of IL-1 b, IL-6 and TNFa mRNA, as quantified by real time PCR, at P14 in murine lungs exposed to $Br_2$ at P3, which was then significantly reduced in HPX and ATG treated lungs (FIGS. 38A-38C). As such, the administration of ATG improved the efficacy of HPX.

Figure 39A:
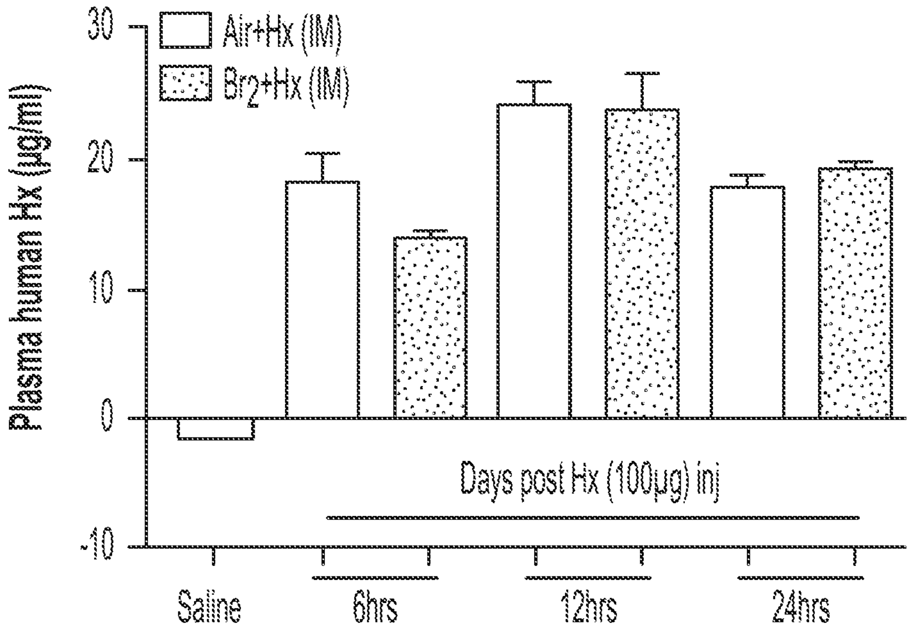
FIGS. 39A-39B show the plasma bioavailability of hemopexin.
Figure 39B:
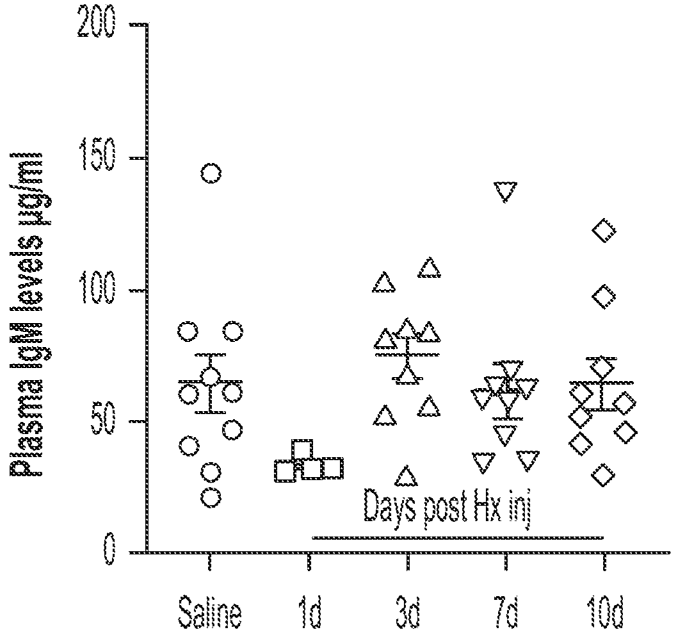

Example 7: Hemopexin Attenuates Toxic Gas-Induced Acute Lung Injury (ALI) and Mortality Plasma bioavailability of HPX. Male C57BL/6 mice were exposed to air or $Br_2$ (600 ppm, 30 min) and then 1 hour later injected with either saline or hemopexin (HPX) (4 μg/g BW for a total of 100 μg, IM; BW of a mouse being 25 gm). The data shows that the bioavailability of HPX in plasma is similar in mice exposed to air or $Br_2$ and remains stable for at least 24 h post injection (FIG. 39A). Plasma IgM levels were also measured in mice to determine if the administration of a single dose of human HPX elicits immune response. Although there was some scatter in the data, plasma [IgM] at seven-day post exposure were no more that 8% higher than the control ($p>0.5$) (FIG. 39B).

Figure 40A:
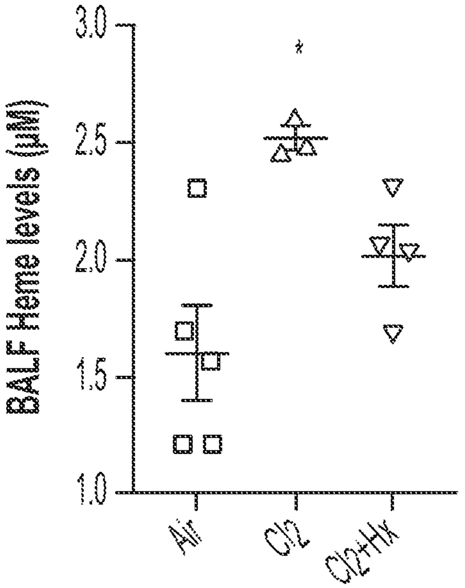
FIGS. 40A-40E show hemopexin ameliorates toxic gas-induced lung injury and mortality.
Figure 40B:
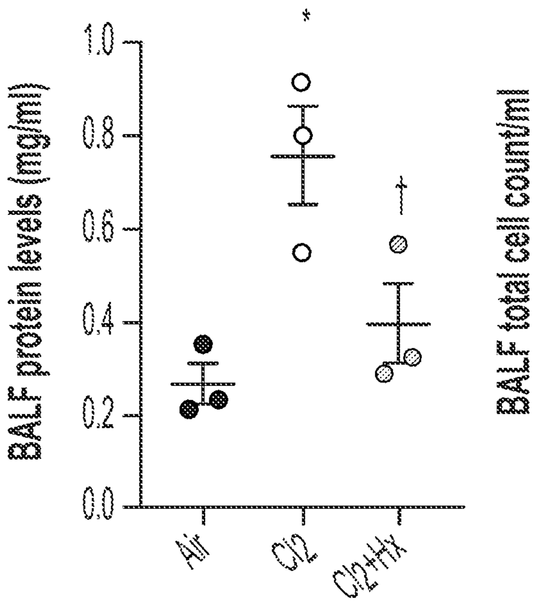
Figure 40C:
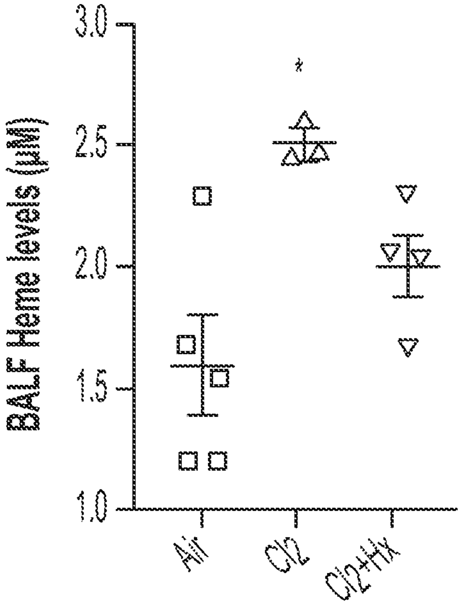
Figure 40D:
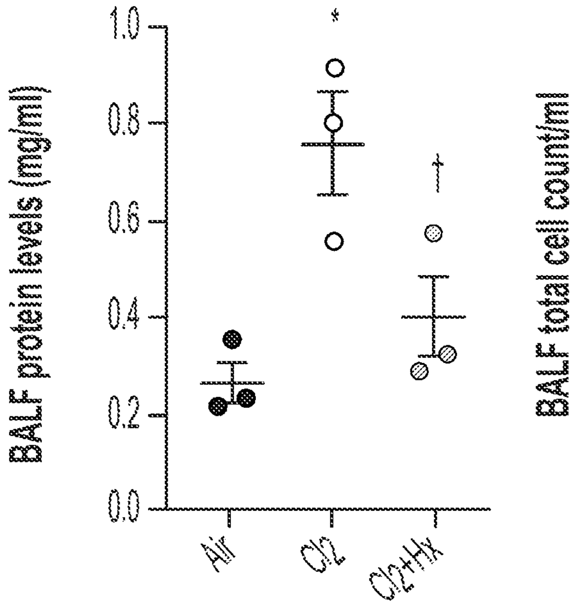
Figure 40E:
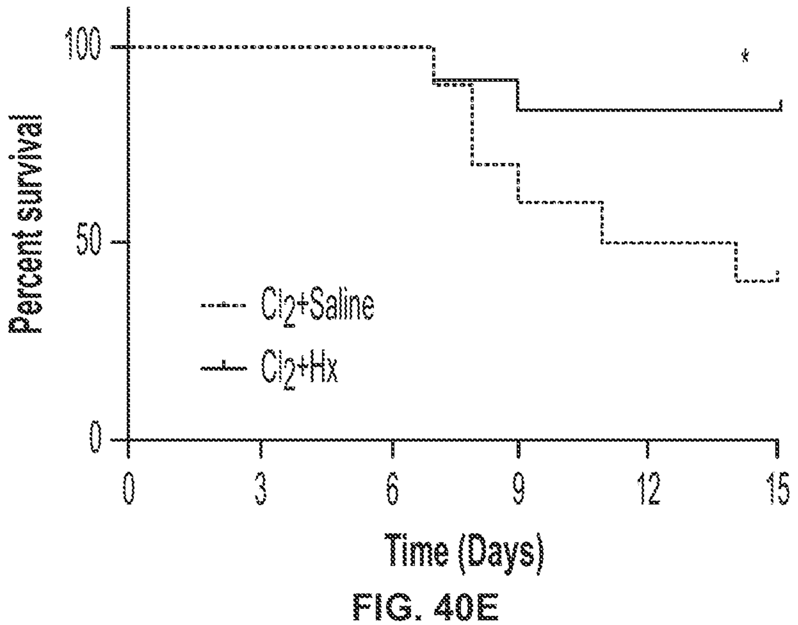
Figure 40F:
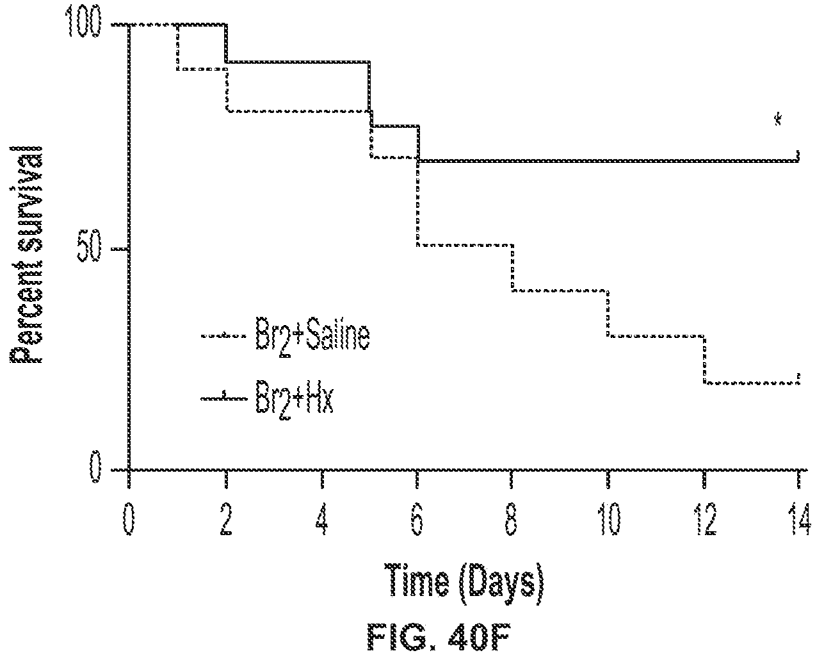

HPX attenuates toxic gas-induced ALI and mortality. Adult male C57BL/6 mice were exposed to air, $Cl_2$, $Br_2$, or $COCl_2$ followed by an IM injection of saline or HPX (4 μg/g BW), 1 hour later. HPX attenuated $Cl_2$ (600 ppm, 30 min) induced increase in BALF heme (FIG. 40A), proteins (FIG. 40B), and inflammatory cell count (FIG. 40C) 1-day post exposure. Similarly, HPX reduced $COCl_2$ (20 ppm, 10 min)-induced increase in BALF protein levels (FIG. 40D). The Kaplan-Meier survival curve indicated that HPX treatment 1-hour post insult reduced mortality in mice exposed to $Cl_2$ (400 ppm, 30 min) (FIG. 40E) or $Br_2$ (600 ppm, 30 min) (FIG. 40F).

Example 8: Hemopexin Reduces Lung Infection Post Halogen Exposure

Figure 41A:
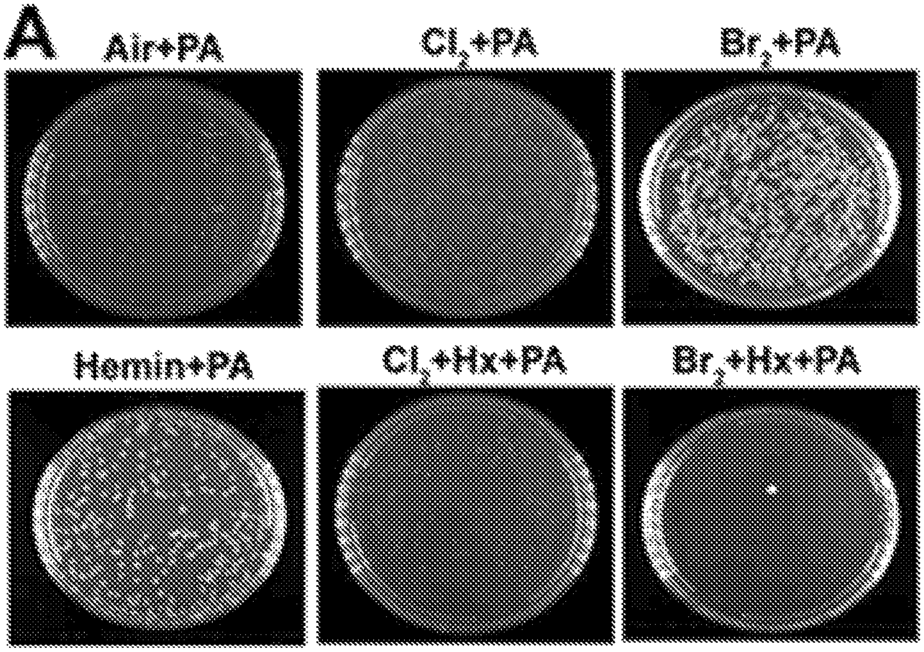
FIGS. 41A-41B show hemopexin reduced lung infection post halogen exposure.
Figure 41B:
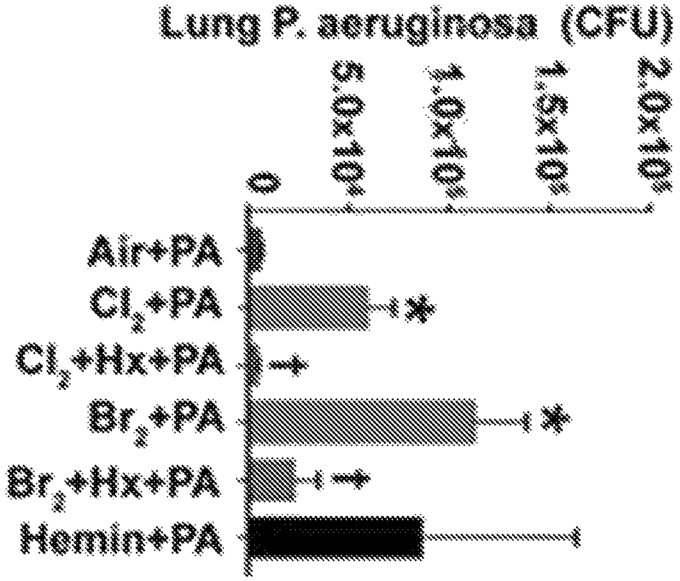
Figure 42:
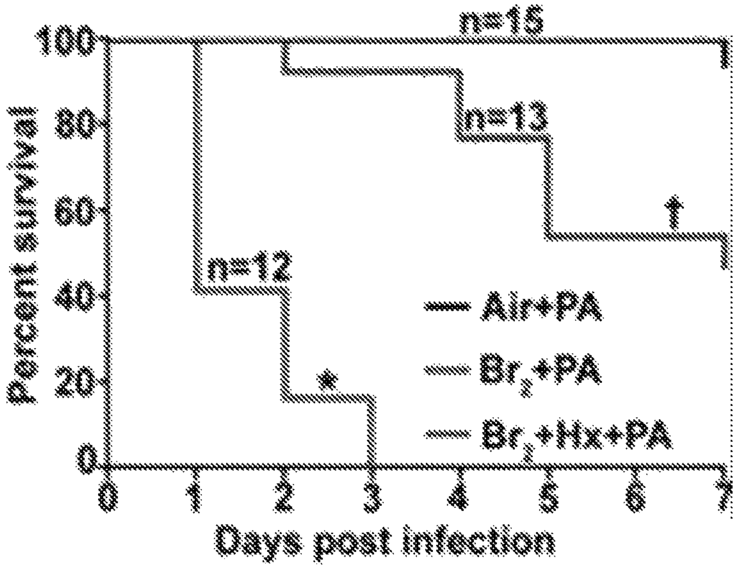
FIG. 42 is a Kaplan-Meier survival curve showing that hemopexin improved survival in mice exposed to $Br_2$ and challenged with *P. aeruginosa*.

HPX reduces lung infection post halogen exposure. To show that bacterial lung infections post toxic gas exposure is a major problem, male C57BL/6 mice exposed to $Cl_2$ or $Br_2$ (600 ppm, 30 min) were given a HPX (4 μg/g BW, IM) injection 1 hour later, and then challenged with an IT bolus of *P. aeruginosa* (strain PAK) (105 CFU in 30 μL solution) 4 days post toxic gas exposure: The lungs were removed and homogenized 1-day post infection and cultured overnight on agar plates. Mice exposed to $Cl_2$ or $Br_2$ gas had significantly higher rates of lung infection compared to the air exposed mice as shown by higher levels of bacterial colonies on agar plates (FIG. 41A). Lungs from HPX treated mice grew fewer bacterial colonies. Hemin (10 μl solution of 10 mM, IP) was used as a positive control to show the role of heme in increasing susceptibility to bacterial infections. FIG. 41B shows the average lung CFU of the bacteria on agar plates. HPX also improved survival in mice challenged with *P. aeruginosa* after $Br_2$ gas exposure (FIG. 42).

Figure 43:
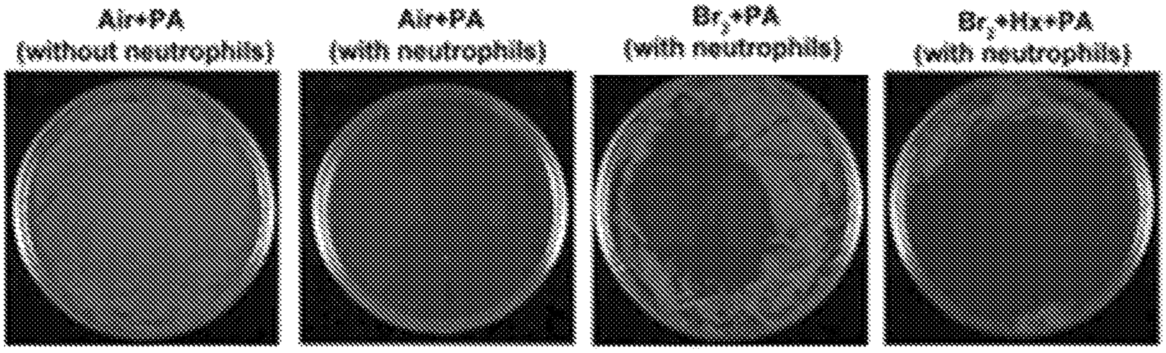
FIG. 43 are images of bacterial colonies showing that hemopexin treatment improved neutrophil function.

HPX improves bactericidal function of neutrophils. To show that the increased susceptibility to bacterial lung infections post toxic gas inhalation is due to impaired bactericidal function of immune cells, male C57BL/6 mice exposed to $Br_2$ (600 ppm, 30 min) were given HPX 1 hour later (4 μg/g BW, IM) and neutrophils from blood were isolated after 1 day. In an ex vivo system, neutrophils (105 cells/ml) were co-incubated with mid-log bacterial cultures of *P aeruginosa* (105 CFU/ml) for 30 min (5% CO2, 37° C.) with shaking and cultured overnight on agar. $Br_2$ diminished the bactericidal activity of neutrophils, while HPX improved neutrophil function (FIG. 43) as indicated by bacterial colonies on agar plates.

Example 9: Protective Effects of Hemopexin on Phosgene Exposed Mice

Figure 44:
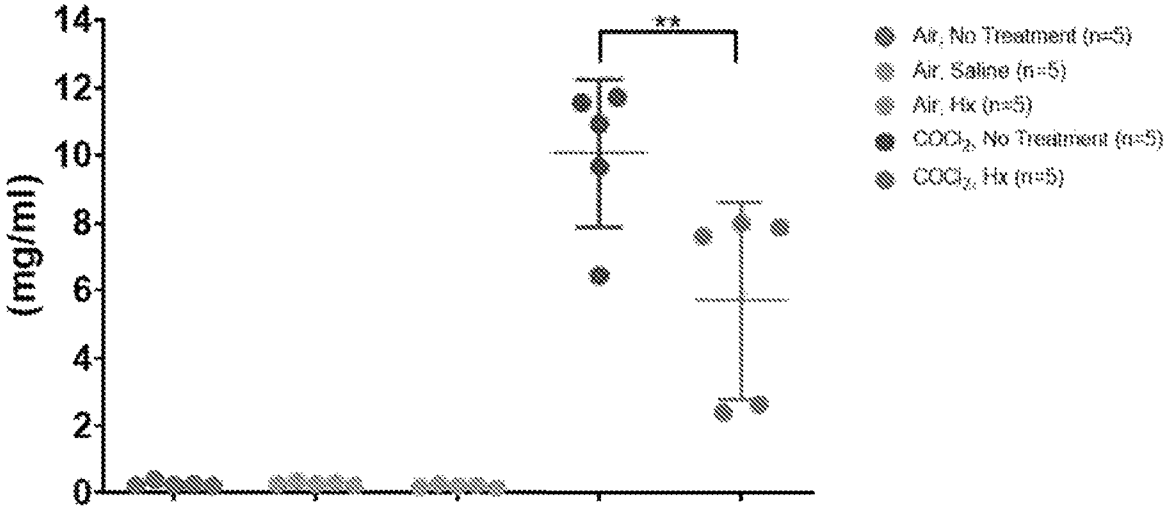
FIG. 44 is a graph showing the protective effects of hemopexin on phosgene exposed mice.

Adult male C57BL/6 mice were exposed to $COCl_2$ (20 ppm) or air in a cylindrical glass chamber for 10 minutes. Six hours post exposure, mice were treated with an intramuscular injection of either saline or hemopexin. As shown in FIG. 44, the $COCl_2$ exposed mice that were administered hemopexin demonstrated reduced BALF protein levels when compared to the $COCl_2$ exposed mice that did not receive hemopexin.

Figure 45:
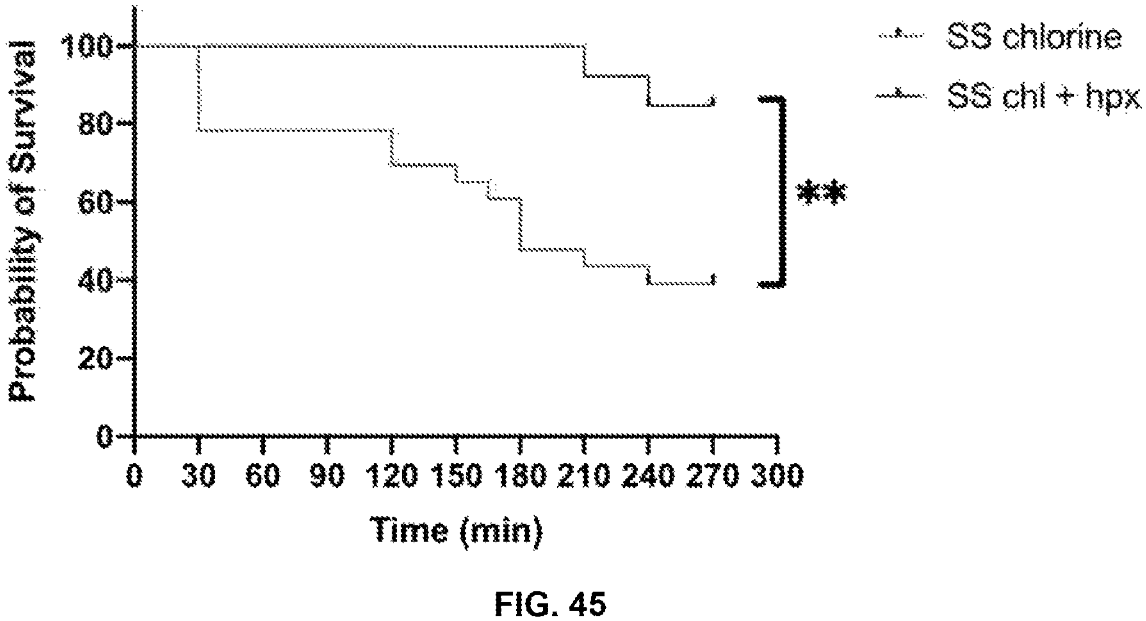
FIG. 45 is a graph showing the protective effects of hemopexin on mice with sickle cell disease exposed to chlorine.

Example 10: Protective Effects of Hemopexin on Mice with Sickle Cell Disease Exposed to Chlorine Mice having sickle cell disease were exposed to chlorine (500 ppm) for 30 minutes. Following exposure, a subset of the mice having sickle cell disease were injected with hemopexin (10 mg/kg). As shown in FIG. 45, the mice that were administered hemopexin sustained a higher probability of survival over the course of 300 minutes than the mice that were not administered hemopexin.

Example 11: Synergism Between Hemopexin and Nitrite on Mice Exposed to $Br_2$

IM injection of nitrite, post-$Cl_2$ gas exposure, decreases ALI and reactive airways in mice and rats. Nitrite is chemically stable, can be stockpiled, and is amenable to administration in mass-casualty scenarios. It was hypothesized that nitrite may be protective against $Br_2$. The studies in this example test whether the efficacy of nitrite-cytoprotection is improved by combining with other therapeutics, specifically hemopexin, that also protect against hemolysis-dependent injury. FIG. 46 presents data (n=10) showing that the combination of nitrite and hemopexin improves survival post $Br_2$ more effectively than nitrite or hemopexin alone. Hemopexin alone improved survival (p=0.08) and nitrite improved survival early (<3d) post-exposure (p=0.08). These data indicate that together, nitrite and hemopexin improve either countermeasures' therapeutic profile by allowing the use of lower concentrations, and/or resulting in greater and longer-lasting protection.

REFERENCES

The following references were cited in the above working examples. Such citation is not to be construed as an admission that any reference meets the legal definition of "prior art" in any country, nor as an admission that any reference is relevant to the patentability of anything claimed. Any such reference shall be incorporated herein by reference only to the extent it is necessary for a person of ordinary skill in the art to make and use anything claimed.

1. Miller M R, et al. Standardisation of spirometry. *Eur Respir J.* 2005; 26(2):319-338.
2. Vogelmeier C F, et al. Global Strategy for the Diagnosis, Management, and Prevention of Chronic Obstructive Lung Disease 2017 Report. GOLD Executive Summary. *Am J Respir Crit Care Med.* 2017; 195(5): 557-582.
3. Raju S V, et al. A ferret model of COPD-related chronic bronchitis. *JCI Insight.* 2016; 1(15):e87536.
4. Leustik M, et al. Mitigation of chlorine-induced lung injury by low-molecular-weight antioxidants. *Am J Physiol Lung Cell Mol Physiol.* 2008; 295(5):L733-L743.
5. Song W, et al. Inhibition of lung fluid clearance and epithelial Na+ channels by chlorine, hypochlorous acid, and chloramines. *J Biol Chem.* 2010; 285(13): 9716-9728.
6. Vardell E. JoVE: the Journal of Visualized Experiments. *Med Ref Serv Q.* 2015; 34(1):88-97.
7. Li C, et al. Chlorine induces the unfolded protein response in murine lungs and skin. *Am J Respir Cell Mol Biol.* 2013; 49(2):197-203.
8. Aggarwal S, et al. Heme attenuation ameliorates irritant gas inhalation-induced acute lung injury. *Antioxid Redox Signal.* 2016; 24(2):99-112.
9. Sharafkhaneh A, Hanania N A, Kim V. Pathogenesis of emphysema: from the bench to the bedside. *Proc Am Thorac Soc.* 2008; 5(4):475-477.
10. Boyce M, et al. A selective inhibitor of eIF2alpha dephosphorylation protects cells from ER stress. *Science.* 2005; 307(5711):935-939.
11. Moreno J A, et al. Sustained translational repression by eIF2α-P mediates prion neurodegeneration. *Nature.* 2012; 485(7399):507-511.
12. Liu C L, et al. Salubrinal protects against tunicamycin and hypoxia induced cardiomyocyte apoptosis via the PERK-eIF2α signaling pathway. *J Geriatr Cardiol.* 2012; 9(3):258-268.
13. T. Zhou, et al. Instillation of hyaluronan reverses acid instillation injury to the mammalian blood gas barrier. *Am. J. Physiol. Lung Cell Mol. Physiol.,* 314 (2018).
14. X. Han, et al. Shotgun lipidomics of phosphoethanolamine-containing lipids in biological samples after one-step in situ derivatization. *J. Lipid Res.,* 46 (2005).
15. H. G. Folkesson, et al. Acid aspiration-induced lung injury in rabbits is mediated by interleukin-8-dependent mechanisms. *J. Clin. Invest.,* 96 (1995).
16. S. A. Cucinell. Review of the toxicity of long-term phosgene exposure. *Arch. Environ. Health,* 28 (1974).
17. V. G. Demarco, et al. Obesity-related alterations in cardiac lipid profile and nondipping blood pressure pattern during transition to diastolic dysfunction in male db/db mice. *Endocrinology,* 154 (2013).
18. S. Balakrishna, et al. TRPV4 inhibition counteracts edema and inflammation and improves pulmonary function and oxygen saturation in chemically induced acute lung injury. *Am. J. Physiol. Lung Cell Mol. Physiol.,* 307 (2014).
19. P. T. Filipczak, et al. NOS-2 inhibition in phosgene-induced acute lung injury. *Toxicol. Sci.,* 146 (2015).
20. S. Aggarwal, et al. Heme scavenging reduces pulmonary endoplasmic reticulum stress, fibrosis, and emphysema. *JCI Insight,* 3 (2018).
21. J. A. Lambert, et al. Mechanisms and treatment of halogen inhalation-induced pulmonary and systemic injuries in pregnant mice. *Hypertension,* 70 (2017).
22. A. Gaggar, et al. There is blood in the water: hemolysis, hemoglobin, and heme in acute lung injury. *Am. J. Physiol. Lung Cell Mol. Physiol.,* 311 (2016).
23. I. Y. Haddad, et al. Mechanisms of peroxynitrite-induced injury to pulmonary surfactants. *Am. J. Physiol.,* 265 (1993).
24. E. J. Lee, et al. Dynamic arterial blood gas analysis in conscious, unrestrained C57BL/6J mice during exposure to intermittent hypoxia. *J. Appl. Physiol.,* 107 (2009).
25. M. Gutch, et al. Acute accidental phosgene poisoning. *BMJ Case Rep.,* 2012 (2012).
26. M. A. Duerr, et al. Bromofatty aldehyde derived from bromine exposure and myeloperoxidase and eosinophil peroxidase modify GSH and protein. *J. Lipid Res.,* 59 (2018).
27. D. A. Ford, et al. Formation of chlorinated lipids post-chlorine gas exposure. *J. Lipid Res.,* 57 (2016).
28. M. W. Oh, et al. Chlorinated fatty acids are biomarkers and potential mediators of chlorine gas toxicity. *Free Radic. Biol. Med.,* 76 (2014).
29. R. V. Branchflower, et al. Nephrotoxicity of chloroform: metabolism to phosgene by the mouse kidney, *Toxicol. Appl. Pharmacol.,* 72 (1984).
30. N. Hamasaki, et al. Band 3 protein: physiology, function and structure. *Cell Mol. Biol.,* 42 (1996).
31. S. R. Goodman, et al. Erythrocyte membrane skeletal protein bands 4.1 a and b are sequence-related phosphoprotein, *J. Biol. Chem.,* 257 (1982).
32. Albert C. J., et al. Eosinophil peroxidase-derived reactive brominating species target the vinyl ether bond of plasmalogens generating a novel chemoattractant, alpha-bromo fatty aldehyde. *J. Biol. Chem.* 278:8942-8950 (2003).
33. Wacker B. K., et al. Strategies for the analysis of chlorinated lipids in biological systems. *Free Radic. Biol. Med.* 59:92-99 (2013).
34. Duerr M. A., et al. Identification of glutathione adducts of alpha-chlorofatty aldehydes produced in activated neutrophils. *J. Lipid Res.* 56:1014-1024 (2015).
35. Pan D. et al. The effect of polymeric nanoparticles on biocompatibility of carrier red blood cells. *PloS One.* 11(2016).

36. Lazrak A. et al. Enhancement of alveolar epithelial sodium channel activity with decreased cystic, fibrosis transmembrane conductance regulator expression in mouse lung. *Am. J. Physiol. Lung Cell Mol. Physiol.* 301:L557-L567 (2011).

37. Meyer N.J. et al. Myeloperoxidase-derived 2-chloro-fatty acids contribute to human sepsis mortality via acute respiratory distress syndrome. *JCI Insight.* 2(2017).

38. Hollenhorst M. I. et al. Ion transport by pulmonary epithelia. *J. Biomed. Biotechnol.* 2011:174306 (2011).

39. Lazrak A. et al. Influenza virus M2 protein inhibits epithelial sodium channels by increasing reactive oxygen species. *Faseb. J.: Official Publication of the Federation of American Societies for Experimental Biology.* 23:3829-3842 (2009).

40. Rojas D, et al. Osmotic fragility of red blood cells, lipid peroxidation and Ca(2)(+)-ATPase activity of placental homogenates and red blood cell ghosts in salt-loaded pregnant rats. *J Matern Fetal Neonatal Med.* 29:229-33 (2016).

41. Hod I. Osmotic fragility of rat embryo red blood cells collected during intrauterine, growth. *Lab Anim* 18:81-3 (1984).

42. Zhurova M, et al. Osmotic tolerance limits of red blood cells from umbilical cord blood. *Cryobiology* 69:48-54 (2014).

CONCLUSIONS

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

The following is claimed:

1. A method of reducing the severity of clinical manifestations of an exposure to a chemical agent in a subject in need thereof, the method comprising: administering a therapeutically effective amount of hemopexin (Hpx) to the subject; wherein the chemical agent is selected from $Cl_2$, phosgene, or a combination thereof.

2. The method of claim 1, wherein the chemical agent is $Cl_2$.

3. The method of claim 1, wherein the chemical agent is phosgene.

4. The method of claim 1, wherein the subject is a neonate.

5. The method of claim 1, wherein Hpx is administered at about 0.4-100 mg/kg to the subject.

6. The method of claim 1, wherein Hpx is administered at about 2-5 mg/kg to the subject.

7. The method of claim 1, wherein Hpx is administered at about 4 mg/kg to the subject.

8. The method of claim 1, wherein Hpx is administered at about 5 mg/kg to the subject.

9. The method of claim 1, wherein Hpx is administered at about 10 mg/kg to the subject.

10. The method of claim 1, wherein Hpx is administered intramuscularly to the subject.

11. The method of claim 1, wherein Hpx is administered about one hour after the subject is exposed to the chemical agent via inhalation.

12. The method of claim 1, comprising administering an effective amount of an aurothioglucose (ATG) compound to the subject.

13. The method of claim 1, comprising administering 2.5-250 mg/kg of an aurothioglucose (ATG) compound to the subject.

14. The method of claim 1, comprising administering about 25 mg/kg of an aurothioglucose (ATG) compound to the subject.

15. The method of claim 1, comprising administering an effective amount of a salubrinal compound to the subject.

16. The method of claim 1, comprising administering 0.1-10 mg/kg of a salubrinal compound to the subject.

17. The method of claim 1, comprising administering about 1 mg/kg of a salubrinal compound to the subject.

* * * * *

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: PCR primer

<400> SEQUENCE: 1

atattgctga agagcttggc ggc                                          23


<210> SEQ ID NO 2
<211> LENGTH: 24
<212> TYPE: DNA
<213> ORGANISM: Artificial Sequence
<220> FEATURE:
<223> OTHER INFORMATION: PCR primer

<400> SEQUENCE: 2

agcaaaacaa gacagcagcc acta                                         24


<210> SEQ ID NO 3
<211> LENGTH: 24
<212> TYPE: DNA
<213> ORGANISM: Artificial Sequence
<220> FEATURE:
<223> OTHER INFORMATION: PCR primer

<400> SEQUENCE: 3

gtttctacag cttcctccac tctt                                         24
```

-continued

<210> SEQ ID NO 4
<211> LENGTH: 20
<212> TYPE: PRT
<213> ORGANISM: Homo sapiens

<400> SEQUENCE: 4

```
Gln Gln Asp Phe Glu Glu Glu Leu Ala Val Asn Glu Ile Met Leu Asn
1               5                   10                  15

Asn Leu Glu Lys
            20
```

<210> SEQ ID NO 5
<211> LENGTH: 13
<212> TYPE: PRT
<213> ORGANISM: Homo sapiens

<400> SEQUENCE: 5

```
Gly Lys Cys Asp Gln Val Glu Ser Trp Met Val Ala Arg
1               5                   10
```

<210> SEQ ID NO 6
<211> LENGTH: 12
<212> TYPE: PRT
<213> ORGANISM: Homo sapiens

<400> SEQUENCE: 6

```
Ala Leu Lys Glu Gln Leu Leu Thr Glu Leu Gly Lys
1               5                   10
```

<210> SEQ ID NO 7
<211> LENGTH: 21
<212> TYPE: PRT
<213> ORGANISM: Homo sapiens

<400> SEQUENCE: 7

```
Met Asn Gly Val Asn Glu Arg Phe Glu Asn Val Gln Ser Leu Ala Ala
1               5                   10                  15

Ala His His Glu Lys
            20
```

<210> SEQ ID NO 8
<211> LENGTH: 20
<212> TYPE: PRT
<213> ORGANISM: Homo sapiens

<400> SEQUENCE: 8

```
Leu Ser Glu Ile Ala Glu Leu Lys Asp Gln Leu Val Ala Gly Glu His
1               5                   10                  15

Ser Gln Ala Lys
            20
```

<210> SEQ ID NO 9
<211> LENGTH: 30
<212> TYPE: PRT
<213> ORGANISM: Homo sapiens

<400> SEQUENCE: 9

```
Met Gln His Asn Leu Glu Gln Gln Ile Gln Ala Lys Asp Thr Ile Gly
1               5                   10                  15

Val Ser Glu Glu Thr Leu Lys Glu Phe Ser Thr Thr Tyr Lys
            20                  25                  30
```

-continued

```
<210> SEQ ID NO 10
<211> LENGTH: 18
<212> TYPE: PRT
<213> ORGANISM: Homo sapiens

<400> SEQUENCE: 10

Val Asn Asn Tyr Cys Val Asp Cys Glu Glu Thr Ser Lys Trp Ile Met
1               5                   10                  15

Asp Lys
```